US006368792B1

(12) United States Patent
Billing-Medel et al.

(10) Patent No.: US 6,368,792 B1
(45) Date of Patent: *Apr. 9, 2002

(54) REAGENTS AND METHODS USEFUL FOR DETECTING DISEASES OF THE GASTROINTESTINAL TRACT

(75) Inventors: Patricia A. Billing-Medel, Gurnee; Maurice Cohen, Highland Park; Tracey L. Colpitts, Round Lake; Paula N. Friedman, Deerfield; Mark Hayden, Ingleside; Michael R. Klass, Libertyville; Lisa Roberts-Rapp, Gurnee, all of IL (US); John C. Russell, Kenosha, WI (US); Stephen D. Stroupe, Libertyville, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/049,698

(22) Filed: Mar. 27, 1998

Related U.S. Application Data

(63) Continuation-in-part of application No. 08/828,856, filed on Mar. 31, 1997, now abandoned.

(51) Int. Cl.[7] ................................................. C12Q 1/68
(52) U.S. Cl. ........................ 435/6; 435/91.1; 435/320.1; 435/325; 435/352; 435/363; 435/366; 435/252.3; 536/23.1
(58) Field of Search ..................... 435/6, 91.1, 320.1, 435/325, 352, 363, 366, 252.3; 536/23.1

(56) References Cited

U.S. PATENT DOCUMENTS 5,733,748 A * 3/1998 Yu et al. ..................... 435/70.1

FOREIGN PATENT DOCUMENTS

WO          WO 95/20681           8/1995

OTHER PUBLICATIONS

EST database, Accession No. W41083, Marra et al., WashU– HHMI–Mouse EST Project, Apr. 1993.*
EST database, Accession No. AA929159, ibid, Jan 1998.*

Bennett, "p53 Alterations in Progenitor Lesions of the Bronchus, Esophagus, Oral Cavity and Colon," *Cancer Detection and Prevention* 19(6):503–511 (1993).
Cunningham et al., "Coloning of an Epithelial Chloride Channel From Bovine Trachea," *J. Biol. Chem.* 270:31016–31026(1995).
Davidson et al., "Detection of Occult Nodal Metastases in Patients With Colorectal Carcinoma," *Cancer* 65:967–970 (1990).
Gerard et al., "Specific Detection of Carcinoembryonic Antigen–Expressing Tumor Cells in Bone Marrow Aspirates by Polymerase Chain Reaction," *J. of Clinical Oncology* 12(4):725–729 (1994).
Jacobs et al., "Clinical Use of Tumor Markers in Oncology," *Curr. Probl. Cancer*, p.299 Nov./ Dec. (1994).
Katz et al., "Molecular Staging of Prostate Cancer With the Use of an Enhanced Reverse transcriptase–PCR Assay," *Urology* 33(6):765–775 (1994).
Lange et al., "Serum Prostate–Specific Antigen: Its use In Diagnosis and Management of Prostate Cancer," *Supp. to Urology* 33(6):13–17 (1989).
Mansi et al., "Detection of Tumor Cells in Bone Marrow of Patients With Prostatic Carcinoma by Immunocytochemical Techniques," *J. of Urology* 139:545–548 (1988).
Matsumura et al., "Cancer Diagnosis by Detection of New Abnormalities in Splicing of CD44 Gene Products in Bladder Tumours and Urine Cell Sediments," *J. Pathol. Supp.* 175(Supp):108A (1995).
Accession No. 1706571, Epithelial Chloride Channel Protein (Calcium–Activated Chloride Channel), Oct. 1, 1996.

* cited by examiner

Primary Examiner—Stephaine Zitomer
(74) Attorney, Agent, or Firm—Cheryl L. Becker; Mimi C. Goller

(57) ABSTRACT

A set of contiguous and partially overlapping cDNA sequences and polypeptides encoded thereby, designated as CS193 and transcribed from GI tract tissue, are described. These sequences are useful for the detecting, diagnosing, staging, monitoring, prognosticating, preventing or treating, or determining the predisposition of an individual to diseases and conditions of the GI tract, such as GI tract cancer. Also provided are antibodies which specifically bind to CS193-encoded polypeptide or protein, and agonists or inhibitors which prevent action of the tissue-specific CS193 polypeptide, which molecules are useful for the therapeutic treatment of GI tract diseases, tumors or metastases.

16 Claims, 8 Drawing Sheets

```
>2767646    GCCAGGAATA ACTAGAGAGG AACAATGGGG TTATTCAGAG GTTTTGTTTT
>774134                CTAGAGAGG AACAATGGGG TTATTCAGAG GTTTTGTTTT
>774134IH              CTAGAGAGG AACAATGGGG TTATTCAGAG GTTTTGTTTT
Consensus   GCCAGGAATA ACTAGAGAGG AACAATGGGG TTATTCAGAG GTTTTGTTTT >2767646    CCTCTTAGTT CTGTGCCTGC TGCACCAGTC AAATACTTCC TTCATTAAGC
>774134     CCTCTTAGTT CTGTGCCTGC TGCACCAGTC AAATACTTCC TTCATTAAGC
>774134IH   CCTCTTAGTT CTGTGCCTGC TGCACCAGTC AAATACTTCC TTCATTAAGC
Consensus   CCTCTTAGTT CTGTGCCTGC TGCACCAGTC AAATACTTCC TTCATTAAGC >2767646    TGAATAATAA TGGCTTTGAA GATATTGTCA TTGTTATAGA TCCTAGTGTG
>774134     TGAATAATAA TGGCTTTGAA GATATTGTCA TTGTTATAGA TCCTAGTGTG
>774134IH   TGAATAATAA TGGCTTTGAA GATATTGTCA TTGTTATAGA TCCTAGTGTG
Consensus   TGAATAATAA TGGCTTTGAA GATATTGTCA TTGTTATAGA TCCTAGTGTG >2767646    CCAGAAGATG AAAAAATAAT TGAACAAATA GAGGATATGC TGACTACAGC
>774134     CCAGAAGATG AAAAAATAAT TGAACAAATA GAGGATATGG TGACTACAGC
>774134IH   CCAGAAGATG AAAAAATAAT TGAACAAATA GAGGATATGG TGACTACAGC
Consensus   CCAGAAGATG AAAAAATAAT TGAACAAATA GAGGATATGG TGACTACAGC >2767646    TTCTACGTAC CTGTTTGAAG CCACAGAAAA AAGATTTTTT T
>774134     TTCTACGTAC CTGTTTGAAG CCACAGAAAA
>774134IH   TTCTACGTAC CTGTTTGAAG CCACAGAAAA AAGATTTTTT TTCAAAAATG
Consensus   TTCTACGTAC CTGTTTGAAG CCACAGAAAA AAGATTTTTT TTCAAAAATG >774134IH   TATCTATATT AATTCCTGAG AATTGGAAGG AAAATCCTCA GTACAAAAGG
Consensus   TATCTATATT AATTCCTGAG AATTGGAAGG AAAATCCTCA GTACAAAAGG >774134IH   CCAAAACATG AAAACCATAA ACATGCTGAT GTTATAGTTG CACCACCTAC
Consensus   CCAAAACATG AAAACCATAA ACATGCTGAT GTTATAGTTG CACCACCTAC >774134IH   ACTCCCAGGT AGAGATGAAC CATACACCAA GCAGTTCACA GAATGTGGAG
Consensus   ACTCCCAGGT AGAGATGAAC CATACACCAA GCAGTTCACA GAATGTGGAG >774134IH   AGAAAGGCGA ATACATTCAC TTCACCCCTG ACCTTCTACT TGAAAAAAAA
Consensus   AGAAAGGCGA ATACATTCAC TTCACCCCTG ACCTTCTACT TGAAAAAAAA >774134IH   CAAAATGAAT ATGGACCACC AGGCAAACTG TTTGTCCATG AGTGGGCTCA
Consensus   CAAAATGAAT ATGGACCACC AGGCAAACTG TTTGTCCATG AGTGGGCTCA >774134IH   CCTCCGGTGG GGAGTGTTTG ATGAGTACAA TGAAGATCAG CCTTTCTACC
Consensus   CCTCCGGTGG GGAGTGTTTG ATGAGTACAA TGAAGATCAG CCTTTCTACC >774134IH   GTGCTAAGTC AAAAAAAATC GAAGCAACAA GGTGTTCCGC AGGTATCTCT
Consensus   GTGCTAAGTC AAAAAAAATC GAAGCAACAA GGTGTTCCGC AGGTATCTCT >774134IH   GGTAGAAATA GAGTTTATAA GTGTCAAGGA GGCAGCTGTC TTAGTAGAGC
Consensus   GGTAGAAATA GAGTTTATAA GTGTCAAGGA GGCAGCTGTC TTAGTAGAGC
```

FIG. 1A

```
>774134IH    ATGCAGAATT GATTCTACAA CAAAACTGTA TGGAAAAGAT TGTCAATTCT
Consensus    ATGCAGAATT GATTCTACAA CAAAACTGTA TGGAAAAGAT TGTCAATTCT >774134IH    TTCCTGATAA AGTACAAACA GAAAAAGCAT CCATAATGTT TATGCAAAGT
Consensus    TTCCTGATAA AGTACAAACA GAAAAAGCAT CCATAATGTT TATGCAAAGT >774134IH    ATTGATTCTG TTGTTGAATT TTGTAACGAA AAAACCCATA ATCAAGAAGC
>775437                 TT NTGTAACGAA AAAACCCATA ATCAAGAAGC
Consensus    ATTGATTCTG TTGTTGAATT TTGTAACGAA AAAACCCATA ATCAAGAAGC >774134IH    TCCAAGCCTA CAAAACATAA AGTGCAATTT TAGAAGTACA TGGGAGGTGA
>775437      TCCAAGCCTA CAAAACATAA AGTGCAATTT TAGAAGTACA TGGGAGGTGA
Consensus    TCCAAGCCTA CAAAACATAA AGTGCAATTT TAGAAGTACA TGGGAGGTGA >774134IH    TTAGCAATTC TGAGGATTTT AAAAACACCA TACCCATGGT GACACCACCT
>775437      TTAGCAATTC TGAGGATTTT AAAAACACCA TACCCATGGT GACACCACCT
Consensus    TTAGCAATTC TGAGGATTTT AAAAACACCA TACCCATGGT GACACCACCT >774134IH    CCTCCACCTC TCTTCTCATT CCTCAACATC ACTCAAACAA TTCTCTCCTT
>775437      CCTCCACCTG TCTTCTCATT GCTGAAGATC AGTCAAAGAA TTGTGTGCTT
Consensus    CCTCCACCTG TCTTCTCATT GCTGAAGATC AGTCAAAGAA TTGTGTGCTT >774134IH    AGTTCTTGAT AAGTCTGGAA GCATGGGGGG TAAGGACCGC CTAAATCGAA
>775437       AGTTCTTGAT AAGTCTGGAA GCATGGGGGG TAAGGACCGC CTAAATCGA
>1281329                         TGGGGGG TAAGGACCGC CTAAATCGAA
Consensus    AGTTCTTGAT AAGTCTGGAA GCATGGGGGG TAAGGACCGC CTAAATCGAA >774134IH    TGAATCAAGC AGCAAAACAT TTCCTGCTGC AGACTGTTGA AAATGGATCC
>1281329     TCAATCAACC ACCAAAACAT TTCCTCCTCC AGACTGTTCA AAATGGATCC
Consensus    TGAATCAAGC AGCAAAACAT TTCCTGCTGC AGACTGTTGA AAATGGATCC >774134IH    TGGGTGGGGA TGGTTCACTT TGATAGTACT GCCACTATTG TAAATAAGCT
>1281329     TGGGTGGGGA TGGTTCACTT TGATAGTACT GCCACTATTG TAAATAAGCT
Consensus    TGGGTGGGGA TGGTTCACTT TGATAGTACT GCCACTATTG TAAATAAGCT >774134IH    AATCCAAATA AAAAGCAGTG ATGAAAGAAA CACACTCATG GCAGGATTAC
>1281329     AATCCAAATA AAAAGCAGTG ATGAAAGAAA CACACTCATG GCAGGATTAC
Consensus    AATCCAAATA AAAAGCAGTG ATGAAAGAAA CACACTCATG GCAGGATTAC >774134IH    CTACATATCC TCTGGGAGGA ACTTCCATCT GCTCTGGAAT TAAATATGCA
>1281329     CTACATATCC TCTGGGAGGA ACTTCCATCT GCTCTGGAAT TAAATATGCA
>1628677                              CTTCCATCT GCTCTGGAAT TAAATATGCA
Consensus    CTACATATCC TCTGGGAGGA ACTTCCATCT GCTCTGGAAT TAAATATGCA
```

FIG. 1B

```
>774134IH    TTTCAGGTGA TTGGAGAGCT ACATTCCCAA CTCGATGGAT CCGAAGTACT
>1281329     TTTCAGGTGA
>1628677     TTTCAGGTGA TTGGAGAGCT ACATTCCCAA CTCGATGGAT CCGAAGTACT
Consensus    TTTCAGGTGA TTGGAGAGCT ACATTCCCAA CTCGATGGAT CCGAAGTACT >774134IH    GCTGCTGACT GATGGGGAGG ATAACACTGC AAGTTCTTGT ATTGATGAAG
>1628677     GCTGCTGACT GATGGGGAGG ATAACACTGC AAGTTCTTGT ATTGATGAAG
Consensus    GCTGCTGACT GATGGGGAGG ATAACACTGC AAGTTCTTGT ATTGATGAAG >774134IH    TGAAACAAAG TGGGGCCATT GTTCATTTTA TTGCTTTGGG AAGAGCTGCT
>1628677     TGAAACAAAG TGGGGCCATT GTTCATTTTA TTGCTTTGGG AAGAGCTGCT
Consensus    TGAAACAAAG TGGGGCCATT GTTCATTTTA TTGCTTTGGG AAGAGCTGCT >774134IH    GATGAAGCAG TAATAGAGAT GAGCAAGATA ACAGGAGGAA GTCATTTTTA
>1628677     GATGAAGCAG TAATAGAGAT GAGCAAGATA ACAGGAG
Consensus    GATGAAGCAG TAATAGAGAT GAGCAAGATA ACAGGAGGAA GTCATTTTTA >774134IH    TGTTTCAGAT GAAGCTCAGA ACAATGGCCT CATTGATGCT TTTGGGGCTC
Consensus    TGTTTCAGAT GAAGCTCAGA ACAATGGCCT CATTGATGCT TTTGGGGCTC >774134IH    TTACATCACC AAATACTGAT CTCTCCCAGA ACTCCCTTCA GCTCGAAAGT
Consensus    TTACATCAGG AAATACTGAT CTCTCCCAGA AGTCCCTTCA GCTCGAAAGT >774134IH    AAGGGATTAA CACTGAATAG TAATGCCTGG ATGAACGACA CTGTCATAAT
>1286372                                                     AAT
Consensus    AAGGGATTAA CACTGAATAG TAATGCCTGG ATGAACGACA CTGTCATAAT >774134IH    TGATAGTACA GTGGGAAAGG ACACGTTCTT TCTCATCACA TGGAACAGTC
>1286372     TGATAGTACA GTGGGAAAGG NCACGTTCTT TCTCATCACA TGGAACAGTC
Consensus    TGATAGTACA GTGGGAAAGG ACACGTTCTT TCTCATCACA TGGAACAGTC >774134IH    TGCCTCCCAG TATTTCTCTC TGGGATCCCA GTGGAACAAT AATGGAAAAT
>1286372     TGCCTCCCAG TATTTCTCTC TGGGATCCCA GTGGAACAAT AATGGAAAAT
Consensus    TGCCTCCCAG TATTTCTCTC TGGGATCCCA GTGGAACAAT AATGGAAAAT >774134IH    TTCACAGTGG ATGCAACTTC CAAAATGGCC TATCTCAGTA TTCCAGGAAC
>1286372     TTCACAGTGG ATGCAACTTC CAAAATGGCC TATCTCAGTA TTCCAGGAAC
Consensus    TTCACAGTGG ATGCAACTTC CAAAATGGCC TATCTCAGTA TTCCAGGAAC >774134IH    TGCAAAGGTG GGCACTTGGG CATACAATCT TCAAGCCAAA GCGAACCCAG
>1286372     TGCAAAGGTG GGCACTTGGG CATACAATCT TCAAGCCAAA GCGAACCC
Consensus    TGCAAAGGTG GGCACTTGGG CATACAATCT TCAAGCCAAA GCGAACCCAG >774134IH    AAACATTAAC TATTACAGTA ACTTCTCGAG CAGCAAATTC TTCTGTGCCT
>774419                                            GCAAATTC TTCTGTGCCT
>774419IH                                          GCAAATTC TTCTGTGCCT
Consensus    AAACATTAAC TATTACAGTA ACTTCTCGAG CAGCAAATTC TTCTGTGCCT
```

FIG.1C

```
>774134IH    CCAATCACAG TGAATGCTAA AATGAATAAG GACGTAAACA GTTTCCCCAG
>774419      CCAATCACAG TGAATGCTAA AATGAATAAG GACGTAAACA GTTTCCCCAG
>774419IH    CCAATCACAG TGAATGCTAA AATGAATAAG GACGTAAACA GTTTCCCCAG
Consensus    CCAATCACAG TGAATGCTAA AATGAATAAG GACGTAAACA GTTTCCCCAG >774134IH    CCCAATGATT GTTTACGCAG AAATTCTACA AGGATATGTA CCTGTTCTTG
>774419      CCCAATGATT GTTTACGCAG AAATTCTACA AGGATATGTA CCTGTTCTTG
>774419IH    CCCAATGATT GTTTACGCAG AAATTCTACA AGGATATGTA CCTGTTCTTG
Consensus    CCCAATGATT GTTTACGCAG AAATTCTACA AGGATATGTA CCTGTTCTTG >774134IH    GAGCCAATGT GACTGCTTTC ATTGAATCAC AGAATGGACA TACAGAAGTT
>774419      GAGCCAATGT GACTGCTTTC ATTGAATCAC AGAATGGACA TACAGAAGTT
>774419IH    GAGCCAATGT GACTGCTTTC ATTGAATCAC AGAATGGACA TACAGAAGTT
Consensus    GAGCCAATGT GACTGCTTTC ATTGAATCAC AGAATGGACA TACAGAAGTT >774134IH    TTGGAACTTT TGGATAATGG TGCAGGCGCT GATTCTTTCA AGAATGATGG
>774419      TTGGAACTTT TGGATAATGG TGCAGGCGCT GATTCTTTCA AGAATGATGG
>774419IH    TTGGAACTTT TGGATAATGG TGCAGGCGCT GATTCTTTCA AGAATGATGG
>3233118              G TGCAGGCGCT GATTCTTTCA AGAATGATGG
Consensus    TTGGAACTTT TGGATAATGG TGCAGGCGCT GATTCTTTCA AGAATGATGG >774134IH    AGTCTACTCC AGGTATTTTA CAGCATATAC AGAAAATGGC AGATATAGCT
>774419      AGTCTACTCC AGGTATTTTA CAG
>774419IH    ACTCTACTCC ACCTATTTTA CACCATATAC ACAAAATCCC ACATATACCT
>3233118     AGTCTACTCC AGGTATTTTA CAGCATATAC AGAAAATGGC AGATATAGCT
Consensus    AGTCTACTCC AGGTATTTTA CAGCATATAC AGAAAATGGC AGATATAGCT >774134IH    TAAAAGTTCG GGCTCATGGA GGAGCAAACA CTGCCAGGCT AAAATTACGG
>774419IH    TAAAAGTTCG GGCTCATGGA GGAGCAAACA CTGCCAGGCT AAAATTACGG
>3233118     TAAAAGTTCG GGCTCATGGA GGAGCAAACA CTGCCAGGCT AAAATTACGG
Consensus    TAAAAGTTCG GGCTCATGGA GGAGCAAACA CTGCCAGGCT AAAATTACGG >774134IH    CCTCCACTGA ATAGAGCCGC GTACATACCA GGCTGGGTAG TGAACGGGGA
>774419IH    CCTCCACTGA ATAGAGCCGC GTACATACCA GGCTGGGTAG TGAACGGGGA
>3233118     CCTCCACTGA ATAGAGCCGC GTACATACCA GGCTGGGTAG TGAACGGGGA
Consensus    CCTCCACTGA ATAGAGCCGC GTACATACCA GGCTGGGTAG TGAACGGGGA >774134IH    AATTGAAGCA AACCCGCCAA GACCTGAAAT TGATGAGGAT ACTCAGACCA
>774419IH    AATTGAAGCA AACCCGCCAA GACCTGAAAT TGATGAGGAT ACTCAGACCA
>3233118     AATTGAAGCA AACCCGCCAA GACCTGAAAT TGATGAGGAT ACTCAGACCA
>2733923                CCCGCCAA GACCTGAAAT TGATGAGGAT ACTCAGACCA
Consensus    AATTGAAGCA AACCCGCCAA GACCTGAAAT TGATGAGGAT ACTCAGACCA
```

FIG. 1D

```
>774134IH    CCTTGGAGGA TTTCAGCCGA ACAGCATCCG GAGGTGCATT TGTGGTATCA
>774419IH    CCTTGGAGGA TTTCAGCCGA ACAGCATCCG GAGGTGCATT TGTGGTATCA
>3233118     CCTTGGAGGA T
>2733923     CCTTGGAGGA TTTCAGCCGA ACAGCATCCG GAGGTGCATT TGTCGTATCA
Consensus    CCTTGGAGGA TTTCAGCCGA ACAGCATCCG GAGGTGCATT TGTGGTATCA >774134IH    CAAGTCCCAA GCCTTCCCTT GCCTGACCAA TACCCACCAA GTCAAATCAC
>774419IH    CAAGTCCCAA GCCTTCCCTT GCCTGACCAA TACCCACCAA GTCAAATCAC
>2733923     CAAGTCCCAA GCCTTCCCTT GCCTGACCAA TACCCACCAA GTCAAATCAC
>906605                                  CCAA TACCCACCAA GTCAAATNAC
Consensus    CAAGTCCCAA GCCTTCCCTT GCCTGACCAA TACCCACCAA GTCAAATCAC >774134IH    AGACCTTGAT GCCACAGTTC ATGAGGATAA GATTATTCTT ACATGGACAG
>774419IH    AGACCTTGAT GCCACAGTTC ATGAGGATAA GATTATTCTT ACATGGACAG
>2733923     AGACCTTGAT GCCACAGTTC ATGAGGATAA GATTATTCTT ACATGGACAG
>906605      AGACCTTGAT GCCACAGTTN ATGAGGATAA GATTATTCTT ACATGGACAG
Consensus    AGACCTTGAT GCCACAGTTC ATGAGGATAA GATTATTCTT ACATGGACAG >774134IH    CACCAGGAGA TAATTTTGAT GTTGGAAAAG TTCAACGTTA TATCATAAGA
>774419IH    CACCAGGAGA TAATTTTGAT GTTGGAAAAG TTCAACGTTA TATCATAAGA
>2733923     CACCAGGAGA TAATTTTGAT GTTGGAAAAG TTCAACGTTA TATCA
>906605      CACCAGGAGA TAATTTTGAT GTTGGAAAAG TTCAACGTTA TATCATAAGA
Consensus    CACCAGGAGA TAATTTTGAT GTTGGAAAAG TTCAACGTTA TATCATAAGA >774134IH    ATAAGTGCAA GTATTCTTGA TCTAAGAGAC AGTTTTGATG ATGCTCTTCA
>774419IH    ATAAGTGCAA GTATTCTTGA TCTAAGAGAC AGTTTTGATG ATGCTCTTCA
>906605      ATAAGTGCAA GTATTCTTGA TCTAAGAGAC AGTTTTGATG ATGCTCTTCA
>2771475            AA GTATTCTTGA TCTAACACAC AGTTTTGATG ATGCTCTTCA
Consensus    ATAAGTGCAA GTATTCTTGA TCTAAGAGAC AGTTTTGATG ATGCTCTTCA >774134IH    AGTAAATACT ACTGATCTGT CACCAAAGGA GGCCAACTCC AAGGAAAGCT
>774419IH    AGTAAATACT ACTGATCTGT CACCAAAGGA GGCCAACTCC AAGGAAAGCT
>906605      AGTAAATACT ACTGATCTGT CACCAAAGGA GGCCAACTCC AAGGAAAGCT
>2771475     AGTAAATACT ACTGATCTGT CACCAAAGGA GCCCAACTCC AAGGAAAGCT
Consensus    AGTAAATACT ACTGATCTGT CACCAAAGGA GGCCAACTCC AAGGAAAGCT >774134IH    TTGCATTTAA ACCAGAAAAT ATCTCAGAAG AAAATGCAAC CCACATATTT
>774419IH    TTGCATTTAA ACCAGAAAAT ATCTCAGAAG AAAATGCAAC CCACATATTT
>906605      TTGCATTTAA ACCAGAAAAT ATCTCAGAAG AAAATGCAAC CCACATATTT
>2771475     TTGCATTTAA ACCAGAAAAT ATCTCAGAAG AAAATGCAAC CCACATATTT
>1803247                                        AN ANAATGCAAC CCACATATTT
Consensus    TTGCATTTAA ACCAGAAAAT ATCTCAGAAG AAAATGCAAC CCACATATTT
```

FIG.1E

```
>774134IH    ATTGCCATTA AAAGTATAGA TAAAAGCAAT TTGACATCAA AAGTATCCAA
>774419IH    ATTGCCATTA AAAGTATAGA TAAAAGCAAT TTGACATCAA AAGTATCCAA
>906605      ATTGCCATTA AAAGTATAGA TAAA:GCA:T TTGGCATCAA A
>2771475     ATTGCCATTA AAAGTATAGA TAAAAGCAAT TTGACATCAA AAGTATCCAA
>1803247     ATTGCCATTA AAAGTATAGA TAAAAGCAAT TTGACATCAA AAGTATCCAA
Consensus    ATTGCCATTA AAAGTATAGA TAAAAGCAAT TTGACATCAA AAGTATCCAA >774134IH    CATTGCACAA GTAACTTTGT TTATCCCTCA AGCAAATCCT GATGACATTG
>774419IH    CATTGCACAA GTAACTTTGT TTATCCCTCA AGCAAATCCT GATGACATTG
>2771475     CATTGCACAA GTAACTTTGT TTATCCCTCA AGCAAATCCT GATGACATTG
>1803247     CATTGCACAA GTAACTTTGT TTATCCCTCA AGCAAATCCT GATGACATTG
Consensus    CATTGCACAA GTAACTTTGT TTATCCCTCA AGCAAATCCT GATGACATTG >774134IH    ATCCTACTCC TACTCCTACT CCTACTCCTG ATAAAAGTCA TAATTCTGGA
>774419IH    ATCCTACTCC TACTCCTACT CCTACTCCTG ATAAAAGTCA TAATTCTGGA
>1803247     ATCCTACTCC TACTCCTACT CCTACTCCTG ATAAAAGTCA TAATTCTGGA
>1737526                CTCCTACT CCTACTCCTG ATAAAAGTCA TAATTCTGGA
Consensus    ATCCTACTCC TACTCCTACT CCTACTCCTG ATAAAAGTCA TAATTCTGGA >774134IH    GTTAATATTT CTACGCTGGT ATTGTCTGTG ATTGGGTCTG TTGTAATTGT
>774419IH    GTTAATATTT CTACGCTGGT ATTGTCTGTG ATTGGGTCTG TTGTAATTGT
>1803247     GTTAATATTT CTACGCTGGT ATTGTCTGTG ATTGGG
>1737526     GTTAATATTT CTACGCTGGT ATTGTCTGTG ATTGGGTCTG TTGTAATTGT
>2792957                                           TCTG TTGTAATTGT
Consensus    GTTAATATTT CTACGCTGGT ATTGTCTGTG ATTGGGTCTG TTGTAATTGT >774134IH    TAACTTTATT TTAAGTACCA CCATTTGAAC CTTAACGAAG AAAAAAATCT
>774419IH    TAACTTTATT TTAAGTACCA CCATTTGAAC CTTAACGAAG AAAAAAATCT
>1737526     TAACTTTATT TTAAGTACCA CCATTTGAAC CTTAACGAAG AAAAAAATCT
>2792957     TAACTTTATT TTAAGTACCA CCATTTGAAC CTTAACGAAG AAAAAAATCT
>1226186                                                G AAAAAAATCT
Consensus    TAACTTTATT TTAAGTACCA CCATTTGAAC CTTAACGAAG AAAAAAATCT >774134IH    TCAAGTAGAC CTAGAAGAGA GTTTTAAAAA ACAAAACAAT GTAAGTAAAG
>774419IH    TCAACTAGAC CTACAAGACA GTTTTAAAAA ACAAAACAAT GTAAGTAAAG
>1737526     TCAAGTAGAC CTAGAAGAGA GTTTTAAAAA ACAAAACAAT GTAAGTAAAG
>2792957     TCAAGTAGAC CTAGAAGAGA GTTTTAAAAA ACAAAACAAT GTAAGTNAAG
>1226186     TCAAGTAGAC CTAGAAGAGA GTTTTAAAAA ACAAAACAAT GTAAGTAAAG
Consensus    TCAAGTAGAC CTAGAAGAGA GTTTTAAAAA ACAAAACAAT GTAAGTAAAG >774134IH    GATATTTCTG AATCTTAAAA TTCATCCCAT GTGTGATCAT AAACTCATAA
>774419IH    GATATTTCTG AATCTTAAAA TTCATCCCAT GTGTGATCAT AAACTCATAA
>1737526     GATATTTCTG AAT
>2792957     GATATTTCTG AATCTTAAAA TTCATCCCAT GTGTGATCAT AAACTCATAA
>1226186     CATATTTCTG AATCTTAAAA TTCATCCCAT GTGTGATCAT AAACTCATAA
Consensus    GATATTTCTG AATCTTAAAA TTCATCCCAT GTGTGATCAT AAACTCATAA
```

FIG. 1F

```
>774134IH    AAATAATTTT AAGATGTCGG AAAAGGATAC TTTGATTAAA TAAAAACACT
>774419IH    AAATAATTTT AAGATGTCGG AAAAGGATAC TTTGATTAAA TAAAAACACT
>2792957     AAATAATTTT AAGATGTCGG AAAAGGATAC TTTGATTAAA TAAAAACACT
>1226186     AAATAATTTT AAGATGTCGG AAAAGGATAC TTTGATTAAA TAAAAACACT
Consensus    AAATAATTTT AAGATGTCGG AAAAGGATAC TTTGATTAAA TAAAAACACT >774134IH    CATGGATATG TAAAAACTGT CAAGATTAAA ATTTAATAGT TTCATTTATT
>774419IH    CATGGATATG TAAAAACTGT CAAGATTAAA ATTTAATAGT TTCATTTATT
>2792957     CATGGATATG TAAAAACTGT CAAGATTAAN ATTTAATAGT TTCATTTATT
>1226186     CATGGATATG TAAAAACTGT CAAGATTAAA ATTTAATAGT TTCATTTATT
Consensus    CATGGATATG TAAAAACTGT CAAGATTAAA ATTTAATAGT TTCATTTATT >774134IH    TGTTAITTTA TTTGTAAGAA ATAGTGATGA ACAAAGATCC TTTTTCATAC
>774419IH    TGTTATTTTA TTTGTAAGAA ATAGTGATGA ACAAAGATCC TTTTTCATAC
>2792957     TGTTATTTTA TTTGTAAGAN ATAGTGATGA ACAAAGA
>1226186     TGTTATTTTA TTTGTAAG
Consensus    TGTTATTTTA TTTGTAAGAA ATAGTGATGA ACAAAGATCC TTTTTCATAC >774134IH    TGAT
>774419IH    TGATACCTGG TTGTATATTA TTTGATGCAA CAGTTTTCTC AAATGATATT
Consensus    TGATACCTGG TTGTATATTA TTTGATGCAA CAGTTTTCTG AAATGATATT >774419IH    TCAAATTGCA TCAAGAAATT AAAATCATCT ATCTGAGTAG TCAAAATACA
Consensus    TCAAATTGCA TCAAGAAATT AAAATCATCT ATCTGAGTAG TCAAAATACA >774419IH    AGTAAAGGAG AGCAAATAAA CAACATTTGG A
Consensus    AGTAAAGGAG AGCAAATAAA CAACATTTGG A
```

FIG.1G

SEQUENCE LISTING (1) GENERAL INFORMATION:

(iii) NUMBER OF SEQUENCES: 51

(2) INFORMATION FOR SEQ ID NO:1:

(i) SEQUENCE CHARACTERISTICS:
       (A) LENGTH: 241 base pairs
       (B) TYPE: nucleic acid
       (C) STRANDEDNESS: single
       (D) TOPOLOGY: linear (xi) SEQUENCE DESCRIPTION: SEQ ID NO:1:

```
GCCAGGAATA ACTAGAGAGG AACAATGGGG TTATTCAGAG GTTTTGTTTT CCTCTTAGTT      60

CTGTGCCTGC TGCACCAGTC AAATACTTCC TTCATTAAGC TGAATAATAA TGGCTTTGAA     120

GATATTGTCA TTGTTATAGA TCCTAGTGTG CCAGAAGATG AAAAAATAAT TGAACAAATA     180

GAGGATATGG TGACTACAGC TTCTACGTAC CTGTTTGAAG CCACAGAAAA AAGATTTTTT     240

T                                                                    241
```

(2) INFORMATION FOR SEQ ID NO:2:

(i) SEQUENCE CHARACTERISTICS:
       (A) LENGTH: 219 base pairs
       (B) TYPE: nucleic acid
       (C) STRANDEDNESS: single
       (D) TOPOLOGY: linear (xi) SEQUENCE DESCRIPTION: SEQ ID NO:2:

```
CTAGAGAGGA ACAATGGGGT TATTCAGAGG TTTTGTTTTC CTCTTAGTTC TGTGCCTGCT      60

GCACCAGTCA AATACTTCCT TCATTAAGCT GAATAATAAT GGCTTTGAAG ATATTGTCAT     120

TGTTATAGAT CCTAGTGTGC CAGAAGATGA AAAAATAATT GAACAAATAG AGGATATGGT     180

GACTACAGCT TCTACGTACC TGTTTGAAGC CACAGAAAA                            219
```

(2) INFORMATION FOR SEQ ID NO:3:

(i) SEQUENCE CHARACTERISTICS:
       (A) LENGTH: 231 base pairs
       (B) TYPE: nucleic acid
       (C) STRANDEDNESS: single
       (D) TOPOLOGY: linear (ix) FEATURE:
       (A) NAME/KEY: base_polymorphism
       (B) LOCATION: 3
       (D) OTHER INFORMATION: /note= " N' represents an A or G or
           T or C polymorphism at this position"

(xi) SEQUENCE DESCRIPTION: SEQ ID NO:3:

```
TTNTGTAACG AAAAAACCCA TAATCAAGAA GCTCCAAGCC TACAAAACAT AAAGTGCAAT      60

TTTAGAAGTA CATGGGAGGT GATTAGCAAT TCTGAGGATT TTAAAAACAC CATACCCATG     120

GTGACACCAC CTCCTCCACC TGTCTTCTCA TTGCTGAAGA TCAGTCAAAG AATTGTGTGC     180

TTAGTTCTTG ATAAGTCTGG AAGCATGGGG GGTAAGGACC GCCTAAATCG A              231
```

(2) INFORMATION FOR SEQ ID NO:4:

(i) SEQUENCE CHARACTERISTICS:
       (A) LENGTH: 237 base pairs
       (B) TYPE: nucleic acid

```
        (C) STRANDEDNESS: single
        (D) TOPOLOGY: linear (xi) SEQUENCE DESCRIPTION: SEQ ID NO:4:

TGGGGGGTAA GGACCGCCTA AATCGAATGA ATCAAGCAGC AAAACATTTC CTGCTGCAGA        60

CTGTTGAAAA TGGATCCTGG GTGGGGATGG TTCACTTTGA TAGTACTGCC ACTATTGTAA       120

ATAAGCTAAT CCAAATAAAA AGCAGTGATG AAAGAAACAC ACTCATGGCA GGATTACCTA       180

CATATCCTCT GGGAGGAACT TCCATCTGCT CTGGAATTAA ATATGCATTT CAGGTGA          237

(2) INFORMATION FOR SEQ ID NO:5:

(i) SEQUENCE CHARACTERISTICS:
        (A) LENGTH: 216 base pairs
        (B) TYPE: nucleic acid
        (C) STRANDEDNESS: single
        (D) TOPOLOGY: linear (xi) SEQUENCE DESCRIPTION: SEQ ID NO:5:

CTTCCATCTG CTCTGGAATT AAATATGCAT TCAGGTGAT TGGAGAGCTA CATTCCCAAC         60

TCGATGGATC CGAAGTACTG CTGCTGACTG ATGGGGAGGA TAACACTGCA AGTTCTTGTA      120

TTGATGAAGT GAAACAAAGT GGGGCCATTG TTCATTTTAT TGCTTTGGGA AGAGCTGCTG      180

ATGAAGCAGT AATAGAGATG AGCAAGATAA CAGGAG                                 216

(2) INFORMATION FOR SEQ ID NO:6:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (ix) FEATURE:
        (A) NAME/KEY: base_polymorphism
        (B) LOCATION: 24
        (D) OTHER INFORMATION: /note= " N' represents an A or G or
            T or C polymorphism at this position"

(xi) SEQUENCE DESCRIPTION: SEQ ID NO:6:

AATTGATAGT ACAGTGGGAA AGGNCACGTT CTTTCTCATC ACATGGAACA GTCTGCCTCC        60

CAGTATTTCT CTCTGGGATC CCAGTGGAAC AATAATGGAA AATTTCACAG TGGATGCAAC      120

TTCCAAAATG GCCTATCTCA GTATTCCAGG AACTGCAAAG GTGGGCACTT GGGCATACAA      180

TCTTCAAGCC AAAGCGAACC C                                                 201

(2) INFORMATION FOR SEQ ID NO:7:

(i) SEQUENCE CHARACTERISTICS:
        (A) LENGTH: 241 base pairs
        (B) TYPE: nucleic acid
        (C) STRANDEDNESS: single
        (D) TOPOLOGY: linear (xi) SEQUENCE DESCRIPTION: SEQ ID NO:7:

GCAAATTCTT CTGTGCCTCC AATCACAGTG AATGCTAAAA TGAATAAGGA CGTAAACAGT        60

TTCCCCAGCC CAATGATTGT TTACGCAGAA ATTCTACAAG GATATGTACC TGTTCTTGGA      120

GCCAATGTGA CTGCTTTCAT TGAATCACAG AATGGACATA CAGAAGTTTT GGAACTTTTG      180

GATAATGGTG CAGGCGCTGA TTCTTTCAAG AATGATGGAG TCTACTCCAG GTATTTTACA      240

G                                                                       241
```

(2) INFORMATION FOR SEQ ID NO:8:

(i) SEQUENCE CHARACTERISTICS:
        (A) LENGTH: 242 base pairs
        (B) TYPE: nucleic acid
        (C) STRANDEDNESS: single
        (D) TOPOLOGY: linear (xi) SEQUENCE DESCRIPTION: SEQ ID NO:8:

```
GTGCAGGCGC TGATTCTTTC AAGAATGATG GAGTCTACTC CAGGTATTTT ACAGCATATA      60

CAGAAAATGG CAGATATAGC TTAAAAGTTC GGGCTCATGG AGGAGCAAAC ACTGCCAGGC     120

TAAAATTACG GCCTCCACTG AATAGAGCCG CGTACATACC AGGCTGGGTA GTGAACGGGG     180

AAATTGAAGC AAACCCGCCA AGACCTGAAA TTGATGAGGA TACTCAGACC ACCTTGGAGG     240

AT                                                                    242
```

(2) INFORMATION FOR SEQ ID NO:9:

(i) SEQUENCE CHARACTERISTICS:
        (A) LENGTH: 233 base pairs
        (B) TYPE: nucleic acid
        (C) STRANDEDNESS: single
        (D) TOPOLOGY: linear (xi) SEQUENCE DESCRIPTION: SEQ ID NO:9:

```
CCCGCCAAGA CCTGAAATTG ATGAGGATAC TCAGACCACC TTGGAGGATT TCAGCCGAAC      60

AGCATCCGGA GGTGCATTTG TGGTATCACA AGTCCCAAGC CTTCCCTTGC CTGACCAATA     120

CCCACCAAGT CAAATCACAG ACCTTGATGC CACAGTTCAT GAGGATAAGA TTATTCTTAC     180

ATGGACAGCA CCAGGAGATA ATTTTGATGT TGGAAAAGTT CAACGTTATA TCA           233
```

(2) INFORMATION FOR SEQ ID NO:10:

(i) SEQUENCE CHARACTERISTICS:
        (A) LENGTH: 313 base pairs
        (B) TYPE: nucleic acid
        (C) STRANDEDNESS: single
        (D) TOPOLOGY: linear (ix) FEATURE:
        (A) NAME/KEY: base_polymorphism
        (B) LOCATION: 22
        (D) OTHER INFORMATION: /note= " N' represents an A or G or
            T or C polymorphism at this position"

(ix) FEATURE:
        (A) NAME/KEY: base_polymorphism
        (B) LOCATION: 44
        (D) OTHER INFORMATION: /note= " N' represents an A or G or
            T or C polymorphism at this position"

(xi) SEQUENCE DESCRIPTION: SEQ ID NO:10:

```
CCAATACCCA CCAAGTCAAA TNACAGACCT TGATGCCACA GTTNATGAGG ATAAGATTAT      60

TCTTACATGG ACAGCACCAG GAGATAATTT TGATGTTGGA AAAGTTCAAC GTTATATCAT     120

AAGAATAAGT GCAAGTATTC TTGATCTAAG AGACAGTTTT GATGATGCTC TTCAAGTAAA     180

TACTACTGAT CTGTCACCAA AGGAGGCCAA CTCCAAGGAA AGCTTTGCAT TTAAACCAGA     240

AAATATCTCA GAAGAAAATG CAACCCACAT ATTTATTGCC ATTAAAGTA TAGATAAAGC      300

ATTTGGCATC AAA                                                        313
```

(2) INFORMATION FOR SEQ ID NO:11:

(i) SEQUENCE CHARACTERISTICS:
        (A) LENGTH: 242 base pairs

```
        (B) TYPE: nucleic acid
        (C) STRANDEDNESS: single
        (D) TOPOLOGY: linear (xi) SEQUENCE DESCRIPTION: SEQ ID NO:11:

AAGTATTCTT GATCTAAGAG ACAGTTTTGA TGATGCTCTT CAAGTAAATA CTACTGATCT      60

GTCACCAAAG GAGGCCAACT CCAAGGAAAG CTTTGCATTT AAACCAGAAA ATATCTCAGA     120

AGAAAATGCA ACCCACATAT TTATTGCCAT TAAAAGTATA GATAAAAGCA ATTTGACATC     180

AAAAGTATCC AACATTGCAC AAGTAACTTT GTTTATCCCT CAAGCAAATC CTGATGACAT     240

TG                                                                    242

(2) INFORMATION FOR SEQ ID NO:12:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (ix) FEATURE:
        (A) NAME/KEY: base_polymorphism
        (B) LOCATION: 2
        (D) OTHER INFORMATION: /note= " N' represents an A or G or
            T or C polymorphism at this position"

(ix) FEATURE:
        (A) NAME/KEY: base_polymorphism
        (B) LOCATION: 4
        (D) OTHER INFORMATION: /note= " N' represents an A or G or
            T or C polymorphism at this position"

(xi) SEQUENCE DESCRIPTION: SEQ ID NO:12:

ANANAATGCA ACCCACATAT TTATTGCCAT TAAAAGTATA GATAAAAGCA ATTTGACATC      60

AAAAGTATCC AACATTGCAC AAGTAACTTT GTTTATCCCT CAAGCAAATC CTGATGACAT     120

TGATCCTACT CCTACTCCTA CTCCTACTCC TGATAAAAGT CATAATTCTG GAGTTAATAT     180

TTCTACGCTG GTATTGTCTG TGATTGGG                                        208

(2) INFORMATION FOR SEQ ID NO:13:

(i) SEQUENCE CHARACTERISTICS:
        (A) LENGTH: 201 base pairs
        (B) TYPE: nucleic acid
        (C) STRANDEDNESS: single
        (D) TOPOLOGY: linear (xi) SEQUENCE DESCRIPTION: SEQ ID NO:13:

CTCCTACTCC TACTCCTGAT AAAAGTCATA ATTCTGGAGT TAATATTTCT ACGCTGGTAT      60

TGTCTGTGAT TGGGTCTGTT GTAATTGTTA ACTTTATTTT AAGTACCACC ATTTGAACCT     120

TAACGAAGAA AAAAATCTTC AAGTAGACCT AGAAGAGAGT TTTAAAAAAC AAAACAATGT     180

AAGTAAAGGA TATTTCTGAA T                                               201

(2) INFORMATION FOR SEQ ID NO:14:

(i) SEQUENCE CHARACTERISTICS:
        (A) LENGTH: 301 base pairs
        (B) TYPE: nucleic acid
        (C) STRANDEDNESS: single
        (D) TOPOLOGY: linear (ix) FEATURE:
        (A) NAME/KEY: base_polymorphism
        (B) LOCATION: 111
        (D) OTHER INFORMATION: /note= " N' represents an A or G or
```

```
           T or C polymorphism at this position"

(ix) FEATURE:
      (A) NAME/KEY: base_polymorphism
      (B) LOCATION: 244
      (D) OTHER INFORMATION: /note= " N' represents an A or G or
          T or C polymorphism at this position"

(ix) FEATURE:
      (A) NAME/KEY: base_polymorphism
      (B) LOCATION: 284
      (D) OTHER INFORMATION: /note= " N' represents an A or G or
          T or C polymorphism at this position"

(xi) SEQUENCE DESCRIPTION: SEQ ID NO:14:

TCTGTTGTAA TTGTTAACTT TATTTTAAGT ACCACCATTT GAACCTTAAC GAAGAAAAAA      60

ATCTTCAAGT AGACCTAGAA GAGAGTTTTA AAAAACAAAA CAATGTAAGT NAAGGATATT    120

TCTGAATCTT AAAATTCATC CCATGTGTGA TCATAAACTC ATAAAAATAA TTTTAAGATG    180

TCGGAAAAGG ATACTTTGAT TAAATAAAAA CACTCATGGA TATGTAAAAA CTGTCAAGAT    240

TAANATTTAA TAGTTTCATT TATTTGTTAT TTTATTTGTA AGANATAGTG ATGAACAAAG    300

A                                                                    301

(2) INFORMATION FOR SEQ ID NO:15:

(i) SEQUENCE CHARACTERISTICS:
        (A) LENGTH: 229 base pairs
        (B) TYPE: nucleic acid
        (C) STRANDEDNESS: single
        (D) TOPOLOGY: linear (xi) SEQUENCE DESCRIPTION: SEQ ID NO:15:

GAAAAAAATC TTCAAGTAGA CCTAGAAGAG AGTTTTAAAA AACAAAACAA TGTAAGTAAA     60

GGATATTTCT GAATCTTAAA ATTCATCCCA TGTGTGATCA TAAACTCATA AAAATAATTT    120

TAAGATGTCG GAAAAGGATA CTTTGATTAA ATAAAAACAC TCATGGATAT GTAAAAACTG    180

TCAAGATTAA AATTTAATAG TTTCATTTAT TTGTTATTTT ATTTGTAAG               229

(2) INFORMATION FOR SEQ ID NO:16:

(i) SEQUENCE CHARACTERISTICS:
        (A) LENGTH: 3043 base pairs
        (B) TYPE: nucleic acid
        (C) STRANDEDNESS: single
        (D) TOPOLOGY: linear (xi) SEQUENCE DESCRIPTION: SEQ ID NO:16:

CTAGAGAGGA ACAATGGGGT TATTCAGAGG TTTTGTTTTC CTCTTAGTTC TGTGCCTGCT     60

GCACCAGTCA AATACTTCCT TCATTAAGCT GAATAATAAT GGCTTTGAAG ATATTGTCAT    120

TGTTATAGAT CCTAGTGTGC CAGAAGATGA AAAAATAATT GAACAAATAG AGGATATGGT    180

GACTACAGCT TCTACGTACC TGTTTGAAGC CACAGAAAAA AGATTTTTTT TCAAAAATGT    240

ATCTATATTA ATTCCTGAGA ATTGGAAGGA AAATCCTCAG TACAAAAGGC CAAAACATGA    300

AAACCATAAA CATGCTGATG TTATAGTTGC ACCACCTACA CTCCCAGGTA GAGATGAACC    360

ATACACCAAG CAGTTCACAG AATGTGGAGA GAAAGGCGAA TACATTCACT TCACCCCTGA    420

CCTTCTACTT GAAAAAAAAC AAAATGAATA TGGACCACCA GGCAAACTGT TGTCCATGA    480

GTGGGCTCAC CTCCGGTGGG GAGTGTTTGA TGAGTACAAT GAAGATCAGC CTTTCTACCG    540

TGCTAAGTCA AAAAAAATCG AAGCAACAAG GTGTTCCGCA GGTATCTCTG GTAGAAATAG    600

AGTTTATAAG TGTCAAGGAG GCAGCTGTCT TAGTAGAGCA TGCAGAATTG ATTCTACAAC    660
```

```
AAAACTGTAT GGAAAAGATT GTCAATTCTT TCCTGATAAA GTACAAACAG AAAAAGCATC    720

CATAATGTTT ATGCAAAGTA TTGATTCTGT TGTTGAATTT TGTAACGAAA AAACCCATAA    780

TCAAGAAGCT CCAAGCCTAC AAAACATAAA GTGCAATTTT AGAAGTACAT GGGAGGTGAT    840

TAGCAATTCT GAGGATTTTA AAAACACCAT ACCCATGGTG ACACCACCTC CTCCACCTGT    900

CTTCTCATTG CTGAAGATCA GTCAAAGAAT TGTGTGCTTA GTTCTTGATA AGTCTGGAAG    960

CATGGGGGT AAGGACCGCC TAAATCGAAT GAATCAAGCA GCAAAACATT TCCTGCTGC    1020

GACTGTTGAA AATGGATCCT GGGTGGGGAT GGTTCACTTT GATAGTACTG CCACTATTG    1080

AAATAAGCTA ATCCAAATAA AAAGCAGTGA TGAAAGAAAC ACACTCATGG CAGGATTAC    1140

TACATATCCT CTGGGAGGAA CTTCCATCTG CTCTGGAATT AAATATGCAT TTCAGGTGA    1200

TGGAGAGCTA CATTCCCAAC TCGATGGATC CGAAGTACTG CTGCTGACTG ATGGGGAGG    1260

TAACACTGCA AGTTCTTGTA TTGATGAAGT GAAACAAAGT GGGGCCATTG TTCATTTTA    1320

TGCTTTGGGA AGAGCTGCTG ATGAAGCAGT AATAGAGATG AGCAAGATAA CAGGAGGAA    1380

TCATTTTTAT GTTTCAGATG AAGCTCAGAA CAATGGCCTC ATTGATGCTT TTGGGGCTC    1440

TACATCAGGA AATACTGATC TCTCCCAGAA GTCCCTTCAG CTCGAAAGTA AGGGATTAA    1500

ACTGAATAGT AATGCCTGGA TGAACACAC TGTCATAATT GATAGTACAG TGGGAAAGG    1560

CACGTTCTTT CTCATCACAT GGAACAGTCT GCCTCCCAGT ATTTCTCTCT GGGATCCCA    1620

TGGAACAATA ATGGAAAATT TCACAGTGGA TGCAACTTCC AAAATGGCCT ATCTCAGTA    1680

TCCAGGAACT GCAAAGGTGG GCACTTGGGC ATACAATCTT CAAGCCAAAG CGAACCCAG    1740

AACATTAACT ATTACAGTAA CTTCTCGAGC AGCAAATTCT TCTGTGCCTC CAATCACAG    1800

GAATGCTAAA ATGAATAAGG ACGTAAACAG TTTCCCCAGC CCAATGATTG TTTACGCAG    1860

AATTCTACAA GGATATGTAC CTGTTCTTGG AGCCAATGTG ACTGCTTTCA TTGAATCAC    1920

GAATGGACAT ACAGAAGTTT TGGAACTTTT GGATAATGGT GCAGGCGCTG ATTCTTTCA    1980

GAATGATGGA GTCTACTCCA GGTATTTTAC AGCATATACA GAAAATGGCA GATATAGCT    2040

AAAAGTTCGG GCTCATGGAG GAGCAAACAC TGCCAGGCTA AAATTACGGC CTCCACTGA    2100

TAGAGCCGCG TACATACCAG GCTGGGTAGT GAACGGGGAA ATTGAAGCAA ACCCGCCAA    2160

ACCTGAAATT GATGAGGATA CTCAGACCAC CTTGGAGGAT TTCAGCCGAA CAGCATCCG    2220

AGGTGCATTT GTGGTATCAC AAGTCCCAAG CCTTCCCTTG CCTGACCAAT ACCCACCAA    2280

TCAAATCACA GACCTTGATG CCACAGTTCA TGAGGATAAG ATTATTCTTA CATGGACAG    2340

ACCAGGAGAT AATTTTGATG TTGGAAAAGT TCAACGTTAT ATCATAAGAA TAAGTGCAA    2400

TATTCTTGAT CTAAGAGACA GTTTTGATGA TGCTCTTCAA GTAAATACTA CTGATCTGT    2460

ACCAAAGGAG GCCAACTCCA AGGAAAGCTT TGCATTTAAA CCAGAAAATA TCTCAGAAG    2520

AAATGCAACC CACATATTTA TTGCCATTAA AAGTATAGAT AAAAGCAATT TGACATCAA    2580

AGTATCCAAC ATTGCACAAG TAACTTTGTT TATCCCTCAA GCAAATCCTG ATGACATTG    2640

TCCTACTCCT ACTCCTACTC CTACTCCTGA TAAAAGTCAT AATTCTGGAG TTAATATTT    2700

TACGCTGGTA TTGTCTGTGA TTGGGTCTGT TGTAATTGTT AACTTTATTT AAGTACCA    2760

CATTTGAACC TTAACGAAGA AAAAAATCTT CAAGTAGACC TAGAAGAGAG TTTTAAAAA    2820

CAAAACAATG TAAGTAAAGG ATATTTCTGA ATCTTAAAAT TCATCCCATG TGTGATCAT    2880

AACTCATAAA AATAATTTTA AGATGTCGGA AAAGGATACT TTGATTAAAT AAAAACACT    2940

ATGGATATGT AAAAACTGTC AAGATTAAAA TTTAATAGTT TCATTTATTT GTTATTTTA    3000
```

```
TTGTAAGAAA TAGTGATGAA CAAAGATCCT TTTTCATACT GAT              3043
```

(2) INFORMATION FOR SEQ ID NO:17:

(i) SEQUENCE CHARACTERISTICS:
        (A) LENGTH: 1399 base pairs
        (B) TYPE: nucleic acid
        (C) STRANDEDNESS: single
        (D) TOPOLOGY: linear (xi) SEQUENCE DESCRIPTION: SEQ ID NO:17:

```
GCAAATTCTT CTGTGCCTCC AATCACAGTG AATGCTAAAA TGAATAAGGA CGTAAACAGT    60
TTCCCCAGCC CAATGATTGT TTACGCAGAA ATTCTACAAG GATATGTACC TGTTCTTGGA   120
GCCAATGTGA CTGCTTTCAT TGAATCACAG AATGGACATA CAGAAGTTTT GGAACTTTTG   180
GATAATGGTG CAGGCGCTGA TTCTTTCAAG AATGATGGAG TCTACTCCAG GTATTTACA    240
GCATATACAG AAAATGGCAG ATATAGCTTA AAAGTTCGGG CTCATGGAGG AGCAAACACT   300
GCCAGGCTAA AATTACGGCC TCCACTGAAT AGAGCCGCGT ACATACCAGG CTGGGTAGTG   360
AACGGGGAAA TTGAAGCAAA CCCGCCAAGA CCTGAAATTG ATGAGGATAC TCAGACCACC   420
TTGGAGGATT TCAGCCGAAC AGCATCCGGA GGTGCATTTG TGGTATCACA AGTCCCAAGC   480
CTTCCCTTGC CTGACCAATA CCCACCAAGT CAAATCACAG ACCTTGATGC CACAGTTCAT   540
GAGGATAAGA TTATTCTTAC ATGGACAGCA CCAGGAGATA ATTTTGATGT TGGAAAAGTT   600
CAACGTTATA TCATAAGAAT AAGTGCAAGT ATTCTTGATC TAAGAGACAG TTTTGATGAT   660
GCTCTTCAAG TAAATACTAC TGATCTGTCA CCAAAGGAGG CCAACTCCAA GGAAAGCTTT   720
GCATTTAAAC CAGAAAATAT CTCAGAAGAA AATGCAACCC ACATATTTAT TGCCATTAAA   780
AGTATAGATA AAGCAATTT GACATCAAAA GTATCCAACA TTGCACAAGT AACTTTGTTT    840
ATCCCTCAAG CAAATCCTGA TGACATTGAT CCTACTCCTA CTCCTACTCC TACTCCTGAT   900
AAAAGTCATA ATTCTGGAGT TAATATTTCT ACGCTGGTAT TGTCTGTGAT TGGGTCTGTT   960
GTAATTGTTA ACTTTATTTT AAGTACCACC ATTTGAACCT TAACGAAGAA AAAAATCTT   1020
AAGTAGACCT AGAAGAGAGT TTTAAAAAAC AAAACAATGT AAGTAAAGGA TATTTCTGA   1080
TCTTAAAATT CATCCCATGT GTGATCATAA ACTCATAAAA ATAATTTTAA GATGTCGGA   1140
AAGGATACTT TGATTAAATA AAAACACTCA TGGATATGTA AAAACTGTCA AGATTAAAA   1200
TTAATAGTTT CATTTATTTG TTATTTTATT TGTAAGAAAT AGTGATGAAC AAAGATCCT   1260
TTTCATACTG ATACCTGGTT GTATATTATT TGATGCAACA GTTTTCTGAA ATGATATTT   1320
AAATTGCATC AAGAAATTAA AATCATCTAT CTGAGTAGTC AAAATACAAG TAAAGGAGA   1380
CAAATAAACA ACATTTGGA                                              1399
```

(2) INFORMATION FOR SEQ ID NO:18:

(i) SEQUENCE CHARACTERISTICS:
        (A) LENGTH: 3181 base pairs
        (B) TYPE: nucleic acid
        (C) STRANDEDNESS: single
        (D) TOPOLOGY: linear (xi) SEQUENCE DESCRIPTION: SEQ ID NO:18:

```
GCCAGGAATA ACTAGAGAGG AACAATGGGG TTATTCAGAG GTTTTGTTTT CCTCTTAGTT    60
CTGTGCCTGC TGCACCAGTC AAATACTTCC TTCATTAAGC TGAATAATAA TGGCTTTGAA   120
GATATTGTCA TTGTTATAGA TCCTAGTGTG CCAGAAGATG AAAAAAATAAT TGAACAAATA   180
GAGGATATGG TGACTACAGC TTCTACGTAC CTGTTTGAAG CCACAGAAAA AAGATTTTTT   240
```

-continued

```
TTCAAAAATG TATCTATATT AATTCCTGAG AATTGGAAGG AAAATCCTCA GTACAAAAGG      300

CCAAAACATG AAAACCATAA ACATGCTGAT GTTATAGTTG CACCACCTAC ACTCCCAGGT      360

AGAGATGAAC CATACACCAA GCAGTTCACA GAATGTGGAG AGAAAGGCGA ATACATTCAC      420

TTCACCCCTG ACCTTCTACT TGAAAAAAAA CAAAATGAAT ATGGACCACC AGGCAAACTG      480

TTTGTCCATG AGTGGGCTCA CCTCCGGTGG GGAGTGTTTG ATGAGTACAA TGAAGATCAG      540

CCTTTCTACC GTGCTAAGTC AAAAAAAATC GAAGCAACAA GGTGTTCCGC AGGTATCTCT      600

GGTAGAAATA GAGTTTATAA GTGTCAAGGA GGCAGCTGTC TTAGTAGAGC ATGCAGAATT      660

GATTCTACAA CAAAACTGTA TGGAAAAGAT TGTCAATTCT TTCCTGATAA AGTACAAACA      720

GAAAAAGCAT CCATAATGTT TATGCAAAGT ATTGATTCTG TTGTTGAATT TTGTAACGAA      780

AAAACCCATA ATCAAGAAGC TCCAAGCCTA CAAAACATAA AGTGCAATTT TAGAAGTACA      840

TGGGAGGTGA TTAGCAATTC TGAGGATTTT AAAAACACCA TACCCATGGT GACACCACCT      900

CCTCCACCTG TCTTCTCATT GCTGAAGATC AGTCAAAGAA TTGTGTGCTT AGTTCTTGAT      960

AAGTCTGGAA GCATGGGGGG TAAGGACCGC CTAAATCGAA TGAATCAAGC AGCAAAACA     1020

TTCCTGCTGC AGACTGTTGA AAATGGATCC TGGGTGGGGA TGGTTCACTT TGATAGTAC     1080

GCCACTATTG TAAATAAGCT AATCCAAATA AAAAGCAGTG ATGAAAGAAA CACACTCAT     1140

GCAGGATTAC CTACATATCC TCTGGGAGGA ACTTCCATCT GCTCTGGAAT TAAATATGC     1200

TTTCAGGTGA TTGGAGAGCT ACATTCCCAA CTCGATGGAT CCGAAGTACT GCTGCTGAC     1260

GATGGGGAGG ATAACACTGC AAGTTCTTGT ATTGATGAAG TGAAACAAAG TGGGGCCAT     1320

GTTCATTTTA TTGCTTTGGG AAGAGCTGCT GATGAAGCAG TAATAGAGAT GAGCAAGAT     1380

ACAGGAGGAA GTCATTTTTA TGTTTCAGAT GAAGCTCAGA ACAATGGCCT CATTGATGC     1440

TTTGGGGCTC TTACATCAGG AAATACTGAT CTCTCCCAGA AGTCCCTTCA GCTCAAAAG     1500

AAGGGATTAA CACTGAATAG TAATGCCTGG ATGAACGACA CTGTCATAAT TGATAGTAC     1560

GTGGGAAAGG ACACGTTCTT TCTCATCACA TGGAACAGTC TGCCTCCCAG TATTTCTCT     1620

TGGGATCCCA GTGGAACAAT AATGGAAAAT TTCACAGTGG ATGCAACTTC CAAAATGGC     1680

TATCTCAGTA TTCCAGGAAC TGCAAAGGTG GGCACTTGGG CATACAATCT TCAAGCCAA     1740

GCGAACCCAG AAACATTAAC TATTACAGTA ACTTCTCGAG CAGCAAATTC TTCTGTGCC     1800

CCAATCACAG TGAATGCTAA AATGAATAAG GACGTAAACA GTTTCCCCAG CCCAATGAT     1860

GTTTACGCAG AAATTCTACA AGGATATGTA CCTGTTCTTG GAGCCAATGT GACTGCTTT     1920

ATTGAATCAC AGAATGGACA TACAGAAGTT TTGGAACTTT TGGATAATGG TGCAGGCGC     1980

GATTCTTTCA AGAATGATGG AGTCTACTCC AGGTATTTTA CAGCATATAC AGAAAATGG     2040

AGATATAGCT TAAAAGTTCG GGCTCATGGA GGAGCAAACA CTGCCAGGCT AAAAATTACG     2100

CCTCCACTGA ATAGAGCCGC GTACATACCA GGCTGGGTAG TGAACGGGGA AATTGAAGC     2160

AACCCGCCAA GACCTGAAAT TGATGAGGAT ACTCAGACCA CCTTGGAGGA TTTCAGCCG     2220

ACAGCATCCG GAGGTGCATT TGTGGTATCA CAAGTCCCAA GCCTTCCCTT GCCTGACCA     2280

TACCCACCAA GTCAAATCAC AGACCTTGAT GCCACAGTTC ATGAGGATAA GATTATTCT     2340

ACATGGACAG CACCAGGAGA TAATTTTGAT GTTGGAAAAG TTCAACGTTA TATCATAAG     2400

ATAAGTGCAA GTATTCTTGA TCTAAGAGAC AGTTTTGATG ATGCTCTTCA AGTAAATAC     2460

ACTGATCTGT CACCAAAGGA GGCCAACTCC AAGGAAAGCT TGCATTTAA ACCAGAAAA     2520

ATCTCAGAAG AAAATGCAAC CCACATATTT ATTGCCATTA AAGTATAGA TAAAAGCAA     2580
```

```
TTGACATCAA AAGTATCCAA CATTGCACAA GTAACTTTGT TTATCCCTCA AGCAAATCC      2640

GATGACATTG ATCCTACTCC TACTCCTACT CCTACTCCTG ATAAAAGTCA TAATTCTGG      2700

GTTAATATTT CTACGCTGGT ATTGTCTGTG ATTGGGTCTG TTGTAATTGT TAACTTTAT      2760

TTAAGTACCA CCATTTGAAC CTTAACGAAG AAAAAAATCT TCAAGTAGAC CTAGAAGAG      2820

GTTTTAAAAA ACAAAACAAT GTAAGTAAAG GATATTTCTG AATCTTAAAA TTCATCCCA      2880

GTGTGATCAT AAACTCATAA AAATAATTTT AAGATGTCGG AAAAGGATAC TTTGATTAA      2940

TAAAAACACT CATGGATATG TAAAAACTGT CAAGATTAAA ATTTAATAGT TTCATTTAT      3000

TGTTATTTTA TTTGTAAGAA ATAGTGATGA ACAAAGATCC TTTTTCATAC TGATACCTG      3060

TTGTATATTA TTTGATGCAA CAGTTTTCTG AAATGATATT TCAAATTGCA TCAAGAAAT      3120

AAAATCATCT ATCTGAGTAG TCAAAATACA AGTAAAGGAG AGCAAATAAA CAACATTTG      3180

A                                                                    3181
```

(2) INFORMATION FOR SEQ ID NO:19:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:19:

```
AGCTCGGAAT TCCGAGCTTG GATCCTCTAG AGCGGCCGCC GACTAGTGAG CTCGTCGACC      60

CGGGAATT                                                              68
```

(2) INFORMATION FOR SEQ ID NO:20:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:20:

```
AATTAATTCC CGGGTCGACG AGCTCACTAG TCGGCGGCCG CTCTAGAGGA TCCAAGCTCG      60

GAATTCCG                                                              68
```

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:21:

```
AGCGGATAAC AATTTCACAC AGGA                                            24
```

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:22:

```
TGTAAAACGA CGGCCAGT                                                   18
```

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:23:

CTGCCAGGCT AAAATTACGG    20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:24:

ATCACAGACC TTGATGCCAC    20

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:25:

GCTGGTATTG TCTGTGATTG GGTC    24

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:26:

CATCAGGATT TGCTTGAGGG    20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:27:

TATTGGTCAG GCAAGGGAAG    20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:28:

GTGTTTGCTC CTCCATGAGC    20

(2) INFORMATION FOR SEQ ID NO:29:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:29:

CAAGTAGAAG GTCAGGGGTG                                                    20

(2) INFORMATION FOR SEQ ID NO:30:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:30:

ATAAGTGTCA AGGAGGCAGC                                                    20

(2) INFORMATION FOR SEQ ID NO:31:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:31:

GCAGACTGTT CCATGTGATG                                                    20

(2) INFORMATION FOR SEQ ID NO:32:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:32:

ATGTACCTGT TCTTGGAGCC                                                    20

(2) INFORMATION FOR SEQ ID NO:33:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:33:

ACGTACCTGT TTGAAGCCAC                                                    20

(2) INFORMATION FOR SEQ ID NO:34:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:34:

GGTAAGGACC GCCTAAATCG                                                    20

(2) INFORMATION FOR SEQ ID NO:35:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:35:

GAAGTGAAAC AAAGTGGGGC                                            20

(2) INFORMATION FOR SEQ ID NO:36:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:36:

TTATCCTCCC CATCAGTCAG                                            20

(2) INFORMATION FOR SEQ ID NO:37:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:37:

TCGATTTAGG CGGTCCTTAC                                            20

(2) INFORMATION FOR SEQ ID NO:38:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:38:

TGTGGCTTCA AACAGGTACG                                            20

(2) INFORMATION FOR SEQ ID NO:39:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (xi) SEQUENCE DESCRIPTION: SEQ ID NO:39:

GGGTAAGGAC CGCCTAAATC GAATG                                      25

(2) INFORMATION FOR SEQ ID NO:40:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (xi) SEQUENCE DESCRIPTION: SEQ ID NO:40:

GAGCCCCAAA AGCATCAATG AGG                                        23

(2) INFORMATION FOR SEQ ID NO:41:

(i) SEQUENCE CHARACTERISTICS:

```
    (A) LENGTH: 917 amino acids
    (B) TYPE: amino acid
    (C) STRANDEDNESS: single
    (D) TOPOLOGY: linear (ii) MOLECULE TYPE: None (xi) SEQUENCE DESCRIPTION: SEQ ID NO:41:

Met Gly Leu Phe Arg Gly Phe Val Phe Leu Leu Val Leu Cys Leu Leu
 1               5                  10                  15

His Gln Ser Asn Thr Ser Phe Ile Lys Leu Asn Asn Asn Gly Phe Glu
            20                  25                  30

Asp Ile Val Ile Val Ile Asp Pro Ser Val Pro Glu Asp Glu Lys Ile
        35                  40                  45

Ile Glu Gln Ile Glu Asp Met Val Thr Thr Ala Ser Thr Tyr Leu Phe
50                  55                  60

Glu Ala Thr Glu Lys Arg Phe Phe Lys Asn Val Ser Ile Leu Ile
65                  70                  75                  80

Pro Glu Asn Trp Lys Glu Asn Pro Gln Tyr Lys Arg Pro Lys His Glu
                85                  90                  95

Asn His Lys His Ala Asp Val Ile Val Ala Pro Pro Thr Leu Pro Gly
            100                 105                 110

Arg Asp Glu Pro Tyr Thr Lys Gln Phe Thr Glu Cys Gly Glu Lys Gly
        115                 120                 125

Glu Tyr Ile His Phe Thr Pro Asp Leu Leu Glu Lys Lys Gln Asn
130                 135                 140

Glu Tyr Gly Pro Pro Gly Lys Leu Phe Val His Glu Trp Ala His Leu
145                 150                 155                 160

Arg Trp Gly Val Phe Asp Glu Tyr Asn Glu Asp Gln Pro Phe Tyr Arg
                165                 170                 175

Ala Lys Ser Lys Lys Ile Glu Ala Thr Arg Cys Ser Ala Gly Ile Ser
            180                 185                 190

Gly Arg Asn Arg Val Tyr Lys Cys Gln Gly Gly Ser Cys Leu Ser Arg
        195                 200                 205

Ala Cys Arg Ile Asp Ser Thr Thr Lys Leu Tyr Gly Lys Asp Cys Gln
210                 215                 220

Phe Phe Pro Asp Lys Val Gln Thr Glu Lys Ala Ser Ile Met Phe Met
225                 230                 235                 240

Gln Ser Ile Asp Ser Val Val Glu Phe Cys Asn Glu Lys Thr His Asn
                245                 250                 255

Gln Glu Ala Pro Ser Leu Gln Asn Ile Lys Cys Asn Phe Arg Ser Thr
            260                 265                 270

Trp Glu Val Ile Ser Asn Ser Glu Asp Phe Lys Asn Thr Ile Pro Met
        275                 280                 285

Val Thr Pro Pro Pro Pro Val Phe Ser Leu Leu Lys Ile Ser Gln
290                 295                 300

Arg Ile Val Cys Leu Val Leu Asp Lys Ser Gly Ser Met Gly Gly Lys
305                 310                 315                 320

Asp Arg Leu Asn Arg Met Asn Gln Ala Ala Lys His Phe Leu Leu Gln
                325                 330                 335

Thr Val Glu Asn Gly Ser Trp Val Gly Met Val His Phe Asp Ser Thr
            340                 345                 350

Ala Thr Ile Val Asn Lys Leu Ile Gln Ile Lys Ser Ser Asp Glu Arg
        355                 360                 365

Asn Thr Leu Met Ala Gly Leu Pro Thr Tyr Pro Leu Gly Gly Thr Ser
```

-continued

```
            370                 375                 380
Ile Cys Ser Gly Ile Lys Tyr Ala Phe Gln Val Ile Gly Glu Leu His
385                 390                 395                 400
Ser Gln Leu Asp Gly Ser Glu Val Leu Leu Thr Asp Gly Glu Asp
                405                 410                 415
Asn Thr Ala Ser Ser Cys Ile Asp Glu Val Lys Gln Ser Gly Ala Ile
                420                 425                 430
Val His Phe Ile Ala Leu Gly Arg Ala Ala Asp Glu Ala Val Ile Glu
                435                 440                 445
Met Ser Lys Ile Thr Gly Gly Ser His Phe Tyr Val Ser Asp Glu Ala
                450                 455                 460
Gln Asn Asn Gly Leu Ile Asp Ala Phe Gly Ala Leu Thr Ser Gly Asn
465                 470                 475                 480
Thr Asp Leu Ser Gln Lys Ser Leu Gln Leu Glu Ser Lys Gly Leu Thr
                485                 490                 495
Leu Asn Ser Asn Ala Trp Met Asn Asp Thr Val Ile Asp Ser Thr
                500                 505                 510
Val Gly Lys Asp Thr Phe Phe Leu Ile Thr Trp Asn Ser Leu Pro Pro
                515                 520                 525
Ser Ile Ser Leu Trp Asp Pro Ser Gly Thr Ile Met Glu Asn Phe Thr
530                 535                 540
Val Asp Ala Thr Ser Lys Met Ala Tyr Leu Ser Ile Pro Gly Thr Ala
545                 550                 555                 560
Lys Val Gly Thr Trp Ala Tyr Asn Leu Gln Ala Lys Ala Asn Pro Glu
                565                 570                 575
Thr Leu Thr Ile Thr Val Thr Ser Arg Ala Ala Asn Ser Ser Val Pro
                580                 585                 590
Pro Ile Thr Val Asn Ala Lys Met Asn Lys Asp Val Asn Ser Phe Pro
                595                 600                 605
Ser Pro Met Ile Val Tyr Ala Glu Ile Leu Gln Gly Tyr Val Pro Val
                610                 615                 620
Leu Gly Ala Asn Val Thr Ala Phe Ile Glu Ser Gln Asn Gly His Thr
625                 630                 635                 640
Glu Val Leu Glu Leu Leu Asp Asn Gly Ala Gly Ala Asp Ser Phe Lys
                645                 650                 655
Asn Asp Gly Val Tyr Ser Arg Tyr Phe Thr Ala Tyr Thr Glu Asn Gly
                660                 665                 670
Arg Tyr Ser Leu Lys Val Arg Ala His Gly Ala Asn Thr Ala Arg
                675                 680                 685
Leu Lys Leu Arg Pro Pro Leu Asn Arg Ala Ala Tyr Ile Pro Gly Trp
                690                 695                 700
Val Val Asn Gly Glu Ile Glu Ala Asn Pro Pro Arg Pro Glu Ile Asp
705                 710                 715                 720
Glu Asp Thr Gln Thr Thr Leu Glu Asp Phe Ser Arg Thr Ala Ser Gly
                725                 730                 735
Gly Ala Phe Val Val Ser Gln Val Pro Ser Leu Pro Leu Pro Asp Gln
                740                 745                 750
Tyr Pro Pro Ser Gln Ile Thr Asp Leu Asp Ala Thr Val His Glu Asp
                755                 760                 765
Lys Ile Ile Leu Thr Trp Thr Ala Pro Gly Asp Asn Phe Asp Val Gly
                770                 775                 780
Lys Val Gln Arg Tyr Ile Ile Arg Ile Ser Ala Ser Ile Leu Asp Leu
785                 790                 795                 800
```

```
Arg Asp Ser Phe Asp Asp Ala Leu Gln Val Asn Thr Thr Asp Leu Ser
            805                 810                 815

Pro Lys Glu Ala Asn Ser Lys Glu Ser Phe Ala Phe Lys Pro Glu Asn
            820                 825                 830

Ile Ser Glu Glu Asn Ala Thr His Ile Phe Ile Ala Ile Lys Ser Ile
            835                 840                 845

Asp Lys Ser Asn Leu Thr Ser Lys Val Ser Asn Ile Ala Gln Val Thr
    850                 855                 860

Leu Phe Ile Pro Gln Ala Asn Pro Asp Ile Asp Pro Thr Pro Thr
865                 870                 875                 880

Pro Thr Pro Thr Pro Asp Lys Ser His Asn Ser Gly Val Asn Ile Ser
            885                 890                 895

Thr Leu Val Leu Ser Val Ile Gly Ser Val Val Ile Val Asn Phe Ile
            900                 905                 910

Leu Ser Thr Thr Ile
        915
```

(2) INFORMATION FOR SEQ ID NO:42:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:42:

```
Ala Asn Ser Ser Val Pro Pro Ile Thr Val Asn Ala Lys Met Asn Lys
1               5                   10                  15

Asp Val Asn Ser Phe
            20
```

(2) INFORMATION FOR SEQ ID NO:43:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:43:

```
Asp Asn Gly Ala Gly Ala Asp Ser Phe Lys Asn Asp Gly Val Tyr Ser
1               5                   10                  15

Arg Tyr Phe Thr Ala Tyr Thr Glu Asn Gly Arg Tyr Ser Leu Lys
            20                  25                  30
```

(2) INFORMATION FOR SEQ ID NO:44:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:44:

```
Val Arg Ala His Gly Gly Ala Asn Thr Ala Arg Leu Lys Leu Arg Pro
1               5                   10                  15
```

```
Pro Leu Asn Arg Ala Ala Tyr Ile
            20
```

(2) INFORMATION FOR SEQ ID NO:45:

(i) SEQUENCE CHARACTERISTICS:
       (A) LENGTH: 40 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:45:

```
Ser Leu Pro Leu Pro Asp Gln Tyr Pro Pro Ser Gln Ile Thr Asp Leu
1               5                   10                  15

Asp Ala Thr Val His Glu Asp Lys Ile Ile Leu Thr Trp Thr Ala Pro
            20                  25                  30

Gly Asp Asn Phe Asp Val Gly Lys
            35                  40
```

(2) INFORMATION FOR SEQ ID NO:46:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:46:

```
Tyr Asn Glu Asp Gln Pro Phe Tyr Arg Ala Lys Ser Lys Lys Ile Glu
1               5                   10                  15

Ala Thr Arg Cys
            20
```

(2) INFORMATION FOR SEQ ID NO:47:

(i) SEQUENCE CHARACTERISTICS:
       (A) LENGTH: 24 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:47:

```
Leu Ser Arg Ala Cys Arg Ile Asp Ser Thr Thr Lys Leu Tyr Gly Lys
1               5                   10                  15

Asp Cys Gln Phe Phe Pro Asp Lys
            20
```

(2) INFORMATION FOR SEQ ID NO:48:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: None (xi) SEQUENCE DESCRIPTION: SEQ ID NO:48:

```
Lys Ser Ser Asp Glu Arg Asn Thr Leu Met Ala Gly Leu Pro Thr Tyr
1               5                   10                  15
```

```
Pro Leu Gly Gly
        20

(2) INFORMATION FOR SEQ ID NO:49:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:49:

Glu Ile Asp Glu Asp Thr Gln Thr Thr Leu Glu Asp Phe Ser Arg
1               5                   10                  15

(2) INFORMATION FOR SEQ ID NO:50:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:50:

Asp Tyr Lys Asp Asp Asp Asp Lys
1               5

(2) INFORMATION FOR SEQ ID NO:51:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO:51:

Glu Gln Lys Leu Ile Ser Glu Glu Asp Leu Asn Met His Thr Glu His
1               5                   10                  15

His His His His His
        20
```

REAGENTS AND METHODS USEFUL FOR DETECTING DISEASES OF THE GASTROINTESTINAL TRACT

CROSS-REFERENCE TO RELATED APPLICATION

This application is a continuation-in-part of U.S. application Ser. No. 8/828,856, filed Mar. 31, 1997, now abandoned from which priority is claimed pursuant to 35 U.S.C. §120 and which is incorporated herein by reference in its entirety.

BACKGROUND OF THE INVENTION

The invention relates generally to detecting diseases of the gastrointestinal tract organs, and more particularly, relates to reagents such as polynucleotide sequences and the polypeptide sequences encoded thereby, as well as methods which utilize these sequences, which are useful for detecting, diagnosing, staging, monitoring, prognosticating, preventing or treating, or determining predisposition to diseases and conditions of the GI tract such as cancer.

The organs of the GI tract include the esophagus, stomach, small and large intestines, rectum and pancreas. Of the approximately 225,900 new cases of GI tract cancer projected for the United States during 1996, 131,200 will be due to colorectal cancer. Further, GI tract cancers will account for approximately 127,070 related deaths (American Cancer Society statistics). In addition to its high incidence, GI tract cancers can be extremely lethal; for example, greater than 97% of pancreatic cancer patients will die of the disease. H. J. Wanebo, et al., *Cancer* 78:580–91 (1996).

Generally, the early detection of GI tract cancers at a pre-invasive stage dramatically reduces disease-related mortality. However, only few GI tract cancers are detected at this stage. For example, only 37% of colorectal cancers are detected at this stage by screening for premalignant polyps which can be removed before they progress to cancer. The primary methods used for colorectal cancer screening are fecal occult blood testing (FOBT) and flexible sigmoidoscopy. A. M. Cohen et al. In: *Cancer: Principles and Practice of Oncology*, Fourth Edition, pp. 929–977, Philadelphia, Pa.: J/B. Lippincott Co. (1993). Although FOBT is noninvasive, simple and inexpensive, its sensitivity is low; for example, sensitivity for detecting colorectal cancer was only 26% in one study. D. A. Ahlquist et al., *JAMA* 269: 1262–1267 (1993). Further, although flexible sigmoidoscopy is highly sensitive for detecting early cancer and precursor polyps, it is invasive, costly, and too technically demanding to be used for routine screening. D. F. Ransohoff, et al., *JAMA* 269: 1278–1281 (1993). In addition, only eight percent (8%) of pancreatic cancers and eighteen percent (18%) of stomach cancers are detected at a pre-invasive stage (American Cancer Society statistics). Thus, the need exists for improved screening methods for detection of GI tract diseases such as cancer.

The standard procedures currently used for establishing a definitive diagnosis for a GI tract cancer include barium studies, endoscopy, biopsy and computed tomography (CT). These procedures are invasive and costly. Moreover, an erroneous diagnosis can result from any of these procedures due to technical reasons, the subjective interpretation of results, or lack of sensitivity of the procedure. M. F. Brennan, et al. In: *Cancer: Principles and Practice of Oncology*, Fourth Edition, pp. 849–882, Philadelphia, Pa.: J. B. Lippincott Co. (1993).

After the diagnosis of a particular GI tract cancer is confirmed, staging is performed to determine the anatomic extent of the disease. Staging is performed by a pathologist on tissue obtained by biopsy and/or surgery. Accurate staging is critical for predicting patient outcome and providing criteria for designing optimal therapy. Inaccurate staging can result in poor therapeutic decisions and is a major clinical problem in colorectal cancer. A need therefore exists for more sensitive diagnostic procedures for staging GI tract cancers.

While surgical resection of the affected organ is typical therapy for a majority of patients diagnosed with GI tract cancers, some patients undergo radiation and/or chemotherapy. All of these patients need to be monitored in order to evaluate their response to therapy and to detect persistent or recurrent disease and distant metastasis. A variety of markers including CEA and CA 19-9 can be assayed and the assay results used to monitor a patient's progress in conjunction with radiological procedures and colonoscopy. E. L. Jacobs, *Curr. Probl. Cancer* 15 (6):299–350 (1991). These monitoring techniques, however, have failed to provide an accurate and effective means to monitor the progress of these patients.

Assays based upon the appearance of various disease markers in test samples such as blood, plasma or serum obtained by minimally invasive techniques, could provide low-cost and accurate information to aid the physician in diagnosing disease such as cancer, in selecting a therapy protocol, and in monitoring the success of the chosen therapy. Such markers have been placed into several categories. The first category contains those markers which are elevated in disease. Examples include human chorionic gonadotropin (hCG) which is elevated in testicular cancer and trophoblastic disease, and alpha fetoprotein (AFP) which is elevated in hepato-cellular carcinoma (HCC). E. L. Jacobs, supra. The second category includes qualitatively altered mRNA or protein markers in disease. Examples include mRNA splice variants of CD 44 in bladder cancer and mutations in p53 protein in lung and colorectal cancer. Y. Matsumura et al. *Journal of Pathology* 175(Suppl): 108A (1995); W. P. Bennett, *Cancer Detection and Prevention* 19 (6): 503–511 (1995). The third category includes those protein markers which are normally expressed in a specific tissue, organ or organ system but which appear in an inappropriate body compartment. For example, prostate specific antigen (PSA) is a normal protein which is secreted at high levels into the seminal fluid. PSA is present in very low levels in the blood of men with normal prostates but markedly elevated in the blood of patients with diseases of the prostate, including benign prostatic hyperplasia (BPH) and adenocarcinoma of the prostate. At high levels in the blood, PSA is a strong indicator of prostate disease. P. H. Lange et al., *Urology* 33 (6 Suppl): 13 (1989). Similarly, carcinoembryonic antigen (CEA) is a normal component of the inner lining of the colon which is present in blood at low levels in people without colon disease. E. L. Jacobs, supra. However, the CEA concentration is markedly elevated in the blood, plasma or serum of many patients diagnosed with colon disease including inflammatory bowel disease and adenocarcinoma of the colon, and is used as an indicator of colorectal disease.

There are yet other examples of detecting disease markers in an inappropriate bodily compartment. In the case of metastatic cancer, the blood, bone marrow or lymph nodes may contain cells which have originated from the primary tumor and which may express mRNA or protein markers representative of the primary tumor. For example, CEA and PSA have been demonstrated immunohistochemically in lymph nodes or bone marrow of patients with metastatic colorectal cancer and prostate cancer, respectively. B R. Davidson, et al., *Cancer* 65:967–970 (1990); J. L. Mansi, et al., *J. Urol.*, 139:545–548 (1988). In addition, RT-PCR has detected CEA and PSA mRNAs at distant sites in patients with colon and prostate cancer, suggesting the presence of metastatic cells. M. Gerhard, et al., *J. Clin. Oncol.* 12:725–729 (1994); A. E. Katz, et al., *Urology* 43:765–775 (1994). Other compartments in which the inappropriate appearance of normal gene products may be indicative of disease include but are not limited to, whole blood, urine, saliva, and stool. Currently, no universally acceptable marker(s) exist(s) for the early detection of pancreatic, stomach, and esophageal cancers. Further, improved markers are needed to detect colorectal cancer.

It therefore would be advantageous to provide specific methods and reagents for detecting, diagnosing, staging, monitoring, prognosticating, preventing or treating, or determining predisposition to diseases and conditions associated with the GI tract or to indicate possible predisposition to these conditions. Such methods would include assaying a test sample for products of a gene which are overexpressed in GI tract diseases and conditions such as cancer. Such methods may also include assaying a test sample for products of a gene alteration associated with the GI tract disease or condition. Such methods may further include assaying a test sample for products of a gene whose distribution among the various tissues and compartments of the body have been altered by a GI tract-associated disease or condition such as cancer. Useful reagents include polynucleotide(s), or fragment(s) thereof which may be used in diagnostic methods such as reverse transcriptase-polymerase chain reaction (RT-PCR), PCR, or hybridization assays of mRNA extracted from biopsied tissue, blood or other test samples; polypeptides or proteins which are the translation products of such mRNAs; or antibodies directed against these proteins. Drug treatment or gene therapy for diseases or conditions of the GI tract then can be based on these identified gene sequences or their expressed proteins, and efficacy of any particular therapy can be monitored. Furthermore, it would be advantageous to have available alternative, nonsurgical diagnostic methods capable of detecting early stage GI tract disease such as cancer.

SUMMARY OF THE INVENTION

The present invention provides a method of detecting a target CS193 polynucleotide in a test sample which comprises contacting the test sample with at least one CS193-specific polynucleotide and detecting the presence of the target CS193 polynucleotide in the test sample. The CS193-specific polynucleotide has at least 50% identity with a polynucleotide selected from the group consisting of SEQUENCE ID NO 1, SEQUENCE ID NO 2, SEQUENCE ID NO 3, SEQUENCE ID NO 4, SEQUENCE ID NO 5, SEQUENCE ID NO 6, SEQUENCE ID NO 7, SEQUENCE ID NO 8, SEQUENCE ID NO 9, SEQUENCE ID NO 10, SEQUENCE ID NO 11, SEQUENCE ID NO 12, SEQUENCE ID NO 13, SEQUENCE ID NO 14, SEQUENCE ID NO 15, SEQUENCE ID NO 16, SEQUENCE ID NO 17, SEQUENCE ID NO 18 ("SEQUENCE ID NOS 1–18"), and fragments or complements thereof. Also, the CS193-specific polynucleotide may be attached to a solid phase prior to performing the method.

The present invention also provides a method for detecting CS193 mRNA in a test sample, which comprises performing reverse transcription (RT) with at least one primer in order to produce cDNA, amplifying the cDNA so obtained using CS193 oligonucleotides as sense and anti-sense primers to obtain CS193 amplicon, and detecting the presence of the CS193 amplicon as an indication of the presence of CS193 mRNA in the test sample, wherein the CS193 oligonucleotides have at least 50% identity to a sequence selected from the group consisting of SEQUENCE ID NOS 1–18, and fragments or complements thereof. Amplification can be performed by the polymerase chain reaction. Also, the test sample can be reacted with a solid phase prior to performing the method, prior to amplification or prior to detection. This reaction can be a direct or an indirect reaction. Further, the detection step can comprise utilizing a detectable label capable of generating a measurable signal. The detectable label can be attached to a solid phase.

The present invention further provides a method of detecting a target CS193 polynucleotide in a test sample suspected of containing target CS193 polynucleotides, which comprises (a) contacting the test sample with at least one CS193 oligonucleotide as a sense primer and at least one CS193 oligonucleotide as an anti-sense primer, and amplifying same to obtain a first stage reaction product; (b) contacting the first stage reaction product with at least one other CS193 oligonucleotide to obtain a second stage reaction product, with the proviso that the other CS193 oligonucleotide is located 3' to the CS193 oligonucleotides utilized in step (a) and is complementary to the first stage reaction product; and (c) detecting the second stage reaction product as an indication of the presence of a target CS193 polynucleotide in the test sample. The CS193 oligonucleotides selected as reagents in the method have at least 50% identity to a sequence selected from the group consisting of SEQUENCE ID NOS 1–18, and fragments or complements thereof. Amplification may be performed by the polymerase chain reaction. The test sample can be reacted either directly or indirectly with a solid phase prior to performing the method, or prior to amplification, or prior to detection. The detection step also comprises utilizing a detectable label capable of generating a measurable signal; further, the detectable label can be attached to a solid phase. Test kits useful for detecting target CS193 polynucleotides in a test sample are also provided which comprise a container containing at least one CS193-specific polynucleotide selected from the group consisting of SEQUENCE ID NOS 1–18, and fragments or complements thereof. These test kits further comprise containers with tools useful for collecting test samples (such as, for example, blood, urine, saliva and stool). Such tools include lancets and absorbent paper or cloth for collecting and stabilizing blood; swabs for collecting and stabilizing saliva; and cups for collecting and stabilizing urine or stool samples. Collection materials, such as papers, cloths, swabs, cups, and the like, may optionally be treated to avoid denaturation or irreversible adsorption of the sample. The collection materials also may be treated with or contain preservatives, stabilizers or antimicrobial agents to help maintain the integrity of the specimens.

The present invention also provides a purified polynucleotide or fragment thereof derived from a CS193 gene. The purified polynucleotide is capable of selectively hybridizing to the nucleic acid of the CS193 gene, or a complement thereof. The polynucleotide has at least 50% identity to a polynucleotide selected from the group consisting of SEQUENCE ID NOS 1–18, and fragments or complements thereof. Further, the purified polynucleotide can be produced by recombinant and/or synthetic techniques. The purified recombinant polynucleotide can be contained within a recombinant vector. The invention further comprises a host cell transfected with the recombinant vector.

The present invention further provides a recombinant expression system comprising a nucleic acid sequence that includes an open reading frame derived from CS193. The nucleic acid sequence has at least 50% identity with a sequence selected from the group consisting of SEQUENCE ID NOS 1–18, and fragments or complements thereof. The nucleic acid sequence is operably linked to a control sequence compatible with a desired host. Also provided is a cell transfected with this recombinant expression system.

The present invention also provides a polypeptide encoded by CS193. The polypeptide can be produced by recombinant technology, provided in purified form, or produced by synthetic techniques. The polypeptide comprises an amino acid sequence which has at least 60% identity with an amino acid sequence selected from the group consisting of SEQUENCE ID NO 41, SEQUENCE ID NO 42, SEQUENCE ID NO 43, SEQUENCE ID NO 44, SEQUENCE ID NO 45, SEQUENCE ID NO 46, SEQUENCE ID NO 47, SEQUENCE ID NO 48, SEQUENCE ID NO 49 ("SEQUENCE ID NOS 41–49"), and fragments thereof.

Also provided is an antibody which specifically binds to at least one CS193 epitope. The antibody can be a polyclonal or monoclonal antibody. The epitope is derived from an amino acid sequence selected from the group consisting of SEQUENCE ID NOS 41–49, and fragments thereof. Assay kits for determining the presence of CS193 antigen or anti-CS193 antibody in a test sample are also included. In one embodiment, the assay kits comprise a container containing at least one CS193 polypeptide having at least 50% identity to an amino acid sequence selected from the group consisting of SEQUENCE ID NOS 41–49, and fragments thereof. Further, the test kit can comprise a container with tools useful for collecting test samples (such as blood, urine, saliva, and stool). Such tools include lancets and absorbent paper or cloth for collecting and stabilizing blood; swabs for collecting and stabilizing saliva; and cups for collecting and stabilizing urine or stool samples. Collection materials such as papers, cloths, swabs, cups, and the like, may optionally be treated to avoid denaturation or irreversible adsorption of the sample. These collection materials also may be treated with or contain preservatives, stabilizers or antimicrobial agents to help maintain the integrity of the specimens. Also, the polypeptide can be attached to a solid phase.

Another assay kit for determining the presence of CS193 antigen or anti-CS193 antibody in a test sample comprises a container containing an antibody which specifically binds to a CS193 antigen, wherein the CS193 antigen comprises at least one CS193-encoded epitope. The CS193 antigen has at least about 60% sequence similarity to a sequence of a CS193-encoded antigen selected from the group consisting of SEQUENCE ID NOS 41–49, and fragments thereof. These test kits can further comprise containers with tools useful for collecting test samples (such as blood, urine, saliva, and stool). Such tools include lancets and absorbent paper or cloth for collecting and stabilizing blood; swabs for collecting and stabilizing saliva; cups for collecting and stabilizing urine or stool samples. Collection materials, papers, cloths, swabs, cups and the like, may optionally be treated to avoid denaturation or irreversible adsorption of the sample. These collection materials also may be treated with, or contain, preservatives, stabilizers or antimicrobial agents to help maintain the integrity of the specimens. The antibody can be attached to a solid phase.

A method for producing a polypeptide which contains at least one epitope of CS193 is provided, which method comprises incubating host cells that have been transfected with an expression vector. This vector comprises a polynucleotide sequence encoding a polypeptide, wherein the polypeptide comprises an amino acid sequence having at least 60% identity to a CS193 amino acid sequence selected from the group consisting of SEQUENCE ID NOS 41–49, and fragments thereof.

A method for detecting CS193 antigen in a test sample suspected of containing CS193 antigen also is provided. The method comprises contacting the test sample with an antibody or fragment thereof which specifically binds to at least one epitope of CS193 antigen, for a time and under conditions sufficient for the formation of antibody/antigen complexes; and detecting the presence of such complexes containing the antibody as an indication of the presence of CS193 antigen in the test sample. The antibody can be attached to a solid phase and may be either a monoclonal or polyclonal antibody. Furthermore, the antibody specifically binds to at least one CS193 antigen selected from the group consisting of SEQUENCE ID NOS 41–49, and fragments thereof.

Another method is provided which detects antibodies which specifically bind to CS193 antigen in a test sample suspected of containing these antibodies. The method comprises contacting the test sample with a polypeptide which contains at least one CS193 epitope, wherein the CS193 epitope comprises an amino acid sequence having at least 50% identity with an amino acid sequence encoded by a CS193 polynucleotide, or a fragment thereof. Contacting is carried out for a time and under conditions sufficient to allow antigen/antibody complexes to form. The method further entails detecting complexes which contain the polypeptide. The polypeptide can be attached to a solid phase. Further, the polypeptide can be a recombinant protein or a synthetic peptide having at least 50% identity to an amino acid sequence selected from the group consisting of SEQUENCE ID NOS 41–49, and fragments thereof.

The present invention provides a cell transfected with a CS193 nucleic acid sequence that encodes at least one epitope of a CS193 antigen or fragment thereof. The nucleic acid sequence is selected from the group consisting of SEQUENCE ID NOS 1–18, and fragments or complements thereof.

A method for producing antibodies to CS193 antigen also is provided, which method comprises administering to an individual an isolated immunogenic polypeptide or fragment thereof, wherein the isolated immunogenic polypeptide comprises at least one CS193 epitope. The immunogenic polypeptide or fragment thereof is administered in an amount sufficient to produce an immune response. The isolated, immunogenic polypeptide comprises an amino acid sequence selected from the group consisting of SEQUENCE ID NOS 41–49, and fragments thereof.

Another method for producing antibodies which specifically bind to CS193 antigen is disclosed, which method comprises administering to an individual a plasmid comprising a nucleic acid sequence which encodes at least one CS193 epitope derived from an amino acid sequence selected from the group consisting of SEQUENCE ID NOS 41–49, and fragments thereof. The plasmid is administered in an amount such that the plasmid is taken up by cells in the individual and expressed at levels sufficient to produce an immune response.

Also provided is a composition of matter that comprises a CS193 polynucleotide of at least about 10–12 nucleotides having at least 50% identity to a polynucleotide selected from the group consisting of SEQUENCE ID NOS 1–18, and fragments or complements thereof. The CS193 polynucleotide encodes an amino acid sequence having at least one CS193 epitope. Another composition of matter provided by the present invention comprises a polypeptide with at least one CS193 epitope of about 8–10 amino acids. The polypeptide comprises an amino acid sequence having at least 60% identity with an amino acid sequence selected from the group consisting of SEQUENCE ID NOS 41–49, and fragments thereof. Also provided is a gene, or fragment thereof, coding for a CS193 polypeptide which has at least 60% identity to SEQUENCE ID NO 41; and a gene, or a fragment thereof, comprising DNA having at least 50% identity to SEQUENCE ID NO 16, SEQUENCE ID NO 17, or SEQUENCE ID NO 18.

BRIEF DESCRIPTION OF THE DRAWINGS

FIGS. 1A–1G show the nucleotide alignment of clones 2767646 (SEQUENCE ID NO 1), 774134 (SEQUENCE ID NO 2), 775437 (SEQUENCE ID NO 3), 1281329 (SEQUENCE ID NO 4), 1628677 (SEQUENCE ID NO 5), 1286372 (SEQUENCE ID NO 6), 774419 (SEQUENCE ID NO 7), 3233118 (SEQUENCE ID NO 8), 2733923 (SEQUENCE ID NO 9), 906605 (SEQUENCE ID NO 10), 2771475 (SEQUENCE ID NO 11), 1803247 (SEQUENCE ID NO 12), 1737526 (SEQUENCE ID NO 13), 2792957 (SEQUENCE ID NO 14), 1226186 (SEQUENCE ID NO 15); the consensus sequence (SEQUENCE ID NO 18) derived therefrom; and the full-length sequences of clone 774134 (designated as clone 774134IH (SEQUENCE ID NO 16)) and clone 774419 (designated as clone 774419IH (SEQUENCE ID NO 17)).

DETAILED DESCRIPTION OF THE INVENTION

Figure 2:
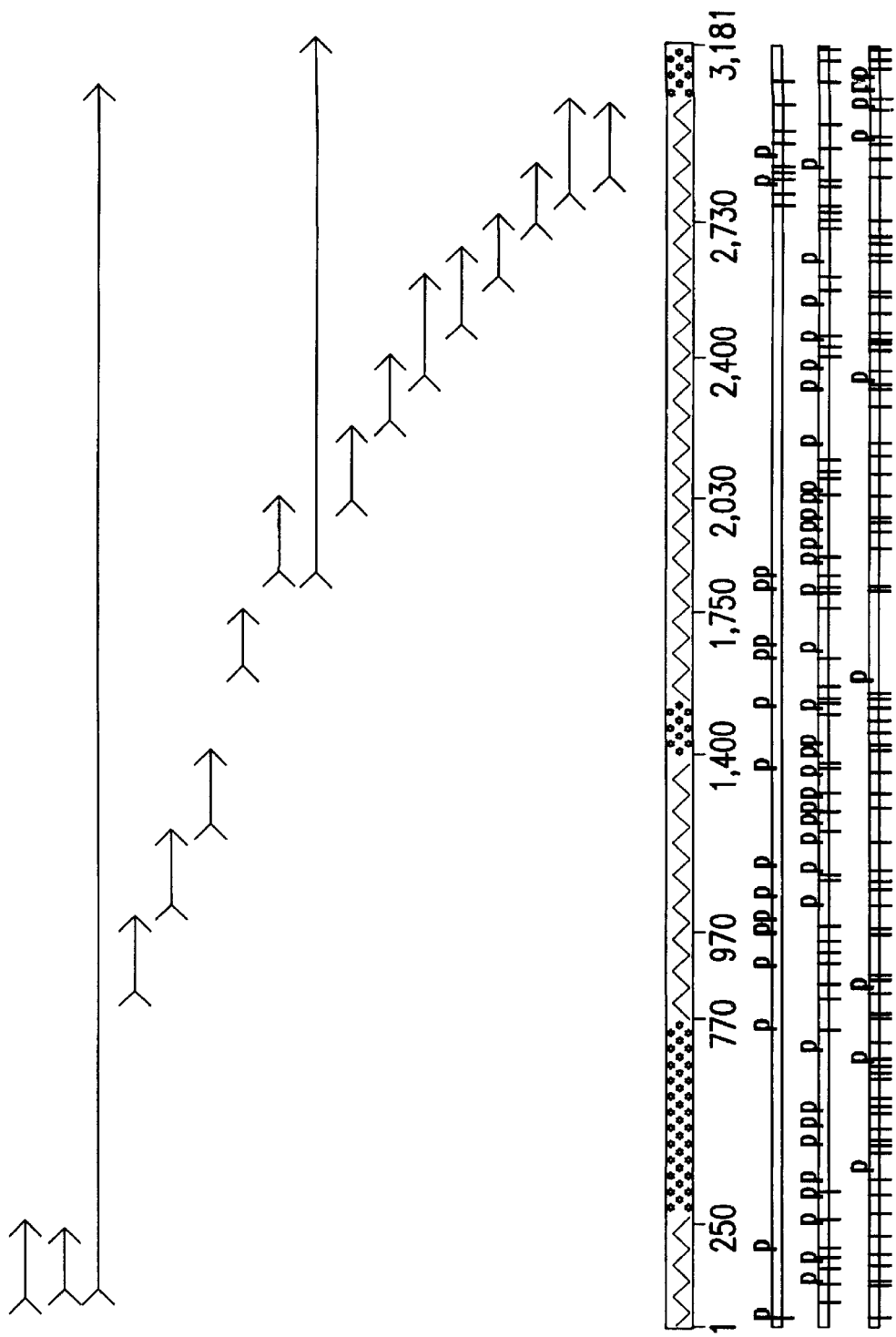
FIG. 2 shows the contig map depicting the formation of the consensus nucleotide sequence (SEQUENCE ID NO 18) from the nucleotide alignment of overlapping clones 2767646 (SEQUENCE ID NO 1), 774134 (SEQUENCE ID NO 2), 775437 (SEQUENCE ID NO 3), 1281329 (SEQUENCE ID NO 4), 1628677 (SEQUENCE ID NO 5), 1286372 (SEQUENCE ID NO 6), 774419 (SEQUENCE ID NO 7), 3233118 (SEQUENCE ID NO 8), 2733923 (SEQUENCE ID NO 9), 906605 (SEQUENCE ID NO 10), 2771475 (SEQUENCE ID NO 11), 1803247 (SEQUENCE ID NO 12), 1737526 (SEQUENCE ID NO 13), 2792957 (SEQUENCE ID NO 14), 1226186 (SEQUENCE ID NO 15), 774134IH (SEQUENCE ID NO 16), and 774419IH (SEQUENCE ID NO 17).

The present invention provides a gene, or a fragment thereof, which codes for a CS193 polypeptide having at least about 60% identity to SEQUENCE ID NO 41. The present invention further encompasses a CS193 gene, or a fragment thereof, comprising DNA which has at least about 50% identity to SEQUENCE ID NO 16, SEQUENCE ID NO 17, or SEQUENCE ID NO 18.

The present invention also provides methods for assaying a test sample for products of a gastrointestinal tract (GI tract) tissue gene designated as CS193, which method comprises making cDNA from mRNA in the test sample and detecting the cDNA as an indication of the presence of GI tract tissue gene CS193. The method may include an amplification step, wherein one or more portions of the mRNA from CS193 corresponding to the gene or fragments thereof, is amplified. Methods also are provided for assaying for the translation products of CS193. Test samples which may be assayed by the methods provided herein include tissues, cells, body fluids and secretions. The present invention also provides reagents such as oligonucleotide primers and polypeptides which are useful in performing these methods.

Portions of the nucleic acid sequences disclosed herein are useful as primers for the reverse transcription of RNA or for the amplification of cDNA or as probes to determine the presence of certain mRNA sequences in test samples. Also disclosed are nucleic acid sequences which permit the production of encoded polypeptide sequences which are useful as standards or reagents in diagnostic immunoassays, as targets for pharmaceutical screening assays and/or as components or as target sites for various therapies. Monoclonal and polyclonal antibodies directed against at least one epitope contained within these polypeptide sequences are useful as delivery agents for therapeutic agents as well as for diagnostic tests and for screening for diseases or conditions associated with CS193, especially GI tract cancer. Isolation of sequences of other portions of the gene of interest can be accomplished utilizing probes or PCR primers derived from these nucleic acid sequences. This allows additional probes of the mRNA or cDNA of interest to be established, as well as corresponding encoded polypeptide sequences. These additional molecules are useful in detecting, diagnosing, staging, monitoring, prognosticating, preventing or treating, or determining the predisposition to diseases and conditions of the GI tract, such as GI tract cancer, characterized by CS193, as disclosed herein.

Techniques for determining amino acid sequence "similarity" are well-known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity." Two or more amino acid sequences likewise can be compared by determining their "percent identity." The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known in the art.

The compositions and methods described herein will enable the identification of certain markers as indicative of a GI tract tissue disease or condition. The information obtained therefrom will aid in the detecting, diagnosing, staging, monitoring, prognosticating, preventing or treating, or determining diseases or conditions associated with CS193, especially GI tract cancer. Test methods include, for example, probe assays which utilize the sequence(s) provided herein and which also may utilize nucleic acid amplification methods such as the polymerase chain reaction (PCR), the ligase chain reaction (LCR), and hybridization. In addition, the nucleotide sequences provided herein contain open reading frames from which an immunogenic epitope may be found. This epitope is believed to be unique to the disease state or condition associated with CS193. It also is thought that the polynucleotides or polypeptides and protein encoded by the CS193 gene are useful as a marker. This marker is either elevated in disease such as GI tract cancer, altered in disease such as GI tract cancer, or present as a normal protein but appearing in an inappropriate body compartment. The uniqueness of the epitope may be determined by (i) its immunological reactivity and specificity with antibodies directed against proteins and polypeptides encoded by the CS193 gene, and (ii) its nonreactivity with any other tissue markers. Methods for determining immunological reactivity are well-known and include, but are not limited to, for example, radioimmunoassay (RIA), enzyme-linked immunoabsorbent assay (ELISA), hemagglutination (HA), fluorescence polarization immunoassay (FPIA), chemiluminescent immunoassay (CLIA) and others. Several examples of suitable methods are described herein.

Unless otherwise stated, the following terms shall have the following meanings:

A polynucleotide "derived from" or "specific for" a designated sequence refers to a polynucleotide sequence which comprises a contiguous sequence of approximately at least about 6 nucleotides, preferably at least about 8 nucleotides, more preferably at least about 10–12 nucleotides, and even more preferably at least about 15–20 nucleotides corresponding, i.e., identical or complementary to, a region of the designated nucleotide sequence. The sequence may be complementary or identical to a sequence which is unique to a particular polynucleotide sequence as determined by techniques known in the art. Comparisons to sequences in databanks, for example, can be used as a method to determine the uniqueness of a designated sequence. Regions from which sequences may be derived, include but are not limited to, regions encoding specific epitopes, as well as non-translated and/or non-transcribed regions.

The derived polynucleotide will not necessarily be derived physically from the nucleotide sequence of interest under study, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide. In addition, combinations of regions corresponding to that of the designated sequence may be modified in ways known in the art to be consistent with the intended use.

A "fragment" of a specified polynucleotide refers to a polynucleotide sequence which comprises a contiguous sequence of approximately at least about 6 nucleotides, preferably at least about 8 nucleotides, more preferably at least about 10–12 nucleotides, and even more preferably at least about 15–20 nucleotides corresponding, i.e., identical or complementary to, a region of the specified nucleotide sequence.

The term "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase.

The term "probe" denotes a defined nucleic acid segment (or nucleotide analog segment, e.g., PNA as defined hereinbelow) which can be used to identify a specific polynucleotide present in samples bearing the complementary sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence. Thus, a "polypeptide," "protein," or "amino acid" sequence has at least about 50% identity, preferably about 60% identity, more preferably about 75–85% identity, and most preferably about 90–95% or more identity to a CS193 amino acid sequence. Further, the CS193 "polypeptide," "protein," or "amino acid" sequence may have at least about 60% similarity, preferably at least about 75% similarity, more preferably about 85% similarity, and most preferably about 95% or more similarity to a polypeptide or amino acid sequence of CS193. This amino acid sequence can be selected from the group consisting of SEQUENCE ID NO 41, SEQUENCE ID NO 42, SEQUENCE ID NO 43, SEQUENCE ID NO 44, SEQUENCE ID NO 45, SEQUENCE ID NO 46, SEQUENCE ID NO 47, SEQUENCE ID NO 48, SEQUENCE ID NO 49, and fragments thereof.

A "recombinant polypeptide," "recombinant protein," or "a polypeptide produced by recombinant techniques," which terms may be used interchangeably herein, describes a polypeptide which by virtue of its origin or manipulation is not associated with all or a portion of the polypeptide with which it is associated in nature and/or is linked to a polypeptide other than that to which it is linked in nature. A recombinant or encoded polypeptide or protein is not necessarily translated from a designated nucleic acid sequence. It also may be generated in any manner, including chemical synthesis or expression of a recombinant expression system.

The term "synthetic peptide" as used herein means a polymeric form of amino acids of any length, which may be chemically synthesized by methods well-known to the routineer. These synthetic peptides are useful in various applications.

The term "polynucleotide," as used herein, means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, such as methylation or capping and unmodified forms of the polynucleotide. The terms "polynucleotide," "oligomer," "oligonucleotide," and "oligo" are used interchangeably herein.

"A sequence corresponding to a cDNA" means that the sequence contains a polynucleotide sequence that is identical or complementary to a sequence in the designated DNA. The degree (or "percent") of identity or complementarity to the cDNA will be approximately 50% or greater, preferably at least about 70% or greater, and more preferably at least about 90% or greater. The sequence that corresponds to the identified cDNA will be at least about 50 nucleotides in length, preferably at least about 60 nucleotides in length, and more preferably at least about 70 nucleotides in length. The correspondence between the gene or gene fragment of interest and the cDNA can be determined by methods known in the art and include, for example, a direct comparison of the sequenced material with the cDNAs described, or hybridization and digestion with single strand nucleases, followed by size determination of the digested fragments.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

"Purified polypeptide" or "purified protein" means a polypeptide of interest or fragment thereof which is essentially free of, e.g., contains less than about 50%, preferably less than about 70%, and more preferably less than about 90%, cellular components with which the polypeptide of interest is naturally associated. Methods for purifying polypeptides of interest are known in the art.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, which is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

"Polypeptide" and "protein" are used interchangeably herein and indicate at least one molecular chain of amino acids linked through covalent and/or non-covalent bonds. The terms do not refer to a specific length of the product. Thus peptides, oligopeptides and proteins are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide.

A "fragment" of a specified polypeptide refers to an amino acid sequence which comprises at least about 3–5 amino acids, more preferably at least about 8–10 amino acids, and even more preferably at least about 15–20 amino acids derived from the specified polypeptide.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

As used herein "replicon" means any genetic element, such as a plasmid, a chromosome or a virus, that behaves as an autonomous unit of polynucleotide replication within a cell.

A "vector" is a replicon in which another polynucleotide segment is attached, such as to bring about the replication and/or expression of the attached segment.

The term "control sequence" refers to a polynucleotide sequence which is necessary to effect the expression of a coding sequence to which it is ligated. The nature of such control sequences differs depending upon the host organism. In prokaryotes, such control sequences generally include a promoter, a ribosomal binding site and terminators; in eukaryotes, such control sequences generally include promoters, terminators and, in some instances, enhancers. The term "control sequence" thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequence.

The term "open reading frame" or "ORF" refers to a region of a polynucleotide sequence which encodes a polypeptide. This region may represent a portion of a coding sequence or a total coding sequence.

A "coding sequence" is a polynucleotide sequence which is transcribed into mRNA and translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA and recombinant polynucleotide sequences.

The term "immunologically identifiable with/as" refers to the presence of epitope(s) and polypeptide(s) which also are present in and are unique to the designated polypeptide(s). Immunological identity may be determined by antibody binding and/or competition in binding. These techniques are known to the routineer and also are described herein. The uniqueness of an epitope also can be determined by computer searches of known data banks, such as GenBank, for the polynucleotide sequence which encodes the epitope and by amino acid sequence comparisons with other known proteins.

As used herein, "epitope" means an antigenic determinant of a polypeptide or protein. Conceivably, an epitope can comprise three amino acids in a spatial conformation which is unique to the epitope. Generally, an epitope consists of at least five such amino acids and more usually, it consists of at least eight to ten amino acids. Methods of examining spatial conformation are known in the art and include, for example, x-ray crystallography and two-dimensional nuclear magnetic resonance.

A "conformational epitope" is an epitope that is comprised of a specific juxtaposition of amino acids in an immunologically recognizable structure, such amino acids being present on the same polypeptide in a contiguous or non-contiguous order or present on different polypeptides.

A polypeptide is "immunologically reactive" with an antibody when it binds to an antibody due to antibody recognition of a specific epitope contained within the polypeptide. Immunological reactivity may be determined by antibody binding, more particularly, by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an epitope of interest" means naturally occurring polypeptides of interest or fragments thereof, as well as polypeptides prepared by other means, for example, by chemical synthesis or the expression of the polypeptide in a recombinant organism.

The term "transfection" refers to the introduction of an exogenous polynucleotide into a prokaryotic or eucaryotic host cell, irrespective of the method used for the introduction. The term "transfection" refers to both stable and transient introduction of the polynucleotide, and encompasses direct uptake of polynucleotides, transformation, transduction, and f-mating. Once introduced into the host cell, the exogenous polynucleotide may be maintained as a non-integrated replicon, for example, a plasmid, or alternatively, may be integrated into the host genome.

"Treatment" refers to prophylaxis and/or therapy.

The term "individual" as used herein refers to vertebrates, particularly members of the mammalian species and includes, but is not limited to, domestic animals, sports animals, primates and humans; more particularly, the term refers to humans.

The term "sense strand" or "plus strand" (or "+") as used herein denotes a nucleic acid that contains the sequence that encodes the polypeptide. The term "antisense strand" or "minus strand" (or "−") denotes a nucleic acid that contains a sequence that is complementary to that of the "plus" strand.

The term "test sample" refers to a component of an individual's body which is the source of the analyte (such as antibodies of interest or antigens of interest). These components are well known in the art. A test sample is typically anything suspected of containing a target sequence. Test samples can be prepared using methodologies well known in the art such as by obtaining a specimen from an individual and, if necessary, disrupting any cells contained thereby to release target nucleic acids. These test samples include biological samples which can be tested by the methods of the present invention described herein and include human and animal body fluids such as whole blood, serum, plasma, cerebrospinal fluid, sputum, bronchial washing, bronchial aspirates, urine, lymph fluids, and various external secretions of the respiratory, intestinal and genitourinary tracts, tears, saliva, milk, white blood cells, myelomas and the like; biological fluids such as cell culture supernatants; tissue specimens which may be fixed; and cell specimens which may be fixed.

"Purified product" refers to a preparation of the product which has been isolated from the cellular constituents with which the product is normally associated and from other types of cells which may be present in the sample of interest.

"PNA" denotes a "peptide nucleic acid analog" which may be utilized in a procedure such as an assay described herein to determine the presence of a target. "MA" denotes a "morpholino analog" which may be utilized in a procedure such as an assay described herein to determine the presence of a target. See, for example, U.S. Pat. No. 5,378,841, which is incorporated herein by reference. PNAs are neutrally charged moieties which can be directed against RNA targets or DNA. PNA probes used in assays in place of, for example, the DNA probes of the present invention, offer advantages not achievable when DNA probes are used. These advantages include manufacturability, large scale labeling, reproducibility, stability, insensitivity to changes in ionic strength and resistance to enzymatic degradation which is present in methods utilizing DNA or RNA. These PNAs can be labeled with ("attached to") such signal generating compounds as fluorescein, radionucleotides, chemiluminescent compounds and the like. PNAs or other nucleic acid analogs such as MAs thus can be used in assay methods in place of DNA or RNA. Although assays are described herein utilizing DNA probes, it is within the scope of the routineer that PNAs or MAs can be substituted for RNA or DNA with appropriate changes if and as needed in assay reagents.

"Analyte," as used herein, is the substance to be detected which may be present in the test sample. The analyte can be any substance for which there exists a naturally occurring specific binding member (such as an antibody), or for which a specific binding member can be prepared. Thus, an analyte is a substance that can bind to one or more specific binding members in an assay. "Analyte" also includes any antigenic substances, haptens, antibodies and combinations thereof. As a member of a specific binding pair, the analyte can be detected by means of naturally occurring specific binding partners (pairs) such as the use of intrinsic factor protein as a member of a specific binding pair for the determination of Vitamin B 12, the use of folate-binding protein to determine folic acid, or the use of a lectin as a member of a specific binding pair for the determination of a carbohydrate. The analyte can include a protein, a polypeptide, an amino acid, a nucleotide target and the like.

The terms "diseases of the GI tract," "GI tract disease," and "condition of the GI tract" are used interchangeably herein to refer to any disease or condition of the esophagus, stomach, small and large intestines, rectum and pancreas including, but not limited to, Barret's esophagus, gastric ulcer, gastritis, leiomyoma, polyps, Crohn's disease, ulcerative colitis, pancreatitis and cancer.

"GI tract cancer," as used herein, refers to any malignant disease of the gastrointestinal tract including, but not limited to, adenocarcinoma, mucinous adenocarcinoma, carcinoid tumor, squamous cell carcinoma, lymphoma, and sarcoma.

An "Expressed Sequence Tag" or "EST" refers to the partial sequence of a cDNA insert which has been made by reverse transcription of mRNA extracted from a tissue followed into a vector.

A "transcript image" refers to a table or list giving the quantitative distribution of ESTs in a library and represents the genes active in the tissue from which the library was made.

The present invention provides assays which utilize specific binding members. A "specific binding member," as used herein, is a member of a specific binding pair. That is, two different molecules where one of the molecules, through chemical or physical means, specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors, and enzymes and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal and complexes thereof, including those formed by recombinant DNA molecules.

The term "hapten," as used herein, refers to a partial antigen or non-protein binding member which is capable of binding to an antibody, but which is not capable of eliciting antibody formation unless coupled to a carrier protein.

A "capture reagent," as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a "signal-generating compound" ("label") which is capable of generating and generates a measurable signal detectable by external means, conjugated ("attached") to a specific binding member. In addition to being an antibody member of a specific binding pair, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme and the like. An immunoreactive specific binding member can be an antibody, an antigen, or an antibody/antigen complex that is capable of binding either to the polypeptide of interest as in a sandwich assay, to the capture reagent as in a competitive assay, or to the ancillary specific binding member as in an indirect assay. When describing probes and probe assays, the term "reporter molecule" may be used. A reporter molecule comprises a signal generating compound as described hereinabove conjugated to a specific binding member of a specific binding pair, such as carbazole or adamantane.

The various "signal-generating compounds" (labels) contemplated include chromagens, catalysts such as enzymes, luminescent compounds such as fluorescein and rhodamine, chemiluminescent compounds such as dioxetanes, acridiniums, phenanthridiniums and luminol, radioactive elements and direct visual labels. Examples of enzymes include alkaline phosphatase, horseradish peroxidase, beta-galactosidase and the like. The selection of a particular label is not critical, but it must be capable of producing a signal either by itself or in conjunction with one or more additional substances.

"Solid phases" ("solid supports") are known to those in the art and include the walls of wells of a reaction tray, test tubes, polystyrene beads, magnetic or non-magnetic beads, nitrocellulose strips, membranes, microparticles such as latex particles, sheep (or other animal) red blood cells and Duracytese® (red blood cells "fixed" by pyruvic aldehyde and formaldehyde, available from Abbott Laboratories, Abbott Park, Ill.) and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase," as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art.

It is contemplated and within the scope of the present invention that the solid phase also can comprise any suitable porous material with sufficient porosity to allow access by detection antibodies and a suitable surface affinity to bind antigens. Microporous structures generally are preferred, but materials with a gel structure in the hydrated state may be used as well. Such useful solid supports include, but are not limited to, nitrocellulose and nylon. It is contemplated that such porous solid supports described herein preferably are in the form of sheets of thickness from about 0.01 to 0.5 mm, preferably about 0.1 mm. The pore size may vary within wide limits and preferably is from about 0.025 to 15 microns, especially from about 0.15 to 15 microns. The surface of such supports may be activated by chemical processes which cause covalent linkage of the antigen or antibody to the support. The irreversible binding of the antigen or antibody is obtained, however, in general, by adsorption on the porous material by poorly understood hydrophobic forces. Other suitable solid supports are known in the art.

Reagents

The present invention provides reagents such as polynucleotide sequences derived from a GI tract tissue of interest and designated as CS193, polypeptides encoded thereby and antibodies specific for these polypeptides. The present invention also provides reagents such as oligonucleotide fragments derived from the disclosed polynucleotides and nucleic acid sequences complementary to these polynucleotides. The polynucleotides, polypeptides, or antibodies of the present invention may be used to provide information leading to the detecting, diagnosing, staging, monitoring, prognosticating, preventing or treating of, or determining the predisposition to, diseases and conditions of the GI tract, such as GI tract cancer. The sequences disclosed herein represent unique polynucleotides which can be used in assays or for producing a specific profile of gene transcription activity. Such assays are disclosed in European Patent Number 0373203B1 and International Publication No. WO 95/11995, which are hereby incorporated by reference.

Selected CS193-derived polynucleotides can be used in the methods described herein for the detection of normal or altered gene expression. Such methods may employ CS193 polynucleotides or oligonucleotides, fragments or derivatives thereof, or nucleic acid sequences complementary thereto.

The polynucleotides disclosed herein, their complementary sequences, or fragments of either, can be used in assays to detect, amplify or quantify genes, nucleic acids, cDNAs or mRNAs relating to GI tract tissue disease and conditions associated therewith. They also can be used to identify an entire or partial coding region of a CS193 polypeptide. They further can be provided in individual containers in the form of a kit for assays, or provided as individual compositions. If provided in a kit for assays, other suitable reagents such as buffers, conjugates and the like may be included.

The polynucleotide may be in the form of RNA or DNA. Polynucleotides in the form of DNA, cDNA, genomic DNA, nucleic acid analogs and synthetic DNA are within the scope of the present invention. The DNA may be double-stranded or single-stranded, and if single stranded, may be the coding (sense) strand or non-coding (anti-sense) strand. The coding sequence which encodes the polypeptide may be identical to the coding sequence provided herein or may be a different coding sequence which coding sequence, as a result of the redundancy or degeneracy of the genetic code, encodes the same polypeptide as the DNA provided herein.

This polynucleotide may include only the coding sequence for the polypeptide, or the coding sequence for the polypeptide and an additional coding sequence such as a leader or secretory sequence or a proprotein sequence, or the coding sequence for the polypeptide (and optionally an additional coding sequence) and non-coding sequence, such as a non-coding sequence 5' and/or 3' of the coding sequence for the polypeptide.

In addition, the invention includes variant polynucleotides containing modifications such as polynucleotide deletions, substitutions or additions; and any polypeptide modification resulting from the variant polynucleotide sequence. A polynucleotide of the present invention also may have a coding sequence which is a naturally occurring allelic variant of the coding sequence provided herein.

In addition, the coding sequence for the polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the polypeptide. The polynucleotides may also encode for a proprotein which is the protein plus additional 5' amino acid residues. A protein having a prosequence is a proprotein and may, in some cases, be an inactive form of the protein. Once the prosequence is cleaved, an active protein remains. Thus, the polynucleotide of the present invention may encode for a protein, or for a protein having a prosequence, or for a protein having both a presequence (leader sequence) and a prosequence.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the polypeptide fused to the marker in the case of a bacterial host, or, for example, the marker sequence may be a hemagglutinin (HA) tag when a mammalian host, e.g. a COS-7 cell line, is used. The HA tag corresponds to an epitope derived from the influenza hemagglutinin protein. See, for example, I. Wilson et al., *Cell* 37:767 (1984).

It is contemplated that polynucleotides will be considered to hybridize to the sequences provided herein if there is at least 50%, preferably at least 70%, and more preferably at least 90% identity between the polynucleotide and the sequence.

The present invention also provides an antibody produced by using a purified CS193 polypeptide of which at least a portion of the polypeptide is encoded by a CS193 polynucleotide selected from the polynucleotides provided herein. These antibodies may be used in the methods provided herein for the detection of CS193 antigen in test samples. The presence of CS193 antigen in the test samples is indicative of the presence of a GI tract disease or condition. The antibody also may be used for therapeutic purposes, for example, in neutralizing the activity of CS193 polypeptide in conditions associated with altered or abnormal expression.

The present invention further relates to a CS193 polypeptide which has the deduced amino acid sequence as provided herein, as well as fragments, analogs and derivatives of such polypeptide. The polypeptide of the present invention may be a recombinant polypeptide, a natural purified polypeptide or a synthetic polypeptide. The fragment, derivative or analog of the CS193 polypeptide may be one in which one or more of the amino acid residues is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be one in which the polypeptide is fused with another compound, such as a compound to increase the half-life of the polypeptide (for example, polyethylene glycol); or it may be one in which the additional amino acids are fused to the polypeptide, such as a leader or secretory sequence or a sequence which is employed for purification of the polypeptide or a proprotein sequence. Such fragments, derivatives and analogs are within the scope of the present invention. The polypeptides and polynucleotides of the present invention are provided preferably in an isolated form and preferably purified.

Thus, a polypeptide of the present invention may have an amino acid sequence that is identical to that of the naturally occurring polypeptide or that is different by minor variations due to one or more amino acid substitutions. The variation may be a "conservative change" typically in the range of about 1 to 5 amino acids, wherein the substituted amino acid has similar structural or chemical properties, e.g., replacement of leucine with isoleucine or threonine with serine. In contrast, variations may include nonconservative changes, e.g., replacement of a glycine with a tryptophan. Similar minor variations may also include amino acid deletions or insertions, or both. Guidance in determining which and how many amino acid residues may be substituted, inserted or deleted without changing biological or immunological activity may be found using computer programs well known in the art, for example, DNASTAR software (DNASTAR Inc., Madison Wis.).

Probes constructed according to the polynucleotide sequences of the present invention can be used in various assay methods to provide various types of analysis. For example, such probes can be used in fluorescent in situ hybridization (FISH) technology to perform chromosomal analysis, and used to identify cancer-specific structural alterations in the chromosomes, such as deletions or translocations that are visible from chromosome spreads or detectable using PCR-generated and/or allele specific oligonucleotides probes, allele specific amplification or by direct sequencing. Probes also can be labeled with radioisotopes, directly- or indirectly-detectable haptens, or fluorescent molecules, and utilized for in situ hybridization studies to evaluate the mRNA expression of the gene comprising the polynucleotide in tissue specimens or cells.

This invention also provides teachings as to the production of the polynucleotides and polypeptides provided herein.

Probe Assays

The sequences provided herein may be used to produce probes which can be used in assays for the detection of nucleic acids in test samples. The probes may be designed from conserved nucleotide regions of the polynucleotides of interest or from non-conserved nucleotide regions of the polynucleotide of interest. The design of such probes for optimization in assays is within the skill of the routineer. Generally, nucleic acid probes are developed from non-conserved or unique regions when maximum specificity is desired, and nucleic acid probes are developed from conserved regions when assaying for nucleotide regions that are closely related to, for example, different members of a multi-gene family or in related species like mouse and man.

The polymerase chain reaction (PCR) is a technique for amplifying a desired nucleic acid sequence (target) contained in a nucleic acid or mixture thereof. In PCR, a pair of primers are employed in excess to hybridize to the complementary strands of the target nucleic acid. The primers are each extended by a polymerase using the target nucleic acid as a template. The extension products become target sequences themselves, following dissociation from the original target strand. New primers then are hybridized and extended by a polymerase, and the cycle is repeated to geometrically increase the number of target sequence molecules. PCR is disclosed in U.S. Pat. Nos. 4,683,195 and 4,683,202, which are incorporated herein by reference.

The Ligase Chain Reaction (LCR) is an alternate method for nucleic acid amplification. In LCR, probe pairs are used which include two primary (first and second) and two secondary (third and fourth) probes, all of which are employed in molar excess to target. The first probe hybridizes to a first segment of the target strand, and the second probe hybridizes to a second segment of the target strand, the first and second segments being contiguous so that the primary probes abut one another in 5' phosphate-3' hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. This technique is described more completely in EP-A-320 308 to K. Backman published Jun. 16, 1989 and EP-A-439 182 to K. Backman et al, published Jul. 31, 1991, both of which are incorporated herein by reference.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770, which is incorporated herein by reference; or reverse transcribe mRNA into cDNA followed by asymmetric gap ligase chain reaction (RT-AGLCR) as described by R. L. Marshall et al., *PCR Methods and Applications* 4: 80–84 (1994), which also is incorporated herein by reference.

Other known amplification methods which can be utilized herein include but are not limited to the so-called "NASBA" or "3SR" technique described by J. C. Guatelli et al., *PNAS USA* 87:1874–1878 (1990) and also described by J. Compton, *Nature* 350 (No. 6313):91–92 (1991); Q-beta amplification as described in published European Patent Application (EPA) No. 4544610; strand displacement amplification (as described in G. T. Walker et al., *Clin. Chem.* 42:9–13 [1996]) and European Patent Application No. 684315; and target mediated amplification, as described in International Publication No. WO 93/22461.

Detection of CS193 may be accomplished using any suitable detection method, including those detection methods which are currently well known in the art, as well as detection strategies which may evolve later. Examples of the foregoing presently known detection methods are hereby incorporated herein by reference. See, for example, Caskey et al., U.S. Pat. No. 5,582,989, Gelfand et al., U.S. Pat. No. 5,210,015. Examples of such detection methods include target amplification methods as well as signal amplification technologies. An example of presently known detection methods would include the nucleic acid amplification technologies referred to as PCR, LCR, NASBA, SDA, RCR and TMA. See, for example, Caskey et al., U.S. Pat. No. 5,582,989, Gelfand et al., U.S. Pat. No. 5,210,015. All of the foregoing are hereby incorporated by reference. Detection may also be accomplished using signal amplification such as that disclosed in Snitman et al., U.S. Pat. No. 5,273,882. While the amplification of target or signal is preferred at present, it is contemplated and within the scope of the present invention that ultrasensitive detection methods which do not require amplification can be utilized herein.

Detection, both amplified and non-amplified, may be (combined) carried out using a variety of heterogeneous and homogeneous detection formats. Examples of heterogeneous detection formats are disclosed in Snitman et al., U.S. Pat. No. 5,273,882, Albarella et al. in EP-84114441.9, Urdea et al., U.S. Pat. No. 5,124,246, Ullman et al. U.S. Pat. No. 5,185,243 and Kourilsky et al., U.S. Pat. No. 4,581,333. All of the foregoing are hereby incorporated by reference. Examples of homogeneous detection formats are disclosed in, Caskey et al., U.S. Pat. No. 5,582,989, Gelfand et al., U.S. Pat. No. 5,210,015, which are incorporated herein by reference. Also contemplated and within the scope of the present invention is the use of multiple probes in the hybridization assay, which use improves sensitivity and amplification of the CS193 signal. See, for example, Caskey et al., U.S. Pat. No. 5,582,989, Gelfand et al., U.S. Pat. No. 5,210,015, which are incorporated herein by reference.

In one embodiment, the present invention generally comprises the steps of contacting a test sample suspected of containing a target polynucleotide sequence with amplification reaction reagents comprising an amplification primer, and a detection probe that can hybridize with an internal region of the amplicon sequences. Probes and primers employed according to the method provided herein are labeled with capture and detection labels, wherein probes are labeled with one type of label and primers are labeled with another type of label. Additionally, the primers and probes are selected such that the probe sequence has a lower melt temperature than the primer sequences. The amplification reagents, detection reagents and test sample are placed under amplification conditions whereby, in the presence of target sequence, copies of the target sequence (an amplicon) are produced. In the usual case, the amplicon is double stranded because primers are provided to amplify a target sequence and its complementary strand. The double stranded amplicon then is thermally denatured to produce single stranded amplicon members. Upon formation of the single stranded amplicon members, the mixture is cooled to allow the formation of complexes between the probes and single stranded amplicon members.

As the single stranded amplicon sequences and probe sequences are cooled, the probe sequences preferentially bind the single stranded amplicon members. This finding is counterintuitive given that the probe sequences generally are selected to be shorter than the primer sequences and therefore have a lower melt temperature than the primers. Accordingly, the melt temperature of the amplicon produced by the primers should also have a higher melt temperature than the probes. Thus, as the mixture cools, the re-formation of the double stranded amplicon would be expected. As previously stated, however, this is not the case. The probes are found to preferentially bind the single stranded amplicon members. Moreover, this preference of probe/single stranded amplicon binding exists even when the primer sequences are added in excess of the probes.

After the probe/single stranded amplicon member hybrids are formed, they are detected. Standard heterogeneous assay formats are suitable for detecting the hybrids using the detection labels and capture labels present on the primers and probes. The hybrids can be bound to a solid phase reagent by virtue of the capture label and detected by virtue of the detection label. In cases where the detection label is directly detectable, the presence of the hybrids on the solid phase can be detected by causing the label to produce a detectable signal, if necessary, and detecting the signal. In cases where the label is not directly detectable, the captured hybrids can be contacted with a conjugate, which generally comprises a binding member attached to a directly detectable label. The conjugate becomes bound to the complexes and the conjugate's presence on the complexes can be detected with the directly detectable label. Thus, the presence of the hybrids on the solid phase reagent can be determined. Those skilled in the art will recognize that wash steps may be employed to wash away unhybridized amplicon or probe as well as unbound conjugate.

Although the target sequence is described as single stranded, it also is contemplated to include the case where the target sequence is actually double stranded but is merely separated from its complement prior to hybridization with the amplification primer sequences. In the case where PCR is employed in this method, the ends of the target sequences are usually known. In cases where LCR or a modification thereof is employed in the preferred method, the entire target sequence is usually known. Typically, the target sequence is a nucleic acid sequence such as, for example, RNA or DNA.

The method provided herein can be used in well-known amplification reactions that include thermal cycle reaction mixtures, particularly in PCR and gap LCR (GLCR). Amplification reactions typically employ primers to repeatedly generate copies of a target nucleic acid sequence, which target sequence is usually a small region of a much larger nucleic acid sequence. Primers are themselves nucleic acid sequences that are complementary to regions of a target sequence. Under amplification conditions, these primers hybridize or bind to the complementary regions of the target sequence. Copies of the target sequence typically are generated by the process of primer extension and/or ligation which utilizes enzymes with polymerase or ligase activity, separately or in combination, to add nucleotides to the hybridized primers and/or ligate adjacent probe pairs. The nucleotides that are added to the primers or probes, as monomers or preformed oligomers, are also complementary to the target sequence. Once the primers or probes have been sufficiently extended and/or ligated, they are separated from the target sequence, for example, by heating the reaction mixture to a "melt temperature" which is one in which complementary nucleic acid strands dissociate. Thus, a sequence complementary to the target sequence is formed.

A new amplification cycle then can take place to further amplify the number of target sequences by separating any double stranded sequences, allowing primers or probes to hybridize to their respective targets, extending and/or ligating the hybridized primers or probes and re-separating. The complementary sequences that are generated by amplification cycles can serve as templates for primer extension or filling the gap of two probes to further amplify the number of target sequences. Typically, a reaction mixture is cycled between 20 and 100 times, more typically, a reaction mixture is cycled between 25 and 50 times. The numbers of cycles can be determined by the routineer. In this manner, multiple copies of the target sequence and its complementary sequence are produced. Thus, primers initiate amplification of the target sequence when it is present under amplification conditions.

Generally, two primers which are complementary to a portion of a target strand and its complement are employed in PCR. For LCR, four probes, two of which are complementary to a target sequence and two of which are similarly complementary to the target's complement, are generally employed. In addition to the primer sets and enzymes previously mentioned, a nucleic acid amplification reaction mixture may also comprise other reagents which are well known and include but are not limited to: enzyme cofactors such as manganese; magnesium; salts; nicotinamide adenine dinucleotide (NAD); and deoxynucleotide triphosphates (dNTPs) such as, for example, deoxyadenine triphosphate, deoxyguanine triphosphate, deoxycytosine triphosphate and deoxythymine triphosphate.

While the amplification primers initiate amplification of the target sequence, the detection (or hybridization) probe is not involved in amplification. Detection probes are generally nucleic acid sequences or uncharged nucleic acid analogs such as, for example, peptide nucleic acids which are disclosed in International Publication No. WO 92/20702; morpholino analogs which are described in U.S. Pat. Nos. 5,185,444, 5,034,506 and 5,142,047; and the like. Depending upon the type of label carried by the probe, the probe is employed to capture or detect the amplicon generated by the amplification reaction. The probe is not involved in amplification of the target sequence and therefore may have to be rendered "non-extendible" in that additional dNTPs cannot be added to the probe. In and of themselves, analogs usually are non-extendible and nucleic acid probes can be rendered non-extendible by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified. U.S. patent application Ser. No. 07/049,061 filed Apr. 19, 1993 and incorporated herein by reference describes modifications which can be used to render a probe non-extendible.

The ratio of primers to probes is not important. Thus, either the probes or primers can be added to the reaction mixture in excess whereby the concentration of one would be greater than the concentration of the other. Alternatively, primers and probes can be employed in equivalent concentrations. Preferably, however, the primers are added to the reaction mixture in excess of the probes. Thus, primer to probe ratios of, for example, 5:1 and 20:1, are preferred.

While the length of the primers and probes can vary, the probe sequences are selected such that they have a lower melt temperature than the primer sequences. Hence, the primer sequences are generally longer than the probe sequences. Typically, the primer sequences are in the range of between 20 and 50 nucleotides long, more typically in the range of between 20 and 30 nucleotides long. The typical probe is in the range of between 10 and 25 nucleotides long.

Various methods for synthesizing primers and probes are well known in the art. Similarly, methods for attaching labels to primers or probes are also well known in the art. For example, it is a matter of routine to synthesize desired nucleic acid primers or probes using conventional nucleotide phosphoramidite chemistry and instruments available from Applied Biosystems, Inc., (Foster City, Calif.), Dupont (Wilmington, Del.), or Milligen (Bedford Mass.). Many methods have been described for labeling oligonucleotides such as the primers or probes of the present invention. Enzo Biochemical (New York, N.Y.) and Clontech (Palo Alto, Calif.) both have described and commercialized probe labeling techniques. For example, a primary amine can be attached to a 3' oligo terminus using 3'-Amine-ON CPG™ (Clontech, Palo Alto, Calif.). Similarly, a primary amine can be attached to a 5' oligo terminus using Aminomodifier II® (Clontech). The amines can be reacted to various haptens using conventional activation and linking chemistries. In addition, copending applications U.S. Ser. No. 625,566, filed Dec. 11, 1990 and Ser. No. 630,908, filed Dec. 20, 1990, which are each incorporated herein by reference, teach methods for labeling probes at their 5' and 3' termini, respectively. International Publication NOS WO 92/10505, published Jun. 25, 1992, and WO 92/11388, published Jul. 9, 1992, teach methods for labeling probes at their 5' and 3' ends, respectively. According to one known method for labeling an oligonucleotide, a label-phosphoramidite reagent is prepared and used to add the label to the oligonucleotide during its synthesis. See, for example, N. T. Thuong et al., *Tet. Letters* 29(46):5905–5908 (1988); or J. S. Cohen et al., published U.S. patent application Ser. No. 07/246,688 (NTIS ORDER No. PAT APPL Ser. No. 7/246,688) (1989). Preferably, probes are labeled at their 3' and 5' ends.

A capture label is attached to the primers or probes and can be a specific binding member which forms a binding pair with the solid phase reagent's specific binding member. It will be understood that the primer or probe itself may serve as the capture label. For example, in the case where a solid phase reagent's binding member is a nucleic acid sequence, it may be selected such that it binds a complementary portion of the primer or probe to thereby immobilize the primer or probe to the solid phase. In cases where the probe itself serves as the binding member, those skilled in the art will recognize that the probe will contain a sequence or "tail" that is not complementary to the single stranded amplicon members. In the case where the primer itself serves as the capture label, at least a portion of the primer will be free to hybridize with a nucleic acid on a solid phase because the probe is selected such that it is not fully complementary to the primer sequence.

Generally, probe/single stranded amplicon member complexes can be detected using techniques commonly employed to perform heterogeneous immunoassays. Preferably, in this embodiment, detection is performed according to the protocols used by the commercially available Abbott LCx® instrumentation (Abbott Laboratories, Abbott Park, Ill.).

The primers and probes disclosed herein are useful in typical PCR assays, wherein the test sample is contacted with a pair of primers, amplification is performed, the hybridization probe is added, and detection is performed.

Another method provided by the present invention comprises contacting a test sample with a plurality of polynucleotides, wherein at least one polynucleotide is a CS193 molecule as described herein, hybridizing the test sample with the plurality of polynucleotides and detecting hybridization complexes. Hybridization complexes are identified and quantitated to compile a profile which is indicative of GI tract tissue disease, such as GI tract cancer. Expressed RNA sequences may further be detected by reverse transcription and amplification of the DNA product by procedures well-known in the art, including polymerase chain reaction (PCR).

Drug Screening and Gene Therapy

The present invention also encompasses the use of gene therapy methods for the introduction of anti-sense CS193 derived molecules, such as polynucleotides or oligonucleotides of the present invention, into patients with conditions associated with abnormal expression of polynucleotides related to a GI tract tissue disease or condition especially GI tract cancer. These molecules, including antisense RNA and DNA fragments and ribozymes, are designed to inhibit the translation of CS193-mRNA, and may be used therapeutically in the treatment of conditions associated with altered or abnormal expression of CS193 polynucleotide.

Alternatively, the oligonucleotides described above can be delivered to cells by procedures known in the art such that the anti-sense RNA or DNA may be expressed in vivo to inhibit production of a CS193 polypeptide in the manner described above. Antisense constructs to a CS193 polynucleotide, therefore, reverse the action of CS193 transcripts and may be used for treating GI tract tissue disease conditions, such as GI tract cancer. These antisense constructs may also be used to treat tumor metastases.

The present invention also provides a method of screening a plurality of compounds for specific binding to CS193 polypeptide(s), or any fragment thereof, to identify at least one compound which specifically binds the CS193 polypeptide. Such a method comprises the steps of providing at least one compound; combining the CS193 polypeptide with each compound under suitable conditions for a time sufficient to allow binding; and detecting the CS193 polypeptide binding to each compound.

The polypeptide or peptide fragment employed in such a test may either be free in solution, affixed to a solid support, borne on a cell surface or located intracellularly. One method of screening utilizes eukaryotic or prokaryotic host cells which are stably transfected with recombinant nucleic acids which can express the polypeptide or peptide fragment. A drug, compound, or any other agent may be screened against such transfected cells in competitive binding assays. For example, the formation of complexes between a polypeptide and the agent being tested can be measured in either viable or fixed cells.

The present invention thus provides methods of screening for drugs, compounds, or any other agent which can be used to treat diseases associated with CS193. These methods comprise contacting the agent with a polypeptide or fragment thereof and assaying for either the presence of a complex between the agent and the polypeptide, or for the presence of a complex between the polypeptide and the cell. In competitive binding assays, the polypeptide typically is labeled. After suitable incubation, free (or uncomplexed) polypeptide or fragment thereof is separated from that present in bound form, and the amount of free or uncomplexed label is used as a measure of the ability of the particular agent to bind to the polypeptide or to interfere with the polypeptide/cell complex.

The present invention also encompasses the use of competitive screening assays in which neutralizing antibodies capable of binding polypeptide specifically compete with a test agent for binding to the polypeptide or fragment thereof. In this manner, the antibodies can be used to detect the presence of any polypeptide in the test sample which shares one or more antigenic determinants with a CS193 polypeptide as provided herein.

Another technique for screening provides high throughput screening for compounds having suitable binding affinity to at least one polypeptide of CS193 disclosed herein. Briefly, large numbers of different small peptide test compounds are synthesized on a solid phase, such as plastic pins or some other surface. The peptide test compounds are reacted with polypeptide and washed. Polypeptide thus bound to the solid phase is detected by methods well-known in the art. Purified polypeptide can also be coated directly onto plates for use in the screening techniques described herein. In addition, non-neutralizing antibodies can be used to capture the polypeptide and immobilize it on the solid support. See, for example, EP 84/03564, published on Sep. 13, 1984, which is incorporated herein by reference.

The goal of rational drug design is to produce structural analogs of biologically active polypeptides of interest or of the small molecules including agonists, antagonists, or inhibitors with which they interact. Such structural analogs can be used to design drugs which are more active or stable forms of the polypeptide or which enhance or interfere with the function of a polypeptide in vivo. J. Hodgson, *Bio/Technology* 9:19–21 (1991), incorporated herein by reference.

For example, in one approach, the three-dimensional structure of a polypeptide, or of a polypeptide-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous polypeptide-ike molecules or to identify efficient inhibitors.

Useful examples of rational drug design may include molecules which have improved activity or stability as shown by S. Braxton et al., *Biochemistry* 31:7796–7801 (1992), or which act as inhibitors, agonists, or antagonists of native peptides as shown by S. B. P. Athauda et al., *J Biochem.* (*Tokyo*) 113 (6):742–746 (1993), incorporated herein by reference.

It also is possible to isolate a target-specific antibody selected by an assay as described hereinabove, and then to determine its crystal structure. In principle this approach yields a pharmacophore upon which subsequent drug design can be based. It further is possible to bypass protein crystallography altogether by generating anti-idiotypic antibodies ("anti-ids") to a functional, pharmacologically active antibody. As a mirror image of a mirror image, the binding site of the anti-id is an analog of the original receptor. The anti-id then can be used to identify and isolate peptides from banks of chemically or biologically produced peptides. The isolated peptides then can act as the pharmacophore (that is, a prototype pharmaceutical drug).

A sufficient amount of a recombinant polypeptide of the present invention may be made available to perform analytical studies such as X-ray crystallography. In addition, knowledge of the polypeptide amino acid sequence which is derivable from the nucleic acid sequence provided herein will provide guidance to those employing computer modeling techniques in place of, or in addition to, x-ray crystallography.

Antibodies specific to a CS193 polypeptide (e.g., anti-CS193 antibodies) further may be used to inhibit the biological action of the polypeptide by binding to the polypeptide. In this manner, the antibodies may be used in therapy, for example, to treat GI tract tissue diseases including GI tract cancer and its metastases.

Further, such antibodies can detect the presence or absence of a CS193 polypeptide in a test sample and, therefore, are useful as diagnostic markers for the diagnosis of a GI tract tissue disease or condition especially GI tract cancer. Such antibodies may also function as a diagnostic marker for GI tract tissue disease conditions, such as GI tract cancer.

The present invention also is directed to antagonists and inhibitors of the polypeptides of the present invention. The antagonists and inhibitors are those which inhibit or eliminate the function of the polypeptide. Thus, for example, an antagonist may bind to a polypeptide of the present invention and inhibit or eliminate its function. The antagonist, for example, could be an antibody against the polypeptide which eliminates the activity of a CS193 polypeptide by binding a CS193 polypeptide, or in some cases the antagonist may be an oligonucleotide. Examples of small molecule inhibitors include, but are not limited to, small peptides or peptide-like molecules.

The antagonists and inhibitors may be employed as a composition with a pharmaceutically acceptable carrier including, but not limited to, saline, buffered saline, dextrose, water, glycerol, ethanol and combinations thereof. Administration of CS193 polypeptide inhibitors is preferably systemic. The present invention also provides an antibody which inhibits the action of such a polypeptide.

Antisense technology can be used to reduce gene expression through triple-helix formation or antisense DNA or RNA, both of which methods are based on binding of a polynucleotide to DNA or RNA. For example, the 5' coding portion of the polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription, thereby preventing transcription and the production of the CS193 polypeptide. For triple helix, see, for example, Lee et al., *Nuc. Acids Res.* 6:3073 (1979); Cooney et al., *Science* 241:456 (1988); and Dervan et al., *Science* 251:1360 (1991) The antisense RNA oligonucleotide hybridizes to the mRNA in vivo and blocks translation of a mRNA molecule into the CS193 polypeptide. For antisense, see, for example, Okano, *J. Neurochem.* 56:560 (1991); and "Oligodeoxynucleotides as Antisense Inhibitors of Gene Expression," CRC Press, Boca Raton, Fla. (1988). Antisense oligonucleotides act with greater efficacy when modified to contain artificial internucleotide linkages which render the molecule resistant to nucleolytic cleavage. Such artificial internucleotide linkages include, but are not limited to, methylphosphonate, phosphorothiolate and phosphoroamydate internucleotide linkages.

Recombinant Technology

The present invention provides host cells and expression vectors comprising CS193 polynucleotides of the present invention and methods for the production of the polypeptide (s) they encode. Such methods comprise culturing the host cells under conditions suitable for the expression of the CS193 polynucleotide and recovering the CS193 polypeptide from the cell culture.

The present invention also provides vectors which include CS193 polynucleotides of the present invention, host cells which are genetically engineered with vectors of the present invention and the production of polypeptides of the present invention by recombinant techniques.

Host cells are genetically engineered (transfected, transduced or transformed) with the vectors of this invention which may be cloning vectors or expression vectors. The vector may be in the form of a plasmid, a viral particle, a phage, etc. The engineered host cells can be cultured in conventional nutrient media modified as appropriate for activating promoters, selecting transfected cells, or amplifying CS193 gene(s). The culture conditions, such as temperature, pH and the like, are those previously used with the host cell selected for expression, and will be apparent to the ordinarily skilled artisan.

The polynucleotides of the present invention may be employed for producing a polypeptide by recombinant techniques. Thus, the polynucleotide sequence may be included in any one of a variety of expression vehicles, in particular, vectors or plasmids for expressing a polypeptide. Such vectors include chromosomal, nonchromosomal and synthetic DNA sequences; e.g., derivatives of SV40; bacterial plasmids; phage DNA; yeast plasmids; vectors derived from combinations of plasmids and phage DNA, viral DNA such as vaccinia, adenovirus, fowl pox virus and pseudorabies. However, any other plasmid or vector may be used so long as it is replicable and viable in the host.

The appropriate DNA sequence may be inserted into the vector by a variety of procedures. In general, the DNA sequence is inserted into appropriate restriction endonuclease sites by procedures known in the art. Such procedures and others are deemed to be within the scope of those skilled in the art. The DNA sequence in the expression vector is operatively linked to an appropriate expression control sequence(s) (promoter) to direct mRNA synthesis. Representative examples of such promoters include, but are not limited to, the LTR or the SV40 promoter, the *E. coli* lac or trp, the phage lambda P sub L promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. In addition, the expression vectors preferably contain a gene to provide a phenotypic trait for selection of transfected host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transfect an appropriate host to permit the host to express the protein. As representative examples of appropriate hosts, there may be mentioned: bacterial cells, such as *E. coli, Salmonella typhimurium*; Streptomvces sp.; fungal cells, such as yeast; insect cells, such as Drosophila and Sf9; animal cells, such as CHO, COS or Bowes melanoma; plant cells, etc. The selection of an appropriate host is deemed to be within the scope of those skilled in the art from the teachings provided herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences including, for example, a promoter, operably linked to the sequence. Large numbers of suitable vectors and promoters are known to those of skill in the art and are commercially available. The following vectors are provided by way of example. Bacterial: pINCY (Incyte Pharmaceuticals Inc., Palo Alto, Calif.), pSPORT1 (Life Technologies, Gaithersburg, Md.), pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223-3, pKK233-3, pDR540, pRIT5 (Pharmacia); Eukaryotic: pWLneo, pSV2cat, pOG44, pXT1, pSG (Stratagene) pSVK3, pBPV, pMSG, pSVL (Pharmacia). However, any other plasmid or vector may be used as long as it is replicable and viable in the host.

Plasmid pINCY is generally identical to the plasmid pSPORT1 (available from Life Technologies, Gaithersburg, Md.) with the exception that it has two modifications in the polylinker (multiple cloning site). These modifications are (1) it lacks a HindIII restriction site and (2) its EcoRI restriction site lies at a different location. pINCY is created from pSPORT1 by cleaving pSPORT1 with both HindIII and EcoRI and replacing the excised fragment of the polylinker with synthetic DNA fragments (SEQUENCE ID NO 19 and SEQUENCE ID NO 20). This replacement may be made in any manner known to those of ordinary skill in the art. For example, the two nucleotide sequences, SEQUENCE ID NO 19 and SEQUENCE ID NO 20, may be generated synthetically with 5' terminal phosphates, mixed together, and then ligated under standard conditions for performing staggered end ligations into the pSPORT1 plasmid cut with HindIII and EcoRI. Suitable host cells (such as *E. coli* DH5$\mu$ cells) then are transfected with the ligated DNA and recombinant clones are selected for ampicillin resistance. Plasmid DNA then is prepared from individual clones and subjected to restriction enzyme analysis or DNA sequencing in order to confirm the presence of insert sequences in the proper orientation. Other cloning strategies known to the ordinary artisan also may be employed.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, SP6, T7, gpt, lambda P sub R, P sub L and trp. Eukaryotic promoters include cytomegalovirus (CMV) immediate early, herpes simplex virus (HSV) thymidine kinase, early and late SV40, LTRs from retroviruses and mouse metallothionein-I. Selection of the appropriate vector and promoter is well within the level of ordinary skill in the art.

In a further embodiment, the present invention provides host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (L. Davis et al., "Basic Methods in Molecular Biology," 2nd edition, Appleton and Lang, Paramount Publishing, East Norwalk, Conn. (1994)).

The constructs in host cells can be used in a conventional manner to produce the gene product encoded by the recombinant sequence. Alternatively, the polypeptides of the invention can be synthetically produced by conventional peptide synthesizers.

Recombinant proteins can be expressed in mammalian cells, yeast, bacteria, or other cells, under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual*, Second Edition, (Cold Spring Harbor, N.Y., 1989), which is hereby incorporated by reference.

Transcription of a DNA encoding the polypeptide(s) of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin and adenovirus enhancers.

Generally, recombinant expression vectors will include origins of replication and selectable markers permitting transfection of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transfection include *E. coli, Bacillus subtilis, Salmonella typhimurium* and various species within the genera Pseudomonas, Streptomyces and Staphylococcus, although others may also be employed as a routine matter of choice.

Useful expression vectors for bacterial use comprise a selectable marker and bacterial origin of replication derived from plasmids comprising genetic elements of the well-known cloning vector pBR322 (ATCC 37017). Other vectors include but are not limited to PKK223-3 (Pharmacia Fine Chemicals, Uppsala, Sweden) and GEM1 (Promega Biotec, Madison, Wis.). These pBR322 "backbone" sections are combined with an appropriate promoter and the structural sequence to be expressed.

Following transfection of a suitable host and growth of the host to an appropriate cell density, the selected promoter is derepressed by appropriate means (e.g., temperature shift or chemical induction), and cells are cultured for an additional period. Cells are typically harvested by centrifugation, disrupted by physical or chemical means, and the resulting crude extract retained for further purification. Microbial cells employed in expression of proteins can be disrupted by any convenient method including freeze-thaw cycling, sonication, mechanical disruption, or use of cell lysing agents. Such methods are well-known to the ordinary artisan.

Various mammalian cell culture systems can also be employed to express recombinant protein. Examples of mammalian expression systems include the COS-7 lines of monkey kidney fibroblasts described by Gluzman, *Cell* 23:175 (1981), and other cell lines capable of expressing a compatible vector, such as the C127, HEK-293, 3T3, CHO, HeLa and BHK cell lines. Mammalian expression vectors will comprise an origin of replication, a suitable promoter and enhancer and also any necessary ribosome binding sites, polyadenylation sites, splice donor and acceptor sites, transcriptional termination sequences and 5' flanking nontranscribed sequences. DNA sequences derived from the SV40 viral genome, for example, SV40 origin, early promoter, enhancer, splice, and polyadenylation sites may be used to provide the required nontranscribed genetic elements. Representative, useful vectors include pRc/CMV and pcDNA3 (available from Invitrogen, San Diego, Calif.).

CS193 polypeptides are recovered and purified from recombinant cell cultures by known methods including affinity chromatography, ammonium sulfate or ethanol precipitation, acid extraction, anion or cation exchange chromatography, phosphocellulose chromatography, hydrophobic interaction chromatography, hydroxyapatite chromatography or lectin chromatography. It is preferred to have low concentrations (approximately 0.1–5 mM) of calcium ion present during purification (Price, et al., *J. Biol. Chem.* 244:917 (1969)). Protein refolding steps can be used, as necessary, in completing configuration of the polypeptide. Finally, high performance liquid chromatography (HPLC) can be employed for final purification steps.

Thus, polypeptides of the present invention may be naturally purified products expressed from a high expressing cell line, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. The polypeptides of the invention may also include an initial methionine amino acid residue.

The starting plasmids can be constructed from available plasmids in accord with published, known procedures. In addition, equivalent plasmids to those described are known in the art and will be apparent to one of ordinary skill in the art.

The following is the general procedure for the isolation and analysis of cDNA clones. In a particular embodiment disclosed herein, mRNA was isolated from GI tract tissue and used to generate the cDNA library. GI tract tissue was obtained from patients by surgical resection and was classified as tumor or non-tumor tissue by a pathologist.

The cDNA inserts from random isolates of the GI tract tissue libraries were sequenced in part, analyzed in detail as set forth in the Examples and are disclosed in the Sequence Listing as SEQUENCE ID NOS 1–15. Also analyzed in detail as set forth in the Examples, and disclosed in the Sequence Listing, are the full-length sequences of clones 774134 and 774419 (referred to as clones 774134IH and 774419IH (SEQUENCE ID NOS 16 and 17, respectively)). The consensus sequence of these inserts is presented as SEQUENCE ID NO 18. These polynucleotides may contain an entire open reading frame with or without associated regulatory sequences for a particular gene, or they may encode only a portion of the gene of interest. This is attributed to the fact that many genes are several hundred and sometimes several thousand bases in length and, with current technology, cannot be cloned in their entirety because of vector limitations, incomplete reverse transcription of the first strand, or incomplete replication of the second strand. Contiguous, secondary clones containing additional nucleotide sequences may be obtained using a variety of methods known to those of skill in the art.

Methods for DNA sequencing are well known in the art. Conventional enzymatic methods employ DNA polymerase, Klenow fragment, Sequenase (US Biochemical Corp, Cleveland, Ohio) or Taq polymerase to extend DNA chains from an oligonucleotide primer annealed to the DNA template of interest. Methods have been developed for the use of both single-stranded and double-stranded templates. The chain termination reaction products may be electrophoresed on urea/polyacrylamide gels and detected either by autoradiography (for radionucleotide labeled precursors) or by fluorescence (for fluorescent-labeled precursors). Recent improvements in mechanized reaction preparation, sequencing and analysis using the fluorescent detection method have permitted expansion in the number of sequences that can be determined per day using machines such as the Applied Biosystems 377 DNA Sequencers (Applied Biosystems, Foster City, Calif.).

The reading frame of the nucleotide sequence can be ascertained by several types of analyses. First, reading frames contained within the coding sequence can be analyzed for the presence of start codon ATG and stop codons TGA, TAA or TAG. Typically, one reading frame will continue throughout the major portion of a cDNA sequence while other reading frames tend to contain numerous stop codons. In such cases, reading frame determination is straightforward. In other more difficult cases, further analysis is required.

Algorithms have been created to analyze the occurrence of individual nucleotide bases at each putative codon triplet. See, for example J. W. Fickett, *Nuc. Acids Res.* 10:5303 (1982). Coding DNA for particular organisms (bacteria, plants and animals) tends to contain certain nucleotides within certain triplet periodicities, such as a significant preference for pyrimidines in the third codon position. These preferences have been incorporated into widely available software which can be used to determine coding potential (and frame) of a given stretch of DNA. The algorithm-derived information combined with start/stop codon information can be used to determine proper frame with a high degree of certainty. This, in turn, readily permits cloning of the sequence in the correct reading frame into appropriate expression vectors.

The nucleic acid sequences disclosed herein may be joined to a variety of other polynucleotide sequences and vectors of interest by means of well-established recombinant DNA techniques. See J. Sambrook et al., supra. Vectors of interest include cloning vectors, such as plasmids, cosmids, phage derivatives, phagernids, as well as sequencing, replication and expression vectors, and the like. In general, such vectors contain an origin of replication functional in at least one organism, convenient restriction endonuclease digestion sites and selectable markers appropriate for particular host cells. The vectors can be transferred by a variety of means known to those of skill in the art into suitable host cells which then produce the desired DNA, RNA, or polypeptides.

Occasionally, sequencing or random reverse transcription errors will mask the presence of the appropriate open reading frame or regulatory element. In such cases, it is possible to determine the correct reading frame by attempting to express the polypeptide and determining the amino acid sequence by standard peptide mapping and sequencing techniques. See, F. M. Ausubel et al., *Current Protocols in Molecular Biology*, John Wiley & Sons, New York, N.Y. (1989). Additionally, the actual reading frame of a given nucleotide sequence may be determined by transfection of host cells with vectors containing all three potential reading frames. Only those cells with the nucleotide sequence in the correct reading frame will produce a peptide of the predicted length.

The nucleotide sequences provided herein have been prepared by current, state-of-the-art, automated methods and, as such, may contain unidentified nucleotides. These will not present a problem to those skilled in the art who wish to practice the invention. Several methods employing standard recombinant techniques, described in J. Sambrook (supra) or periodic updates thereof, may be used to complete the missing sequence information. The same techniques used for obtaining a full length sequence, as described herein, may be used to obtain nucleotide sequences.

Expression of a particular cDNA may be accomplished by subcloning the cDNA into an appropriate expression vector and transfecting this vector into an appropriate expression host. The cloning vector used for the generation of the GI tract tissue cDNA library can be used for transcribing mRNA of a particular cDNA and contains a promoter for beta-galactosidase, an amino-terminal met and the subsequent seven amino acid residues of beta-galactosidase. Immediately following these eight residues is an engineered bacteriophage promoter useful for artificial priming and transcription, as well as a number of unique restriction sites, including EcoRI, for cloning. The vector can be transfected into an appropriate host strain of *E. coli.*

Induction of the isolated bacterial strain with isopropylthiogalactoside (IPTG) using standard methods will produce a fusion protein which contains the first seven residues of beta-galactosidase, about 15 residues of linker and the peptide encoded within the cDNA. Since cDNA clone inserts are generated by an essentially random process, there is one chance in three that the included cDNA will lie in the correct frame for proper translation. If the cDNA is not in the proper reading frame, the correct frame can be obtained by deletion or insertion of an appropriate number of bases by well known methods including in vitro mutagenesis, digestion with exonuclease III or mung bean nuclease, or oligonucleotide linker inclusion.

The cDNA can be shuttled into other vectors known to be useful for expression of protein in specific hosts. Oligonucleotide primers containing cloning sites and segments of DNA sufficient to hybridize to stretches at both ends of the target cDNA can be synthesized chemically by standard methods. These primers can then be used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include, but are not limited to, mammalian cells, such as Chinese Hamster Ovary (CHO) and human embryonic kidney (HEK) 293 cells, insect cells, such as Sf9 cells, yeast cells, such as *Saccharomyces cerevisiae* and bacteria, such as *E. coli*. For each of these cell systems, a useful expression vector may also include an origin of replication to allow propagation in bacteria and a selectable marker such as the beta-lactamase antibiotic resistance gene to allow selection in bacteria. In addition, the vectors may include a second selectable marker, such as the neomycin phosphotransferase gene, to allow selection in transfected eukaryotic host cells. Vectors for use in eukaryotic expression hosts may require the addition of 3' poly A tail if the sequence of interest lacks poly A.

Additionally, the vector may contain promoters or enhancers which increase gene expression. Such promoters are host specific and include, but are not limited to, MMTV, SV40, or metallothionine promoters for CHO cells; trp, lac, tac or T7 promoters for bacterial hosts; or alpha factor, alcohol oxidase or PGH promoters for yeast. Adenoviral vectors with or without transcription enhancers, such as the Rous sarcoma virus (RSV) enhancer, may be used to drive protein expression in mammalian cell lines. Once homogeneous cultures of recombinant cells are obtained, large quantities of recombinantly produced protein can be recovered from the conditioned medium and analyzed using chromatographic methods well known in the art. An alternative method for the production of large amounts of secreted protein involves the transfection of mammalian embryos and the recovery of the recombinant protein from milk produced by transgenic cows, goats, sheep, etc. Polypeptides and closely related molecules may be expressed recombinantly in such a way as to facilitate protein purification. One approach involves expression of a chimeric protein which includes one or more additional polypeptide domains not naturally present on human polypeptides. Such purification-facilitating domains include, but are not limited to, metal-chelating peptides such as histidine-tryptophan domains that allow purification on immobilized metals, protein A domains that allow purification on immobilized immunoglobulin and the domain utilized in the FLAGS extension/affinity purification system (Immunex Corp, Seattle, Wash.). The inclusion of a cleavable linker sequence such as Factor XA or enterokinase from Invitrogen (San Diego, Calif.) between the polypeptide sequence and the purification domain may be useful for recovering the polypeptide.

Immunoassays

CS193 polypeptides, including fragments, derivatives, and analogs thereof, or cells expressing such polypeptides, can be utilized in a variety of assays, many of which are described herein, for the detection of antibodies to GI tract tissue. They also can be used as immunogens to produce antibodies. These antibodies can be, for example, polyclonal or monoclonal antibodies, chimeric, single chain and humanized antibodies, as well as Fab fragments, or the product of an Fab expression library. Various procedures known in the art may be used for the production of such antibodies and fragments.

For example, antibodies generated against a polypeptide comprising a sequence of the present invention can be obtained by direct injection of the polypeptide into an animal or by administering the polypeptide to an animal such as a mouse, rabbit, goat or human. A mouse, rabbit or goat is preferred. The polypeptide is selected from the group consisting of SEQUENCE ID NOS 41–49, and fragments thereof. The antibody so obtained then will bind the polypeptide itself. In this manner, even a sequence encoding only a fragment of the polypeptide can be used to generate antibodies that bind the native polypeptide. Such antibodies then can be used to isolate the polypeptide from test samples such as tissue suspected of containing that polypeptide. For preparation of monoclonal antibodies, any technique which provides antibodies produced by continuous cell line cultures can be used. Examples include the hybridoma technique as described by Kohler and Milstein, *Nature* 256:495–497 (1975), the trioma technique, the human B-cell hybridoma technique as described by Kozbor et al, *Immun. Today* 4:72 (1983) and the EBV-hybridoma technique to produce human monoclonal antibodies as described by Cole et al., in *Monoclonal Antibodies and Cancer Therapy*, Alan R. Liss, Inc, New York, N.Y., pp. 77–96 (1985). Techniques described for the production of single chain antibodies can be adapted to produce single chain antibodies to immunogenic polypeptide products of this invention. See, for example, U.S. Pat. No. 4,946,778, which is incorporated herein by reference.

Various assay formats may utilize the antibodies of the present invention, including "sandwich" immunoassays and probe assays. For example, the antibodies of the present invention, or fragments thereof, can be employed in various assay systems to determine the presence, if any, of CS193 antigen in a test sample. For example, in a first assay format, a polyclonal or monoclonal antibody or fragment thereof, or a combination of these antibodies, which has been coated on a solid phase, is contacted with a test sample, to form a first mixture. This first mixture is incubated for a time and under conditions sufficient to form antigen/antibody complexes. Then, an indicator reagent comprising a monoclonal or a polyclonal antibody or a fragment thereof, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of CS193 antigen in the test sample and captured on the solid phase, if any, is determined by detecting the measurable signal generated by the signal generating compound. The amount of CS193 antigen present in the test sample is proportional to the signal generated.

In an alternative assay format, a mixture is formed by contacting: (1) a polyclonal antibody, monoclonal antibody, or fragment thereof, which specifically binds to CS193 antigen, or a combination of such antibodies bound to a solid support; (2) the test sample; and (3) an indicator reagent comprising a monoclonal antibody, polyclonal antibody, or fragment thereof, which specifically binds to a different CS193 antigen (or a combination of these antibodies) to which a signal generating compound is attached. This mixture is incubated for a time and under conditions sufficient to form antibody/antigen/antibody complexes. The presence, if any, of CS193 antigen present in the test sample and captured on the solid phase is determined by detecting the measurable signal generated by the signal generating compound. The amount of CS193 antigen present in the test sample is proportional to the signal generated.

In another assay format, one or a combination of at least two monoclonal antibodies of the invention can be employed as a competitive probe for the detection of antibodies to CS193 antigen. For example, CS193 polypeptides such as the recombinant antigens disclosed herein, either alone or in combination, are coated on a solid phase. A test sample suspected of containing antibody to CS193 antigen then is incubated with an indicator reagent comprising a signal generating compound and at least one monoclonal antibody of the invention for a time and under conditions sufficient to form antigen/antibody complexes of either the test sample and indicator reagent bound to the solid phase or the indicator reagent bound to the solid phase. The reduction in binding of the monoclonal antibody to the solid phase can be quantitatively measured.

In yet another detection method, each of the monoclonal or polyclonal antibodies of the present invention can be employed in the detection of CS193 antigens in tissue sections, as well as in cells, by immunohistochemical analysis. Cytochemical analysis wherein these antibodies are labeled directly (with, for example, fluorescein, colloidal gold, horseradish peroxidase, alkaline phosphatase, etc.) or are labeled by using secondary labeled anti-species antibodies (with various labels as exemplified herein) to track the histopathology of disease also are within the scope of the present invention.

In addition, these monoclonal antibodies can be bound to matrices similar to CNBr-activated Sepharose and used for the affinity purification of specific CS193 polypeptides from cell cultures or biological tissues such as to purify recombinant and native CS193 proteins.

The monoclonal antibodies of the invention also can be used for the generation of chimeric antibodies for therapeutic use, or other similar applications.

The monoclonal antibodies or fragments thereof can be provided individually to detect CS193 antigens. Combinations of the monoclonal antibodies (and fragments thereof) provided herein also may be used together as components in a mixture or "cocktail" of at least one CS193 antibody of the invention, along with antibodies which specifically bind to other CS193 regions, each antibody having different binding specificities. Thus, this cocktail can include the monoclonal antibodies of the invention which are directed to CS193 polypeptides disclosed herein and other monoclonal antibodies specific to other antigenic determinants of CS193 antigens or other related proteins.

The polyclonal antibody or fragment thereof which can be used in the assay formats should specifically bind to a CS193 polypeptide or other CS193 polypeptides additionally used in the assay. The polyclonal antibody used preferably is of mammalian origin such as, human, goat, rabbit or sheep polyclonal antibody which binds CS193 polypeptide. Most preferably, the polyclonal antibody is of rabbit origin. The polyclonal antibodies used in the assays can be used either alone or as a cocktail of polyclonal antibodies. Since the cocktails used in the assay formats are comprised of either monoclonal antibodies or polyclonal antibodies having different binding specificity to CS193 polypeptides, they are useful for the detecting, diagnosing, staging, monitoring, prognosticating, preventing or treating, or determining the predisposition to, diseases and conditions of the GI tract, such as GI tract cancer.

It is contemplated and within the scope of the present invention that CS193 antigen may be detectable in assays by use of a recombinant antigen as well as by use of a synthetic peptide or purified peptide, which peptide comprises an amino acid sequence of CS193. The amino acid sequence of such a polypeptide is selected from the group consisting of SEQUENCE ID NOS 41–49, and fragments thereof. It also is within the scope of the present invention that different synthetic, recombinant or purified peptides, identifying different epitopes of CS193, can be used in combination in an assay for the detecting, diagnosing, staging, monitoring, prognosticating, preventing or treating, or determining the predisposition to diseases and conditions of the GI tract, such as GI tract cancer. In this case, all of these peptides can be coated onto one solid phase. Alternatively, each separate peptide may be coated onto separate solid phases, such as microparticles, and then combined to form a mixture of peptides which can be later used in assays. Furthermore, it is contemplated that multiple peptides which define epitopes from different antigens may be used for the detection, diagnosis, staging, monitoring, prognosis, prevention or treatment of, or determining the predisposition to, diseases and conditions of the GI tract, such as GI tract cancer. Peptides coated on solid phases or labeled with detectable labels are then allowed to compete with those present in a patient sample (if any) for a limited amount of antibody. A reduction in binding of the synthetic, recombinant, or purified peptides to the antibody (or antibodies) is an indication of the presence of CS193 antigen in the patient sample. The presence of CS193 antigen indicates the presence of GI tract tissue disease, especially GI tract cancer, in the patient. Variations of assay formats are known to those of ordinary skill in the art and many are discussed herein below.

In another assay format, the presence of anti-CS193 antibody and/or CS193 antigen can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/second analyte complexes. These so-formed complexes then are contacted with an indicator reagent comprising a member of a binding pair specific for the first analyte labeled with a signal generating compound and an indicator reagent comprising a member of a binding pair specific for the second analyte labeled with a signal generating compound to form a second mixture. This second mixture is incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one or more analytes in the test sample. In this assay format, recombinant antigens derived from the expression systems disclosed herein may be utilized, as well as monoclonal antibodies produced from the proteins derived from the expression systems as disclosed herein. For example, in this assay system, CS193 antigen can be the first analyte. Such assay systems are described in greater detail in EP Publication No. 0473065.

In yet other assay formats, the polypeptides disclosed herein may be utilized to detect the presence of antibody against CS193 antigen in test samples. For example, a test sample is incubated with a solid phase to which at least one polypeptide such as a recombinant protein or synthetic peptide has been attached. The polypeptide is selected from the group consisting of SEQUENCE ID NOS 41–49, and fragments thereof. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a recombinant protein produced as described herein is attached, and also is contacted with a monoclonal or polyclonal antibody specific for the protein, which preferably has been labeled with an indicator reagent. After incubation for a time and under conditions sufficient for antibody/antigen complexes to form, the solid phase is separated from the free phase, and the label is detected in either the solid or free phase as an indication of the presence of antibody against CS193 antigen. Other assay formats utilizing the recombinant antigens disclosed herein are contemplated. These include contacting a test sample with a solid phase to which at least one antigen from a first source has been attached, incubating the solid phase and test sample for a time and under conditions sufficient to form antigen/antibody complexes, and then contacting the solid phase with a labeled antigen, which antigen is derived from a second source different from the first source. For example, a recombinant protein derived from a first source such as *E. coli* is used as a capture antigen on a solid phase, a test sample is added to the so-prepared solid phase, and following standard incubation and washing steps as deemed or required, a recombinant protein derived from a different source (i.e., non-*E. coli* is utilized as a part of an indicator reagent which subsequently is detected. Likewise, combinations of a recombinant antigen on a solid phase and synthetic peptide in the indicator phase also are possible. Any assay format which utilizes an antigen specific for CS193 produced or derived from a first source as the capture antigen and an antigen specific for CS193 from a different second source is contemplated. Thus, various combinations of recombinant antigens, as well as the use of synthetic peptides, purified proteins and the like, are within the scope of this invention. Assays such as this and others are described in U.S. Pat. No. 5,254,458, which enjoys common ownership and is incorporated herein by reference.

Other embodiments which utilize various other solid phases also are contemplated and are within the scope of this invention. For example, ion capture procedures for immobilizing an immobilizable reaction complex with a negatively charged polymer (described in EP publication 0326100 and EP publication No. 0406473), can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemiluminescent signal measurements as described in EPO Publication No. 0 273,115.

Also, the methods of the present invention can be adapted for use in systems which utilize microparticle technology including automated and semi-automated systems wherein the solid phase comprises a microparticle (magnetic or non-magnetic). Such systems include those described in, for example, published EPO applications NOS. EP 0 425 633 and EP 0 424 634, respectively.

The use of scanning probe microscopy (SPM) for immunoassays also is a technology to which the monoclonal antibodies of the present invention are easily adaptable. In scanning probe microscopy, particularly in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Also, polyelectrolyte interactions may be used to immobilize a specific binding partner on a surface of a test piece by using techniques and chemistries. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

While the present invention discloses the preference for the use of solid phases, it is contemplated that the reagents such as antibodies, proteins and peptides of the present invention can be utilized in non-solid phase assay systems. These assay systems are known to those skilled in the art, and are considered to be within the scope of the present invention.

It is contemplated that the reagent employed for the assay can be provided in the form of a test kit with one or more containers such as vials or bottles, with each container containing a separate reagent such as a probe, primer, monoclonal antibody or a cocktail of monoclonal antibodies, or a polypeptide (e.g. recombinantly, synthetically produced or purified) employed in the assay. The polypeptide is selected from the group consisting of SEQUENCE ID NOS 41–49, and fragments thereof. Other components such as buffers, controls and the like, known to those of ordinary skill in art, may be included in such test kits. It also is contemplated to provide test kits which have means for collecting test samples comprising accessible body fluids, e.g., blood, urine, saliva and stool. Such tools useful for collection ("collection materials") include lancets and absorbent paper or cloth for collecting and stabilizing blood; swabs for collecting and stabilizing saliva; cups for collecting and stabilizing urine or stool samples. Collection materials, papers, cloths, swabs, cups and the like, may optionally be treated to avoid denaturation or irreversible adsorption of the sample. The collection materials also may be treated with or contain preservatives, stabilizers or antimicrobial agents to help maintain the integrity of the specimens. Test kits designed for the collection, stabilization and preservation of test specimens obtained by surgery or needle biopsy are also useful. It is contemplated that all kits may be configured in two components which can be provided separately; one component for collection and transport of the specimen and the other component for the analysis of the specimen. The collection component, for example, can be provided to the open market user while the components for analysis can be provided to others such as laboratory personnel for determination of the presence, absence or amount of analyte. Further, kits for the collection, stabilization and preservation of test specimens may be configured for use by untrained personnel and may be available in the open market for use at home with subsequent transportation to a laboratory for analysis of the test sample.

E. coli bacterium (clone 774134 and clone 774419) were deposited with the American Type Culture Collection (A.T.C.C.), 12301 Parklawn Drive, Rockville, Md. 20852, on Sep. 12, 1997 and Jun. 25, 1997, respectively, under the terms of the Budapest Treaty, and will be maintained for a period of thirty (30) years from the date of deposit, or for five (5) years after the last request for the deposit, or for the enforceable period of the U.S. patent, whichever is longer. These deposits, and any other deposited material described herein, are provided for convenience only and are not required to practice the present invention in view of the teachings provided herein. The cDNA sequence in all of the deposited material is incorporated herein by reference. Clones 774134 and 774419 were accorded A.T.C.C. Deposit NOS. 98543 and 98484, respectively.

The present invention will now be described by way of examples, which are meant to illustrate, but not to limit, the scope of the present invention.

EXAMPLES

Example 1

Identification of Gastrointestinal Tract Tissue Library CS193 Gene-Specific Clones A. Library Comparison of Expressed Sequence Tags (ESTs) or Transcript Images Partial sequences of cDNA clone inserts, so-called "expressed sequence tags" (ESTs), were derived from cDNA libraries made from GI tract tumor tissues, GI tract non-tumor tissues and numerous other tissues, both tumor and non-tumor and entered into a database (LIFESEQ™ database, available from Incyte Pharmaceuticals, Palo Alto, Calif.) as gene transcript images. See International Publication No. WO 95/20681. (A transcript image is a listing of the number of EST's for each of the represented genes in a given tissue library. ESTs sharing regions of mutual sequence overlap are classified into clusters. A cluster is assigned a clone number from a representative 5' EST. Often, a cluster of interest can be extended by comparing its consensus sequence with sequences of other EST's which did not meet the criteria for automated clustering. The alignment of all available clusters and single ESTs represent a contig from which a consensus sequence is derived.) The transcript images then were evaluated to identify EST sequences that were representative primarily of the GI tract tissue libraries. These target clones then were ranked according to their abundance (occurrence) in the target libraries and their absence from background libraries. Higher abundance clones with low background occurrence were given higher study priority. ESTs corresponding to the consensus sequence of CS193 (SEQUENCE ID NO 18, and fragments or complements thereof) were found in 28.6% (10 of 35) of GI tract tissue libraries. ESTs corresponding to the consensus sequence of CS193 (SEQUENCE ID NO 18, and fragments or complements thereof) were found in 0.35% (1 of 288) of the other, non-GI tract, libraries of the data base. Therefore, the consensus sequence or fragment thereof was found more than 82 times more often in GI tract than non-GI tract tissues. Overlapping clones 2767646 (SEQUENCE ID NO 1), 774134 (SEQUENCE ID NO 2), 775437 (SEQUENCE ID NO 3), 1281329 (SEQUENCE ID NO 4), 1628677 (SEQUENCE ID NO 5), 1286372 (SEQUENCE ID NO 6), 774419 (SEQUENCE ID NO 7), 3233118 (SEQUENCE ID NO 8), 2733923 (SEQUENCE ID NO 9), 906605 (SEQUENCE ID NO 10), 2771475 (SEQUENCE ID NO 11), 1803247 (SEQUENCE ID NO 12), 1737526 (SEQUENCE ID NO 13), 2792957 (SEQUENCE ID NO 14), and 1226186 (SEQUENCE ID NO 15) were identified for further study. These represented the minimum number of clones that were needed to form the contig and from which, along with the full-length sequence clones 774134IH and 774419IH (SEQUENCE ID NO 16 and SEQUENCE ID NO 17, respectively), the consensus sequence provided herein (SEQUENCE ID NO 18) was derived.

B. Generation of a Consensus Sequence

The nucleotide sequences of clones 2767646 (SEQUENCE ID NO 1), 774134 (SEQUENCE ID NO 2), 775437 (SEQUENCE ID NO 3), 1281329 (SEQUENCE ID NO 4), 1628677 (SEQUENCE ID NO 5), 1286372 (SEQUENCE ID NO 6), 774419 (SEQUENCE ID NO 7), 3233118 (SEQUENCE ID NO 8), 2733923 (SEQUENCE ID NO 9), 906605 (SEQUENCE ID NO 10), 2771475 (SEQUENCE ID NO 11), 1803247 (SEQUENCE ID NO 12), 1737526 (SEQUENCE ID NO 13), 2792957 (SEQUENCE ID NO 14), 1226186 (SEQUENCE ID NO 15), 774134IH (SEQUENCE ID NO 16), and 774419IH (SEQUENCE ID 17) were entered in the Sequencherm Program (available from Gene Codes Corporation, Ann Arbor, Mich., in order to generate a nucleotide alignment (contig map) and then generate their consensus sequence (SEQUENCE ID NO 18). FIGS. 1A–G show the nucleotide sequence alignment of these clones and their resultant nucleotide consensus sequence (SEQUENCE ID NO 18). FIG. 2 presents the contig map depicting the clones 2767646 (SEQUENCE ID NO 1), 774134 (SEQUENCE ID NO 2), 775437 (SEQUENCE ID NO 3), 1281329 (SEQUENCE ID NO 4), 1628677 (SEQUENCE ID NO 5), 1286372 (SEQUENCE ID NO 6), 774419 (SEQUENCE ID NO 7), 3233118 (SEQUENCE ID NO 8), 2733923 (SEQUENCE ID NO 9), 906605 (SEQUENCE ID NO 10), 2771475 (SEQUENCE ID NO 11), 1803247 (SEQUENCE ID NO 12), 1737526 (SEQUENCE ID NO 13), 2792957 (SEQUENCE ID NO 14), 1226186 (SEQUENCE ID NO 15), 774134IH (SEQUENCE ID NO 16), and 774419IH (SEQUENCE ID 17), which form overlapping regions of the CS193 gene, and the resultant consensus nucleotide sequence (SEQUENCE ID NO 18) of these clones in a graphic display. Following this, a three-frame translation was performed on the consensus sequence (SEQUENCE ID NO 18). The first forward frame was found to have an open reading frame encoding a 917 residue amino acid sequence which is presented as SEQUENCE ID NO 41. The 917 residue polypeptide sequence depicted in SEQUENCE ID NO 41 was compared with published sequences using software and techniques known to those skilled in the art. The polypeptide sequence of a bovine epithelial chloride channel protein was found to be partially homologous to the CS193 polypeptide of SEQUENCE ID NO 41. This bovine chloride channel protein is described by S. Cunningham et al. *J. Biol. Chem.* 270:31016–31026 (1995).

Example 2

Sequencing of CS193 EST-Specific Clones

The full-length DNA sequences of clones 774134 and 774419 of the CS193 gene contig were determined using dideoxy termination sequencing with dye terminators following known methods (F. Sanger et al., *PNAS U.S.A.* 74:5463 (1977). These full-length sequences are referred to herein as clones 774134IH (SEQUENCE ID NO 16) and 774419IH (SEQUENCE ID 17), respectively.

Because the pINCY vector (available from Incyte Pharmaceuticals, Inc., Palo Alto, Calif.) contains universal priming sites just adjacent to the 3' and 5' ligation junctions of the inserts, approximately 300 bases of the insert were sequenced in both directions using two universal primers (SEQUENCE ID NO 21 and SEQUENCE ID NO 22, available from New England Biolabs, Beverly, Mass., and Applied Biosystems Inc, Foster City, Calif.). The sequencing reactions were run on a polyacrylamide denaturing gel, and the sequences were determined by an Applied Biosystems 377 Sequencer (available from Applied Biosystems, Foster City, Calif.). Additional sequencing primers (SEQUENCE ID NOS 23–38) were designed from sequence information determined by the initial sequencing reactions near the 3'-ends of the two DNA strands. These primers then were used to determine the remaining DNA sequence of the cloned insert from each DNA strand, as previously described.

Example 3

Nucleic Acid

A. RNA Extraction From Tissue

Total RNA is isolated from GI tract tissues and from non-GI tract tissues. Various methods are utilized, including but not limited to the lithium chloride/urea technique, known in the art and described by Kato et al. (*J. Virol.* 61:2182–2191, 1987), and TRIzol™ (Gibco-BRL, Grand Island, N.Y.).

Briefly, tissue is placed in a sterile conical tube on ice and 10–15 volumes of 3 M LiCl, 6 M urea, 5 mM EDTA, 0.1 M β-mercaptoethanol, 50 MM Tris-HCl (pH 7.5) are added. The tissue is homogenized with a Polytron® homogenizer (Brinkman Instruments, Inc., Westbury, N.Y.) for 30–50 sec on ice. The solution is transferred to a 15 ml plastic centrifuge tube and placed overnight at −20° C. The tube is centrifuged for 90 min at 9,000×g at 0–4° C. and the supernatant is immediately decanted. Ten ml of 3 M LiCl are added and the tube is vortexed for 5 sec. The tube is centrifuged for 45 min at 11,000×g at 0–4° C. The decanting, resuspension in LiCl, and centrifugation is repeated and the final pellet is air dried and suspended in 2 ml of 1 mM EDTA, 0.5% SDS, 10 mM Tris (pH 7.5). Twenty microliters (20 µl) of Proteinase K (20 mg/ml) are added, and the solution is incubated for 30 min at 37° C. with occasional mixing. One-tenth volume (0.22–0.25 ml) of 3 M NaCl is added and the solution is vortexed before transfer into another tube containing 2 ml of phenol/chloroform/isoamyl alcohol (PCI). The tube is vortexed for 1–3 sec and centrifuged for 20 min at 3,000×g at 10° C. The PCI extraction is repeated and followed by two similar extractions with chloroform/isoamyl alcohol (CI). The final aqueous solution is transferred to a prechilled 15 ml Corex glass tube containing 6 ml of absolute ethanol, the tube is covered with parafilm, and placed at −20° C. overnight. The tube is centrifuged for 30 min at 10,000×g at 0–4° C. and the ethanol supernatant is decanted immediately. The RNA pellet is washed four times with 10 ml of 75% ice-cold ethanol and the final pellet is air dried for 15 min at room temperature. The RNA is suspended in 0.5 ml of 10 mM TE (pH 7.6, 1 mM EDTA) and its concentration is determined spectrophotometrically. RNA samples are aliquoted and stored at −70° C. as ethanol precipitates.

The quality of the RNA is determined by agarose gel electrophoresis (see Example 5, Northern Blot Analysis) and staining with 0.5 µg/ml ethidium bromide for one hour. RNA samples that do not contain intact rRNAs are excluded from the study.

Alternatively, for RT-PCR analysis, 1 ml of Ultraspec RNA reagent is added to 120 mg of pulverized tissue in a 2.0 ml polypropylene microfuge tube, homogenized with a Polytron® homogenizer (Brinkman Instruments, Inc., Westbury, N.Y.) for 50 sec and placed on ice for 5 min. Then, 0.2 ml of chloroform is added to each sample, followed by vortexing for 15 sec. The sample is placed on ice for another 5 min, followed by centrifugation at 12,000×g for 15 min at 4° C. The upper layer is collected and transferred to another RNase-free 2.0 ml microfuge tube. An equal volume of isopropanol is added to each sample, and the solution is placed on ice for 10 min. The sample is centrifuged at 12,000×g for 10 min at 4° C., and the supernatant is discarded. The remaining pellet is washed twice with cold 75% ethanol, resuspended by vortexing, and the resuspended material is then pelleted by centrifugation at 7500×g for 5 min at 4° C. Finally, the RNA pellet is dried in a Speedvac (Savant, Farmingdale, N.Y.) for 5 min and reconstituted in RNase-free water.

B. RNA Extraction From Blood Mononuclear Cells

Mononuclear cells are isolated from blood samples from patients by centrifugation using Ficoll-Hypaque as follows. A 10 ml volume of whole blood is mixed with an equal volume of RPMI Medium (Gibco-BRL, Grand Island, N.Y.). This mixture is then underlayed with 10 ml of Ficoll-Hypaque (Pharmacia, Piscataway, N.J.) and centrifuged for 30 minutes at 200×g. The buffy coat containing the mononuclear cells is removed, diluted to 50 ml with Dulbecco's PBS (Gibco-BRL, Grand Island, N.Y.) and the mixture centrifuged for 10 minutes at 200×g. After two washes, the resulting pellet is resuspended in Dulbecco's PBS to a final volume of 1 ml.

RNA is prepared from the isolated mononuclear cells as described by N. Kato et al., *J. Virology* 61: 2182–2191 (1987). Briefly, the pelleted mononuclear cells are brought to a final volume of 1 ml and then are resuspended in 250 µL of PBS and mixed with 2.5 ml of 3 M LiCl, 6 M urea, 5 mM EDTA, 0.1 M 2-mercaptoethanol, 50 mM Tris-HCl (pH 7.5). The resulting mixture is homogenized and incubated at −20° C. overnight. The homogenate is centrifuged at 8,000 RPM in a Beckman J2-21M rotor for 90 minutes at 0–4° C. The pellet is resuspended in 10 ml of 3 M LiCl by vortexing and then centrifuged at 10,000 RPM in a Beckman J2-21M rotor centrifuge for 45 minutes at 0–4° C. The resuspending and pelleting steps then are repeated. The pellet is resuspended in 2 ml of 1 mM EDTA, 0.5% SDS, 10 mM Tris (pH 7.5) and 400 µg Proteinase K with vortexing and then it is incubated at 37° C. for 30 minutes with shaking. One tenth volume of 3 M NaCl then is added and the mixture is vortexed. Proteins are removed by two cycles of extraction with phenol/chloroform/isoamyl alcohol (PCI) followed by one extraction with chloroform/isoamyl alcohol (CI). RNA is precipitated by the addition of 6 ml of absolute ethanol followed by overnight incubation at −20° C. After the precipitated RNA is collected by centrifugation, the pellet is washed 4 times in 75% ethanol. The pelleted RNA is then dissolved in solution containing 1 mM EDTA, 10 mM Tris-HCl (pH 7.5).

Non-GI tract tissues are used as negative controls. The mRNA can be further purified from total RNA by using commercially available kits such as oligo dT cellulose spin columns (RediCol™ from Pharmacia, Uppsala, Sweden) for the isolation of polyadenylated RNA. Total RNA or mRNA can be dissolved in lysis buffer (SM guanidine thiocyanate, 0.1 M EDTA, pH 7.0) for analysis in the ribonuclease protection assay.

C. RNA Extraction From Polysomes

Tissue is minced in saline at 4° C. and mixed with 2.5 volumes of 0.8 M sucrose in a $TK_{150}M$ solution (150 mM KCl, 5 mM $MgCl_2$, 50 mM Tris-HCl, pH 7.4) containing 6 mM 2-mercaptoethanol. The tissue is homogenized in a Teflon-glass Potter homogenizer with five strokes at 100–200 rpm followed by six strokes in a Dounce homogenizer, as described by B. Mechler, *Methods in Enzy-* mology 152:241–248 (1987). The homogenate then is centrifuged at 12,000×g for 15 min at 4° C. to sediment the nuclei. The polysomes are isolated by mixing 2 ml of the supernatant with 6 ml of 2.5 M sucrose in $TK_{150}M$ and layering this mixture over 4 ml of 2.5 M sucrose in $TK_{150}M$ in a 38 ml polyallomer tube. Two additional sucrose $TK_{150}M$ solutions are successively layered onto the extract fraction; a first layer of 13 ml 2.05 M sucrose, followed by a second layer of 6 ml of 1.3 M sucrose. The polysomes are isolated by centrifuging the gradient at 90,000×g for 5 hr at 4° C. The fraction then is taken from the 1.3 M sucrose/2.05 M sucrose interface with a siliconized pasteur pipette and diluted in an equal volume of TE (10 mM Tris-HCl, pH 7.4, 1 mM EDTA). An equal volume of 90° C. SDS buffer (1% SDS, 200 mM NaCl, 20 mM Tris-HCl, pH 7.4) is added and the solution is incubated in a boiling water bath for 2 min. Proteins next are digested with a Proteinase-K digestion (50 mg/ml) for 15 min at 37° C. The mRNA is purified with 3 equal volumes of phenol-chloroform extractions followed by precipitation with 0.1 volume of 2 M sodium acetate (pH 5.2) and 2 volumes of 100% ethanol at −20° C. overnight. The precipitated RNA is recovered by centrifugation at 12,000×g for 10 min at 4° C. The RNA is dried and resuspended in TE (pH 7.4) or distilled water. The resuspended RNA then can be used in a slot blot or dot blot hybridization assay to check for the presence of CS193 mRNA (see Example 6).

The quality of nucleic acid and proteins is dependent on the method of preparation used. Each sample may require a different preparation technique to maximize isolation efficiency of the target molecule. These preparation techniques are within the skill of the ordinary artisan.

Example 4

Ribonuclease Protection Assay

A. Synthesis of Labeled Complementary RNA (cRNA) Hybridization Probe and Unlabeled Sense Strand Labeled antisense and unlabeled sense riboprobes are transcribed from the CS193 gene cDNA sequence which contains a 5' RNA polymerase promoter such as SP6 or T7. The sequence may be from a vector containing the appropriate CS193 cDNA insert, or from a PCR-generated product of the insert using PCR primers which incorporate a 5' RNA polymerase promoter sequence. For example, the described plasmid, clones 774134 or 774419 or another comparable clone, containing the CS193 gene cDNA sequence, flanked by opposed SP6 and T7 polymerase promoters, is purified using Qiagen Plasmid Purification Kit (Qiagen, Chatsworth, Calif.). Then 10 μg of the plasmid are linearized by cutting with 10 U DdeI restriction enzyme for 1 hr at 37° C. The linearized plasmid is purified using QIAprep kits (Qiagen, Chatsworth, Calif.) and used for the synthesis of antisense transcript from the appropriate SP6 or T7 promoter using the Riboprobe® in vitro Transcription System (Promega Corporation, Madison, Wis.), as described by the supplier's instructions, incorporating either 6.3 μM (alpha$^{32}$P) UTP (Amersham Life Sciences, Inc. Arlington Heights, Ill.) or 100–500 μM biotinylated UTP as a label. To generate the sense strand, 10 μg of the purified plasmid are cut with restriction enzymes 10U XbaI and 10 U NotI, and transcribed as above from the appropriate SP6 or T7 promoter. Both sense and antisense strands are isolated by spin column chromatography. Unlabeled sense strand is quantitated by UV absorption at 260 nm.

B. Hybridization of Labeled Probe to Target

Frozen tissue is pulverized to powder under liquid nitrogen and 100–500 mg are dissolved in 1 ml of lysis buffer, available as a component of the Direct Protect™ Lysate RNase Protection kit (Ambion, Inc., Austin, Tex.). Further dissolution can be achieved using a tissue homogenizer. In addition, a dilution series of a known amount of sense strand in mouse liver lysate is made for use as a positive control. Finally, 45 μl of solubilized tissue or diluted sense strand is mixed directly with either 1) 1×10$^5$ cpm of radioactively labeled probe or 2) 250 pg of non-isotopically labeled probe in 5 μl of lysis buffer. Hybridization is allowed to proceed overnight at 37° C. See, T. Kaabache et al., *Anal. Biochem.* 232:225–230 (1995).

C. RNase Digestion

RNA that is not hybridized to probe is removed from the reaction as per the Direct Protectf protocol using a solution of RNase A and RNase T1 for 30 min at 37° C., followed by removal of RNase by Proteinase-K digestion in the presence of sodium sarcosyl. Hybridized fragments protected from digestion are then precipitated by the addition of an equal volume of isopropanol and placed at −70° C. for 3 hr. The precipitates are collected by centrifugation at 12,000×g for 20 min.

D. Fragment Analysis

The precipitates are dissolved in denaturing gel loading dye (80% formamide, 10 mM EDTA (pH 8.0), 1 mg/ml xylene cyanol, 1 mg/ml bromophenol blue), heat denatured, and electrophoresed in 6% polyacrylamide TBE, 8 M urea denaturing gels. The gels are imaged and analyzed using the STORM™ storage phosphor autoradiography system (Molecular Dynamics, Sunnyvale, Calif.). Quantitation of protected fragment bands, expressed in femtograms (fg), is achieved by comparing the peak areas obtained from the test samples to those from the known dilutions of the positive control sense strand (see Section B, supra). The results are expressed in molecules of CS193 RNA/cell and as a image rating score. In cases where non-isotopic labels are used, hybrids are transferred from the gels to membranes (nylon or nitrocellulose) by blotting and then analyzed using detection systems that employ streptavidin alkaline phosphatase conjugates and chemiluminesence or chemifluoresence reagents.

Detection of a product comprising a sequence selected from the group consisting of SEQUENCE ID NOS 1–18, and fragments or complements thereof, is indicative of the presence of CS193 mRNA(s), suggesting a diagnosis of a GI tract tissue disease or condition, such as GI tract cancer.

Example 5

Northern Blotting

The northern blot technique is used to identify a specific size RNA fragment from a complex population of RNA using gel electrophoresis and nucleic acid hybridization. Northern blotting is well-known technique in the art. Briefly, 5–10 μg of total RNA (see Example 3) are incubated in 15 μl of a solution containing 40 mM morphilinopropane-sulfonic acid (MOPS) (pH 7.0), 10 mM sodium acetate, 1 mM EDTA, 2.2 M formaldehyde, 50% v/v formamide for 15 min at 65° C. The denatured RNA is mixed with 2 μl of loading buffer (50% glycerol, 1 mM EDTA, 0.4% bromophenol blue, 0.4% xylene cyanol) and loaded into a denaturing 1.0% agarose gel containing 40 mM MOPS (pH 7.0), 10 mM sodium acetate, 1 mM EDTA and 2.2 M formaldehyde. The gel is electrophoresed at 60 V for 1.5 h and rinsed in RNAse free water. RNA is transferred from the gel onto nylon membranes (Brightstar-Plus, Ambion, Inc., Austin, Tex.) for 1.5 hours using the downward alkaline capillary transfer method (Chomczynski, *Anal. Biochem.* 201:134–139, 1992). The filter is rinsed with 1×SSC, and RNA is crosslinked to the filter using a Stratalinker (Stratagene, Inc., La Jolla, Calif.) on the autocrosslinking mode and dried for 15 min. The membrane is then placed into a hybridization tube containing 20 ml of preheated prehybridization solution (5×SSC, 50% formamide, 5×Denhardt's solution, 100 µg/ml denatured salmon sperm DNA) and incubated in a 42° C. hybridization oven for at least 3 hr. While the blot is prehybridizing, a $^{32}$P-labeled random-primed probe is generated using the CS193 insert fragment (obtained by digesting clones 774134 or 774419 or another comparable clone with XbaI and NotI) using Random Primer DNA Labeling System (Life Technologies, Inc., Gaithersburg, Md.) according to the manufacturer's instructions. Half of the probe is boiled for 10 min, quick chilled on ice and added to the hybridization tube. Hybridization is carried out at 42° C. for at least 12 hr. The hybridization solution is discarded and the filter is washed in 30 ml of 3×SSC, 0.1% SDS at 42° C. for 15 min, followed by 30 ml of 3×SSC, 0.1% SDS at 42° C. for 15 min. The filter is wrapped in saran wrap, exposed to Kodak XAR-Omat film for 8–96 hr, and the film is developed for analysis.

Detection of a product comprising a sequence selected from the group consisting of SEQUENCE ID NOS 1–18, and fragments or complements thereof, is indicative of the presence of CS193 mRNA(s), suggesting a diagnosis of a GI tract tissue disease or condition, such as GI tract cancer.

Example 6
Dot Blot/Slot Blot

Dot and slot blot assays are quick methods to evaluate the presence of a specific nucleic acid sequence in a complex mix of nucleic acid. To perform such assays, up to 50 µg of RNA are mixed in 50 µl of 50% formamide, 7% formaldehyde, 1×SSC, incubated 15 min at 68° C., and then cooled on ice. Then, 100 µl of 20×SSC are added to the RNA mixture and loaded under vacuum onto a manifold apparatus that has a prepared nitrocellulose or nylon membrane. The membrane is soaked in water, 20×SSC for 1 hour, placed on two sheets of 20×SSC prewet Whatman #3 filter paper, and loaded into a slot blot or dot blot vacuum manifold apparatus. The slot blot is analyzed with probes prepared and labeled as described in Example 4, supra. Detection of a product comprising a sequence selected from the group consisting of SEQUENCE ID NOS 1–18, and fragments or complements thereof, is indicative of the presence of CS193 mRNA(s), suggesting a diagnosis of a GI tract tissue disease or condition, such as GI tract cancer.

Other methods and buffers which can be utilized in the methods described in Examples 5 and 6, but not specifically detailed herein, are known in the art and are described in J. Sambrook et al, supra which is incorporated herein by reference.

Example 7
In Situ Hybridization

This method is useful to directly detect specific target nucleic acid sequences in cells using detectable nucleic acid hybridization probes.

Tissues are prepared with cross-linking fixative agents such as paraformaldehyde or glutaraldehyde for maximum cellular RNA retention. See, L. Angerer et al., *Methods in Cell Biol.* 35:37–71 (1991). Briefly, the tissue is placed in greater than 5 volumes of 1% glutaraldehyde in 50 mM sodium phosphate, pH 7.5 at 4° C. for 30 min. The solution is changed with fresh glutaraldehyde solution (1% glutaraldehyde in 50 mM sodium phosphate, pH 7.5) for a further 30 min fixing. The fixing solution should have an osmolality of approximately 0.375% NaCl. The tissue is washed once in isotonic NaCl to remove the phosphate.

The fixed tissues then are embedded in paraffin as follows. The tissue is dehydrated though a series of increasing ethanol concentrations for 15 min each: 50% (twice), 70% (twice), 85%, 90% and then 100% (twice). Next, the tissue is soaked in two changes of xylene for 20 min each at room temperature. The tissue is then soaked in two changes of a 1:1 mixture of xylene and paraffin for 20 min each at 60° C.; and then in three final changes of paraffin for 15 min each.

Next, the tissue is cut in 5 µm sections using a standard microtome and placed on a slide previously treated with a tissue adhesive such as 3-aminopropyltriethoxysilane.

Paraffin is removed from the tissue by two 10 min xylene soaks and rehydrated in a series of decreasing ethanol concentrations: 99% (twice), 95%, 85%, 70%, 50%, 30%, and then distilled water (twice). The sections are pre-treated with 0.2 M HCl for 10 min and permeabilized with 2 µg/ml Proteinase-K at 37° C. for 15 min.

Labeled Riboprobes transcribed from the CS193 gene plasmid (see Example 4) are hybridized to the prepared tissue sections and incubated overnight at 56° C. in 3×standard saline extract and 50% formamide. Excess probe is removed by washing in 2×standard saline citrate and 50% formamide followed by digestion with 100 µg/ml RNase A at 37° C. for 30 min. Fluorescence probe is visualized by illumination with ultraviolet (UV) light under a microscope. Fluorescence in the cytoplasm is indicative of CS193 mRNA. Alternatively, the sections can be visualized by autoradiography.

Detection of a product comprising a sequence selected from the group consisting of SEQUENCE ID NOS 1–18, and fragments or complements thereof, is indicative of the presence of CS193 mRNA(s), suggesting a diagnosis of a GI tract tissue disease or condition, such as GI tract cancer.

Example 8
Reverse Transcription PCR
A. One Step RT-PCR Assay

Target-specific primers are designed to detect the above-described target sequences by reverse transcription PCR using methods known in the art. One step RT-PCR is a sequential procedure that performs both RT and PCR in a single reaction mixture. The procedure is performed in a 200 µl reaction mixture containing 50 mM (N,N,-bis[2-Hydroxyethyl]glycine), pH 8.15, 81.7 mM KOAc, 33.33 mM KOH, 0.01 mg/ml bovine serum albumin, 0.1 mM ethylene diaminetetraacetic acid, 0.02 mg/ml NaN$_3$, 8% w/v glycerol, 150 µM each of dNTP, 0.25 µM each primer, 5U rTth polymerase, 3.25 mM Mn(OAc)$_2$ and 5 µl of target RNA (see Example 3). Since RNA and the rTth polymerase enzyme are unstable in the presence of Mn(OAc)$_2$, the Mn(OAc)$_2$ should be added just before target addition. Optimal conditions for cDNA synthesis and thermal cycling readily can be determined by those skilled in the art. The reaction is incubated in a Perkin-Elmer Thermal Cycler 480. Optimal conditions for cDNA synthesis and thermal cycling can readily be determined by those skilled in the art. Conditions which may be found useful include cDNA synthesis at 60°–70° C. for 15–45 min and 30–45 amplification cycles at 94° C., 1 min; 55°–70° C., 1 min; 72° C., 2 min. One step RT-PCR also may be performed by using a dual enzyme procedure with Taq polymerase and a reverse transcriptase enzyme, such as MMLV or AMV RT enzymes.
B. Traditional RT-PCR A traditional two-step RT-PCR reaction was performed, as described by K. Q. Hu et al., *Virology* 181:721–726 (1991). Briefly, 0.5 µg of extracted mRNA (see Example 3) was reverse transcribed in a 20 µl reaction mixture containing 1×PCR II buffer (Perkin-Elmer), 5 mM MgCl$_2$, 1 mM dNTP, 20 U RNasin, 2.5 µM random hexamers, and 50 U MMLV (Moloney murine leukemia virus) reverse transcriptase (RT). Reverse transcription was performed at room temperature for 10 min, 42° C. for 60 min in a PE-480 thermal cycler, followed by further incubation at 95° C. for 5 min to inactivate the RT. PCR was performed using 2 μl of the cDNA reaction in a final PCR reaction volume of 50 μl containing 10 mM Tris-HCl (pH 8.3), 50 mM KCl, 1.5 mM MgCl$_2$, 200 μM DNTP, 0.4 μM of each sense and antisense primer, SEQUENCE ID NO 39 and SEQUENCE ID NO 40, respectively, and 2.5 U of Taq polymerase. The reaction was incubated in an MJ Research Model PTC-200 as follows: Denaturation at 94° C. for 2 min., followed by 35 cycles of amplification (94° C., 45 sec; 55° C., 45 sec; and 72° C., 2 min); a final extens (72° C., 5 min); and a soak at 4° C.

C. PCR Fragment Analysis

The correct products then can be verified by size determination using gel electrophoresis with SYBR® Green I nucleic acid gel stain (Molecular Probes, Eugene, Oreg.) and imaged using a STORM imaging system, or also verified by Southern, dot or slot blot analysis using a labeled probe against the internal sequences of the PCR product. The probes also may be polynucleotides analogs, such as morpholinos or peptide nucleic acids analogs (PNAs).

Detection of a product comprising a sequence selected from the group consisting of SEQUENCE ID NOS 1–18, and fragments or complements thereof, is indicative of the presence of CS193 mRNA(s), suggesting a diagnosis of a GI tract tissue disease or condition, such as GI tract cancer.

Example 9

OH-PCR

A. Probe selection and Labeling

Target-specific primers and probes are designed to detect the above-described target sequences by oligonucleotide hybridization PCR. International Publication NOS WO 92/10505, published Jun. 25, 1992, and WO 92/11388, published Jul. 9, 1992, teach methods for labeling oligonucleotides at their 5' and 3' ends, respectively. According to one known method for labeling an oligonucleotide, a label-phosphoramidite reagent is prepared and used to add the label to the oligonucleotide during its synthesis. For example, see N. T. Thuong et al., Tet. Letters 29(46) :5905–5908 (1988); or J. S. Cohen et al., published U.S. patent application Ser. No. 07/246,688 (NTIS ORDER No. patent application Ser. No. 7/246,688) (1989). Preferably, probes are labeled at their 3' end to prevent participation in PCR and the formation of undesired extension products. For one step OH-PCR, the probe should have a T$_M$ at least 15° C. below the T$_M$ of the primers. The primers and probes are utilized as specific binding members, with or without detectable labels, using standard phosphoramidite chemistry and/ or post-synthetic labeling methods which are well-known to one skilled in the art.

B. One Step Oligo Hybridization PCR

OH-PCR is performed on a 200 μl reaction containing 50 mM (N,N,-bis[2-Hydroxyethyl]glycine), pH 8.15, 81.7 mM KOAc, 33.33 mM KOH, 0.01 mg/ml bovine serum albumin, 0.1 mM ethylene diaminetetraacetic acid, 0.02 mg/ml NaN$_3$, 8% w/v glycerol, 150 μM each of DNTP, 0.25 μM each primer, 3.75 nM probe, 5U rTth polymerase, 3.25 mM Mn(OAc)$_2$ and 5 μl blood equivalents of target (see Example 3). Since RNA and the rTth polymerase enzyme are unstable in the presence of Mn(OAc)$_2$, the Mn(OAc)$_2$ should be added just before target addition. The reaction is incubated in a Perkin-Elmer Thermal Cycler 480. Optimal conditions for cDNA synthesis and thermal cycling can be readily determined by those skilled in the art. Conditions which may be found useful include cDNA synthesis (60° C., 30 min), 30–45 amplification cycles (94° C., 40 sec; 55–70° C., 60 sec), oligo-hybridization (97° C., 5 min; 15° C., 5 min; 15° C. soak). The correct reaction product contains at least one of the strands of the PCR product and an internally hybridized probe.

C. OH-PCR Product Analysis

Amplified reaction products are detected on an LCx® analyzer system (available from Abbott Laboratories, Abbott Park, Ill.). Briefly, the correct reaction product is captured by an antibody labeled microparticle at a capturable site on either the PCR product strand or the hybridization probe, and the complex is detected by binding of a detectable antibody conjugate to either a detectable site on the probe or the PCR strand. Only a complex containing a PCR strand hybridized with the internal probe is detectable. The detection of this complex then is indicative of the presence of CS193 mRNA, suggesting a diagnosis of a GI tract disease or condition, such as GI tract cancer.

Many other detection formats exist which can be used and/or modified by those skilled in the art to detect the presence of amplified or non-amplified CS193-derived nucleic acid sequences including, but not limited to, ligase chain reaction (LCR, Abbott Laboratories, Abbott Park, Ill.); Q-beta replicase (Gene-Trak™, Naperville, Ill.), branched chain reaction (Chiron, Emeryville, Calif.) and strand displacement assays (Becton Dickinson, Research Triangle Park, N.C.).

Detection of a product comprising a sequence selected from the group consisting of SEQUENCE ID NOS 1–18, and fragments or complements thereof, is indicative of the presence of CS193 mRNA(s), suggesting a diagnosis of a GI tract tissue disease or condition, such as GI tract cancer.

Example 10

Synthetic Peptide Production

Synthetic peptides were modeled and then prepared based upon the predicted amino acid sequence of the CS193 polypeptide consensus sequence (see Example 1). In particular, a number of CS193 peptides modeled from SEQUENCE ID NO 41, including the peptides of SEQUENCE ID NOS 42–49. Of these, a number of peptides were prepared, including the peptides of SEQUENCE ID NO 42, SEQUENCE ID NO 43, SEQUENCE ID NO 44, and SEQUENCE ID NO 45. All peptides were synthesized on a Symphony Peptide Synthesizer (available from Rainin Instrument Co, Emeryville, Calif.) using FMOC chemistry, standard cycles and in-situ HBTU activation. Cleavage and deprotection conditions were as follows: a volume of 2.5 ml of cleavage reagent (77.5% v/v trifluoroacetic acid, 15% v/v ethanedithiol, 2.5% v/v water, 5% v/v thioanisole, 1–2% w/v phenol) were added to the resin, and agitated at room temperature for 2–4 hours. The filtrate was then removed, and the peptide was precipitated from the cleavage reagent with cold diethyl ether. Each peptide was filtered, purified via reverse-phase preparative HPLC using a water/ acetonitrile/0.1% TFA gradient, and lyophilized. The product was confirmed by mass spectrometry (see Example 12).

The purified peptides were used to immunize animals (see Example 14).

Example 11a

Expression of Protein in a Cell Line Using Plasmid 577

A. Construction of a CS193 Expression Plasmid

Plasmid 577, described in U.S. patent application Ser. No. 08/478,073, filed Jun. 7, 1995 and incorporated herein by reference, has been constructed for the expression of secreted antigens in a permanent cell line. This plasmid contains the following DNA segments: (a) a 2.3 Kb fragment of pBR322 containing bacterial beta-lactamase and origin of DNA replication; (b) a 1.8 Kb cassette directing expression of a neomycin resistance gene under control of HSV-1 thymidine kinase promoter and poly-A addition signals; (c) a 1.9 Kb cassette directing expression of a dihydrofolate reductase gene under the control of an SV-40 promoter and poly-A addition signals; (d) a 3.5 Kb cassette directing expression of a rabbit immunoglobulin heavy chain signal sequence fused to a modified hepatitis C virus (HCV) E2 protein under the control of the Simian Virus 40 T-Ag promoter and transcription enhancer, the hepatitis B virus surface antigen (HBsAg) enhancer I followed by a fragment of Herpes Simplex Virus-1 (HSV-1) genome providing poly-A addition signals; and (e) a residual 0.7 Kb fragment of Simian Virus 40 genome late region of no function in this plasmid. All of the segments of the vector were assembled by standard methods known to those skilled in the art of molecular biology.

Plasmids for the expression of secretable CS193 proteins are constructed by replacing the hepatitis C virus E2 protein coding sequence in plasmid 577 with that of a CS193 polynucleotide sequence selected from the group consisting of SEQUENCE ID NOS 1–18, and fragments or complements thereof, as follows. Digestion of plasmid 577 with XbaI releases the hepatitis C virus E2 gene fragment. The resulting plasmid backbone allows insertion of the CS193 cDNA insert downstream of the rabbit immunoglobulin heavy chain signal sequence which directs the expressed proteins into the secretory pathway of the cell. The CS193 cDNA fragment is generated by PCR using standard procedures. Encoded in the sense PCR primer sequence is an XbaI site, immediately followed by a 12 nucleotide sequence that encodes the amino acid sequence Ser-Asn-Glu-Leu ("SNEL") to promote signal protease processing, efficient secretion and final product stability in culture fluids. Immediately following this 12 nucleotide sequence the primer contains nucleotides complementary to template sequences encoding amino acids of the CS193 gene. The antisense primer incorporates a sequence encoding the following eight amino acids just before the stop codons: Asp-Tyr-Lys-Asp-Asp-Asp-Asp-Lys (SEQUENCE ID NO 50). Within this sequence is incorporated a recognition site to aid in analysis and purification of the CS193 protein product. A recognition site (termed "FLAG") that is recognized by a commercially available monoclonal antibody designated anti-FLAG M2 (Eastman Kodak, Co., New Haven, Conn.) can be utilized, as well as other comparable sequences and their corresponding antibodies. For example, PCR is performed using Gene-Amp® reagents obtained from Perkin-Elmer-Cetus, as directed by the supplier's instructions. PCR primers are used at a final concentration of 0.5 $\mu$M. PCR is performed on the CS193 plasmid template in a 100 $\mu$l reaction for 35 cycles (94° C., 30 seconds; 55° C., 30 seconds; 72° C., 90 seconds) followed by an extension cycle of 72° C. for 10 min.

B. Transfection of Dihydrofolate Reductase Deficient Chinese Hamster Ovary Cells The plasmid described supra is transfected into CHO/dhfr-cells (DXB-111, Uriacio et al., *PNAS* 77:4451–4466 (1980)). These cells are available from the A.T.C.C., 12301 Parklawn Drive, Rockville, Md. 20852, under Accession No. CRL 9096. Transfection is carried out using the cationic liposome-mediated procedure described by P. L. Felgner et al., *PNAS* 84:7413–7417 (1987). Particularly, CHO/dhfr-cells are cultured in Ham's F-12 media supplemented with 10% fetal calf serum, L-glutamine (1 mM) and freshly seeded into a flask at a density of 5–8×10$^5$ cells per flask. The cells are grown to a confluency of between 60 and 80% for transfection. Twenty micrograms (20 $\mu$g) of plasmid DNA is added to 1.5 ml of Opti-MEM I medium and 100 $\mu$l of Lipofectin Reagent (Gibco-BRL; Grand Island, N.Y.) are added to a second 1.5 ml portion of Opti-MEM I media. The two solutions are mixed and incubated at room temperature for 20 min. After the culture medium is removed from the cells, the cells are rinsed 3 times with 5 ml of Opti-MEM I medium. The Opti-MEM I-Lipofection-plasmid DNA solution then is overlaid onto the cells. The cells are incubated for 3 h at 37° C., after which time the Opti-MEM I-Lipofectin-DNA solution is replaced with culture medium for an additional 24 h prior to selection.

C. Selection and Amplification

One day after transfection, cells are passaged 1:3 and incubated with dhfr/G418 selection medium (hereafter, "F-12 minus medium G"). Selection medium is Ham's F-12 with L-glutamine and without hypoxanthine, thymidine and glycine (JRH Biosciences, Lenexa, Kans.) and 300 $\mu$g per ml G418 (Gibco-BRL; Grand Island, N.Y.). Media volume-to-surface area ratios of 5 ml per 25 cm$^2$ are maintained. After approximately two weeks, DHFR/G418 cells are expanded to allow passage and continuous maintenance in F-12 minus medium G.

Amplification of each of the transfected CS193 cDNA sequences is achieved by stepwise selection of DHFR$^+$, G418$^+$ cells with methotrexate (reviewed by R. Schimke, *Cell* 37:705–713 [1984]). Cells are incubated with F-12 minus medium G containing 150 nM methotrexate (MTX) (Sigma, St. Louis, Mo.) for approximately two weeks until resistant colonies appear. Further gene amplification is achieved by selection of 150 nM adapted cells with 5 $\mu$M MTX.

D. Antigen Production

F-12 minus medium G supplemented with 5 $\mu$M MTX is overlaid onto just confluent monolayers for 12 to 24 h at 37° C. in 5% $CO_2$. The growth medium is removed and the cells are rinsed 3 times with Dulbecco's phosphate buffered saline (PBS) with calcium and magnesium (Gibco-BRL; Grand Island, N.Y.) to remove the remaining media/serum which may be present. Cells then are incubated with VAS custom medium (VAS custom formulation with L-glutamine with HEPES without phenol red, available from JRH Bioscience; Lenexa, Kans., product number 52-08678P), for 1 h at 37° C. in 5% $CO_2$. Cells then are overlaid with VAS for production at 5 ml per T flask. Medium is removed after seven days of incubation, retained, and then frozen to await purification with harvests 2, 3 and 4. The monolayers are overlaid with VAS for 3 more seven day harvests.

E. Analysis of GI Tract Tissue Gene CS193 Antigen Expression

Aliquots of VAS supernatants from the cells expressing the CS193 protein construct are analyzed, either by SDS-polyacrylamide gel electrophoresis (SDS-PAGE) using standard methods and reagents known in the art (Laemmli discontinuous gels), or by mass spectrometry.

F. Purification

Purification of the CS193 protein containing the FLAG sequence is performed by immunoaffinity chromatography using an affinity matrix comprising anti-FLAG M2 monoclonal antibody covalently attached to agarose by hydrazide linkage (Eastman Kodak Co., New Haven, Conn.). Prior to affinity purification, protein in pooled VAS medium harvests from roller bottles is exchanged into 50 mM Tris-HCl (pH 7.5), 150 mM NaCl buffer using a Sephadex G-25 (Pharmacia Biotech Inc., Uppsala, Sweden) column. Protein in this buffer is applied to the anti-FLAG M2 antibody affinity column. Non-binding protein is eluted by washing the column with 50 mM Tris-HCl (pH 7.5), 150 mM NaCl buffer. Bound protein is eluted using an excess of FLAG peptide in 50 mM Tris-HCl (pH 7.5), 150 mM NaCl. The excess FLAG peptide can be removed from the purified CS193 protein by gel electrophoresis or HPLC.

Although plasmid 577 is utilized in this example, it is known to those skilled in the art that other comparable expression systems, such as CMV, can be utilized herein with appropriate modifications in reagent and/or techniques and are within the skill of the ordinary artisan.

The largest cloned insert containing the coding region of the CS193 gene is then sub-cloned into either (i) a eukaryotic expression vector which may contain, for example, a cytomegalovirus (CMV) promoter and/or protein fusible sequences which aid in protein expression and detection, or (ii) a bacterial expression vector containing a superoxide-dismutase (SOD) and CMP-KDO synthetase (CKS) or other protein fusion gene for expression of the protein sequence. Methods and vectors which are useful for the production of polypeptides which contain fusion sequences of SOD are described in EPO 0196056, published Oct. 1, 1986, which is incorporated herein by reference and those containing fusion sequences of CKS are described in EPO Publication No. 0331961, published Sep. 13, 1989, which publication is also incorporated herein by reference. This so-purified protein can be used in a variety of techniques, including, but not limited to animal immunization studies, solid phase immunoassays, etc.

Example 11b
Expression of Protein in a Cell Line Using pcDNA3.1/Myc-His
A. Construction of a CS193 Expression Plasmid Plasmid pcDNA3.1/Myc-His (Cat. #V855–20, Invitrogen, Carlsbad, Calif.) has been constructed, in the past, for the expression of secreted antigens by most mammalian cell lines. Expressed protein inserts are fused to a myc-his peptide tag. The myc-his tag is a 21 residue amino acid sequence having the following sequence: Glu-Gln-Lys-Leu-Ile-Ser-Glu-Glu-Asp-Leu-Asn-Met-His-Thr-Glu-His-His-His-His-His-His (SEQUENCE ID NO 51) and comprises a myc epitope and a polyhistidine sequence which are useful for the purification of an expressed fusion protein using either anti-myc or anti-his affinity columns, or metalloprotein binding columns.

Plasmids for the expression of secretable CS193 proteins are constructed by inserting an CS193 polynucleotide sequence selected from the group consisting of SEQUENCE ID NOS 1–18, and fragments or complements thereof. Prior to construction of an CS193 expression plasmid, the CS193 cDNA sequence is first cloned into a pCR®-Blunt vector as follows.

The CS193 cDNA fragment is generated by PCR using standard procedures. For example, PCR is performed using Stratagene® reagents obtained from Stratagene, La Jolla, Calif., as directed by the supplier's instructions. PCR primers are used at a final concentration of 0.5 µM. PCR using 5 U of pfu polymerase (Stratagene) is performed on the CS193 plasmid template (see Example 2) in a 50 µl reaction for 30 cycles (94° C., 1 min; 65° C., 1.5 min; 72° C., 3 min) followed by an extension cycle at 72° C. for 8 min. The sense PCR primer sequence comprises nucleotides which are either complementary to the pINCY vector directly upstream of the CS193 gene insert or which incorporate a 5' EcoRI restriction site, an adjacent downstream protein translation consensus initiator, and a 3' nucleic acid sequence which is the same sense as the 5'-most end of the CS193 cDNA insert. The antisense primer incorporates a 5' NotI restriction sequence and a sequence complementary to the 3' end of the CS193 cDNA insert just upstream of the 3'-most, in-frame stop codon. Five microliters (5 µl) of the resulting blunt-ended PCR product are ligated into 25 ng of linearized pCR®-Blunt vector (Invitrogen, Carlsbad, Calif.) interrupting the lethal ccdB gene of the vector. The resulting ligated vector is transfected into TOP10 E. coli (Invitrogen, Carlsbad, Calif.) using a One Shot™ transformation kit (Invitrogen, Carlsbad, Calif.) following the supplier's directions. The transfected cells are grown on LB-Kan (50 µg/ml kanamycin) selection plates at 37° C. Only cells containing a plasmid with an interrupted ccdB gene will grow after transfection (Grant, S.G.N., *PNAS USA* 87:4645–4649 (1990)). Transfected colonies are picked and grown up in 3 ml of LB-Kan broth at 37° C. Plasmid DNA is isolated using a QIAprep® (Qiagen Inc., Santa Clarita, Calif.) procedure, as directed by the supplier's instructions. The DNA is cut with EcoRI or SnaBI, and NotI restriction enzymes to release the CS193 insert fragment. The fragment is run on 1% Seakem® LE agarose/0.5 µg/ml ethidium bromide/TE gel, visualized by UV irradiation, excised and purified using QIAquick™ (Qiagen Inc., Santa Clarita, Calif.) procedures, as directed by the supplier's instructions.

The pcDNA3.1/Myc-His plasmid DNA is linearized by digestion with EcoRI or SnaBI, and NotI in the polylinker region of the plasmid DNA. The resulting plasmid DNA backbone allows insertion of the CS193 purified cDNA fragment, supra, downstream of a CMV promoter which directs expression of the proteins in mammalian cells. The ligated plasmid is transfected into DH5 alpha™ cells (GibcoBRL, Gaithersburg, Md.) as directed by the supplier's instructions. Briefly, 10 ng of pcDNA3.1/Myc-His containing an CS193 insert is added to 50 µl of competent DH5 alpha cells, and the contents are mixed gently. The mixture is incubated on ice for 30 min, heat shocked for 20 sec at 37° C., and placed on ice for an additional 2 min. Upon addition of 0.95 ml of LB medium, the mixture is incubated for 1 h at 37° C. while shaking at 225 rpm. The transfected cells are then plated onto 100 mm LB/Amp (50 µg/ml ampicillin) plates and grown at 37° C. Colonies are picked and grown in 3 ml of LB/Amp broth. Plasmid DNA is purified using a QIAprep® kit. Presence of the insert is confirmed using techniques known to those skilled in the art including, but not limited to, restriction digestion and gel analysis. See, e.g., J. Sambrook et al., supra.

B. Transfection of Human Embryonic Kidney 293 Cells

The CS193 expression plasmid described supra is purified from the DH5 alpha cells using a QIAfilter™ Maxi kit (Qiagen, Chatsworth, Calif.), and then transfected into HEK293 cells (F. L. Graham et al., *J. Gen. Vir.* 36:59–72 (1977)). These cells are available from the A.T.C.C., 12301 Parklawn Drive, Rockville, Md. 20852, under Accession No. CRL 1573. Transfection is carried out using the cationic lipofectamine-mediated procedure described by P. Hawley-Nelson et al., *Focus* 15:73 (1993). Particularly, HEK293 cells are cultured in 10 ml DMEM media supplemented with 10% fetal bovine serum (FBS), L-glutamine (2 mM) and freshly seeded into 100 mm culture plates at a density of $9 \times 10^6$ cells per plate. The cells are grown at 37° C. to a confluency of between 70% and 80% for transfection. Eight micrograms (8 µg) of plasmid DNA is added to 800 µl of Opti-MEM I® medium (Gibco-BRL, Grand Island, N.Y.), and 48–96 µl of Lipofectamine™ Reagent (Gibco-BRL, Grand Island, N.Y.) is added to a second 800 µl portion of Opti-MEM I® media. The two solutions are mixed and incubated at room temperature for 15–30 min. After the culture medium is removed from the cells, the cells are washed once with 10 ml of serum-free DMEM. The Opti- MEM I®-Lipofectamine-plasmid DNA solution is diluted in 6.4 ml of serum-free DMEM and then overlaid onto the cells. The cells are incubated for 5 h at 37° C., after which time, an additional 8 ml of DMEM with 20% FBS is added. After 18–24 h, the old medium is aspirated, and the cells are overlaid with 5 ml of fresh DMEM with 10% FBS. Supernatants and cell extracts are analyzed for CS193 gene activity 72 h after transfection.

C. Analysis of GI Tract Tissue Gene CS193 Antigen Expression

The culture supernatant, supra, is transferred to cryotubes and stored on ice. HEK293 cells are harvested by washing twice with 10 ml cold Dulbecco's PBS and lysing by addition of 1.5 ml of CAT lysis buffer (Boehringer Mannheim, Indianapolis, Ind.), followed by incubation for 30 min at room temperature. Lysate is transferred to 1.7 ml polypropylene microfuge tubes and centrifuged at 1000×g for 10 min. The supernatant is transferred to new cryotubes and stored on ice. Aliquots of cell supernatants and the lysate of the cells expressing the CS193 protein construct are analyzed for the presence of CS193 recombinant protein. The aliquots can be analyzed using SDS-polyacrylamide gel electrophoresis (SDS-PAGE), using standard methods and reagents known in the art. See, e.g., J. Sambrook et al., supra. The gels can then be blotted onto a solid medium such as nitrocellulose, nytran, or the like, and the CS193 protein band can be visualized using western blotting techniques with anti-myc epitope or anti-histidine monoclonal antibodies (Invitrogen, Carlsbad, Calif.) or CS193 polyclonal serum (see Example 14). Alternatively, the expressed CS193 recombinant protein can be analyzed by mass spectrometry (see Example 12).

D. Purification

Purification of the CS193 recombinant protein containing the myc-his sequence is performed using the Xpress® affinity chromatography system (Invitrogen, Carlsbad, Calif.) containing a nickel-charged agarose resin which specifically binds polyhistidine residues. Supernatants from 10×100 mm plates, prepared as described supra, are pooled and passed over the nickel-charged column. Non-binding protein is eluted by washing the column with 50 mM Tris-HCl (pH 7.5)/150 mM NaCl buffer, leaving only the myc-his fusion proteins. Bound CS193 recombinant protein then is eluted from the column using either an excess of imidazole or histidine, or a low pH buffer. Alternatively, the recombinant protein can also be purified by binding at the myc-his sequence to an affinity column consisting of either anti-myc or anti-histidine monoclonal antibodies conjugated through a hydrazide or other linkage to an agarose resin and eluting with an excess of myc peptide or histidine, respectively.

The purified recombinant protein can then be covalently cross-linked to a solid phase, such as N-hydroxysuccinimide-activated sepharose columns (Pharmacia Biotech, Piscataway, N.J.), as directed by supplier's instructions. These columns containing covalently linked CS193 recombinant protein, can then be used to purify anti-CS193 antibodies from rabbit or mouse sera (see Examples 13 and 14).

E. Coating Microtiter Plates with CS193 Expressed Proteins

Supernatant from a 100 mm plate, as described supra, is diluted in an appropriate volume of PBS. 100 µl of the resulting mixture is placed into each well of a Reacti-Bind™ metal chelate microtiter plate (Pierce, Rockford, Ill.), incubated at room temperature while shaking, and followed by three washes with 200 µl each of PBS with 0.05% Tween® 20. The prepared microtiter plate can then be used to screen polyclonal antisera for the presence of CS193 antibodies (see Example 17).

Although pcDNA3.1/Myc-His is utilized in this example, it is known to those skilled in the art that other comparable expression systems can be utilized herein with appropriate modifications in reagent and/or techniques and are within the skill of one of ordinary skill in the art. The largest cloned insert containing the coding region of the CS193 gene is sub-cloned into either (i) a eukaryotic expression vector which may contain, for example, a cytomegalovirus (CMV) promoter and/or protein fusible sequences which aid in protein expression and detection, or (ii) a bacterial expression vector containing a superoxide-dismutase (SOD) and CMP-KDO synthetase (CKS) or other protein fusion gene for expression of the protein sequence. Methods and vectors which are useful for the production of polypeptides which contain fusion sequences of SOD are described in European patent application No. EP 0 196 056, published Oct. 1, 1986, which is incorporated herein by reference, and vectors containing fusion sequences of CKS are described in European patent application No. EP 0 331 961, published Sep. 13, 1989, which publication is also incorporated herein by reference. The purified protein can be used in a variety of techniques, including but not limited to, animal immunization studies, solid phase immunoassays, etc.

Example 12

Chemical Analysis of GI Tract Tissue Proteins

A. Analysis of Tryptic Peptide Fragments Using MS

Sera from patients with GI tract disease, such as GI tract cancer, sera from patients with no GI tract disease, extracts of GI tract tissues or cells from patients with GI tract disease, such as GI tract cancer, extracts of GI tract tissues or cells from patients with no GI tract disease, and extracts of tissues or cells from other non-diseased or diseased organs of patients, are run on a polyacrylamide gel using standard procedures and stained with Coomassie Blue. Sections of the gel suspected of containing the unknown polypeptide are excised and subjected to an in-gel reduction, acetamidation and tryptic digestion. P. Jeno et al, *Anal. Bio.* 224:451–455 (1995) and J. Rosenfeld et al, *Anal. Bio.* 203:173–179 (1992). The gel sections are washed with 100 mM $NH_4HCO_3$ and acetonitrile. The shrunken gel pieces are swollen in digestion buffer (50 mM $NH_4HCO_3$, 5 mM $CaCl_2$ and 12.5 µg/ml trypsin) at 4° C. for 45 min. The supernatant is aspirated and replaced with 5 to 10 µl of digestion buffer without trypsin and allowed to incubate overnight at 37° C. Peptides are extracted with 3 changes of 5% formic acid and acetonitrile and evaporated to dryness. The peptides are adsorbed to approximately 0.1 µl of POROS R2 sorbent (Perseptive Biosystems, Framingham, Mass.) trapped in the tip of a drawn gas chromatography capillary tube by dissolving them in 10 µl of 5% formic acid and passing it through the capillary. The adsorbed peptides are washed with water and eluted with 5% formic acid in 60% methanol. The eluant is passed directly into the spraying capillary of an API III mass spectrometer (Perkin-Elmer Sciex, Thornhill, Ontario, Canada) for analysis by nano-electrospray mass spectrometry. M. Wilm et al., *Int. J. Mass Spectrom. Ion Process* 136:167–180 (1994) and M. Wilm et al., *Anal. Chem.* 66:1–8 (1994). The masses of the tryptic peptides are determined from the mass spectrum obtained off the first quadrupole. Masses corresponding to predicted peptides can be further analyzed in MS/MS mode to give the amino acid sequence of the peptide.

B. Peptide Fragment Analysis Using LC/MS

The presence of polypeptides predicted from mRNA sequences found in hyperplastic disease tissues also can be confirmed using liquid chromatography/tandem mass spectrometry (LC/MS/MS). D. Hess et al., *METHODS, A Companion to Methods in Enzymology* 6:227–238 (1994). The serum specimen or tumor extract from the patient is denatured with SDS and reduced with dithiothreitol (1.5 mg/ml) for 30 min at 90° C. followed by alkylation with iodoacetamide (4 mg/ml) for 15 min at 25° C. Following acrylamide electrophoresis, the polypeptides are electroblotted to a cationic membrane and stained with Coomassie Blue. Following staining, the membranes are washed and sections thought to contain the unknown polypeptides are cut out and dissected into small pieces. The membranes are placed in 500 μl microcentrifuge tubes and immersed in 10 to 20 μl of proteolytic digestion buffer (100 mM Tris-HCl, pH 8.2, containing 0.1 M NaCl, 10% acetonitrile, 2 mM $CaCl_2$ and 5 μg/ml trypsin) (Sigma, St. Louis, Mo.). After 15 h at 37° C., 3 μl of saturated urea and 1 μl of 100 μg/ml trypsin are added and incubated for an additional 5 h at 37° C. The digestion mixture is acidified with 3 μl of 10% trifluoroacetic acid and centrifuged to separate supernatant from membrane. The supernatant is injected directly onto a microbore, reverse phase HPLC column and eluted with a linear gradient of acetonitrile in 0.05% trifluoroacetic acid. The eluate is fed directly into an electrospray mass spectrometer, after passing though a stream splitter if necessary to adjust the volume of material. The data is analyzed following the procedures set forth in Example 12, Section A.

Example 13
Gene Immunization Protocol
A. In Vivo Antigen Expression

Gene immunization circumvents protein purification steps by directly expressing an antigen in vivo after inoculation of the appropriate expression vector. Also, production of antigen by this method may allow correct protein folding and glycosylation since the protein is produced in mammalian tissue. The method utilizes insertion of the gene sequence into a plasmid which contains a CMV promoter, expansion and purification of the plasmid and injection of the plasmid DNA into the muscle tissue of an animal. Preferred animals include mice and rabbits. See, for example, H. Davis et al., *Human Molecular Genetics* 2:1847–1851 (1993). After one or two booster immunizations, the animal can then be bled, ascites fluid collected, or the animal's spleen can be harvested for production of hybridomas.

B. Plasmid Preparation and Purification

CS193 cDNA sequences are generated from the CS193 cDNA-containing vector using appropriate PCR primers containing suitable 5' restriction sites following the procedures described in Example 11. The PCR product is cut with appropriate restriction enzymes and inserted into a vector which contains the CMV promoter (for example, pRc/CMV or pcDNA3 vectors from Invitrogen, San Diego, Calif.). This plasmid then is expanded in the appropriate bacterial strain and purified from the cell lysate using a CsCl gradient or a Qiagen plasmid DNA purification column. All these techniques are familiar to one of ordinary skill in the art of molecular biology.

C. Immunization Protocol

Anesthetized animals are immunized intramuscularly with 0. 1–100 μg of the purified plasmid diluted in PBS or other DNA uptake enhancers (Cardiotoxin, 25% sucrose). See, for example, H. Davis et al, *Human Gene Therapy* 4:733–740 (1993); and P. W. Wolff et al, *Biotechniques* 11:474–485 (1991). One to two booster injections are given at monthly intervals.

D. Testing and Use of Antiserum

Animals are bled and the resultant sera tested for antibody using peptides synthesized from the known gene sequence (see Example 16) using techniques known in the art, such as western blotting or EIA techniques. Antisera produced by this method can then be used to detect the presence of the antigen in a patient's tissue or cell extract or in a patient's serum by ELISA or Western blotting techniques, such as those described in Examples 15 through 18.

Example 14
Production of Antibodies Against CS193
A. Production of Polyclonal Antisera Antiserum against CS193 was prepared by injecting rabbits with peptides whose sequences were derived from that of the predicted amino acid sequence of the CS193 consensus sequence (SEQUENCE ID NO 18). The synthesis of peptides is described in Example 10. Unconjugated peptides, SEQUENCE ID NO 42, SEQUENCE ID NO 43, SEQUENCE ID NO 44, and SEQUENCE ID NO 45, were used as immunogens [i.e., peptides were not conjugated to a carrier such as keyhole limpet hemocyanine (KLH )].

Animal Immunization. Female white New Zealand rabbits weighing 2 kg or more were used for raising polyclonal antiserum. One animal was immunized per unconjugated peptide (SEQUENCE ID NO 42, SEQUENCE ID NO 43, SEQUENCE ID NO 44, and SEQUENCE ID NO 45). One week prior to the first immunization, 5 to 10 ml of blood were obtained from the animal to serve as a non-immune prebleed sample.

Unconjugated peptides, SEQUENCE ID NO 42, SEQUENCE ID NO 43, SEQUENCE ID NO 44, and SEQUENCE ID NO 45, were used to prepare the primary immunogen by emulsifying 0.5 ml of the peptide at a concentration of 2 mg/ml in PBS (pH 7.2) which contained 0.5 ml of complete Freund's adjuvant (CFA) (Difco, Detroit, Mich.). The immunogen was injected into several sites of the animal via subcutaneous, intraperitoneal, and intramuscular routes of administration. Four weeks following the primary immunization, a booster immunization was administered. The immunogen used for the booster immunization dose was prepared by emulsifying 0.5 ml of the same unconjugated peptide used for the primary immunogen, except that the peptide now was diluted to 1 mg/ml with 0.5 ml of incomplete Freund's adjuvant (IFA) (Difco, Detroit, Mich.). Again, the booster dose was administered into several sites via subcutaneous, intraperitoneal and intramuscular types of injections. The animals were bled (5 ml) two weeks after the booster immunizations and each serum was tested for immunoreactivity to the peptide as described below. The booster and bleed schedule was repeated at 4 week intervals until an adequate titer was obtained. The titer or concentration of antiserum was determined by using unconjugated peptides in a microtiter EIA as described in Example 17, below. An antibody titer of 1:500 or greater was considered an adequate titer for further use and study.

TABLE 1

Titer of rabbit anti-CS193 peptide antisera (13 week bleed)

| Peptide Immunogen | Titer |
| --- | --- |
| SEQUENCE ID NO 42 | 12,000 |
| SEQUENCE ID NO 43 | 12,000 |
| SEQUENCE ID NO 44 | 2,100 |
| SEQUENCE ID NO 45 | 42,000 |

B. Production of Monoclonal Antibody
1. Inmunization Protocol

Mice are immunized using peptides which can either be conjugated to a carrier such KLH, prepared as described hereinbelow, or unconjugated (i.e., not conjugated to a carrier such as KLH), except that the amount of the unconjugated or conjugated peptide for monoclonal antibody production in mice is one-tenth the amount used to produce polyclonal antisera in rabbits. Thus, the primary immunogen consists of 100 µg of unconjugated or conjugated peptide in 0.1 ml of CFA emulsion; while the immunogen used for booster immunizations consists of 50 µg of unconjugated or conjugated peptide in 0.1 ml of IFA. Hybridomas for the generation of monoclonal antibodies are prepared and screened using standard techniques. The methods used for monoclonal antibody development follow procedures known in the art such as those detailed in Kohler and Milstein, *Nature* 256:494 (1975) and reviewed in J. G. R. Hurrel, ed., *Monoclonal Hybridoma Antibodies: Techniques and Applications*, CRC Press, Inc., Boca Raton, Fla. (1982). Another method of monoclonal antibody development which is based on the Kohler and Milstein method is that of L. T. Mimms et al., *Virology* 176:604–619 (1990), which is incorporated herein by reference.

The immunization regimen (per mouse) consists of a primary immunization with additional booster immunizations. The primary immunogen used for the primary immunization consists of 100 µg of unconjugated or conjugated peptide in 50 µl of PBS (pH 7.2) previously emulsified in 50 µl of CFA. Booster immunizations performed at approximately two weeks and four weeks post primary immunization consist of 50 µg of unconjugated or conjugated peptide in 50 µl of PBS (pH 7.2) emulsified with 50 µl IFA. A total of 100 µl of this immunogen is inoculated intraperitoneally and subcutaneously into each mouse. Individual mice are screened for immune response by microtiter plate enzyme immunoassay (EIA) as described in Example 17 approximately four weeks after the third immunization. Mice are inoculated either intravenously, intrasplenically or intraperitoneally with 50 µg of unconjugated or conjugated peptide in PBS (pH 7.2) approximately fifteen weeks after the third immunization.

Three days after this intravenous boost, splenocytes are fused with, for example, Sp2/0-Ag14 myeloma cells (Milstein Laboratories, England) using the polyethylene glycol (PEG) method. The fusions are cultured in Iscove's Modified Dulbecco's Medium (IMDM) containing 10% fetal calf serum (FCS), plus 1% hypoxanthine, aminopterin and thymidine (HAT). Bulk cultures were screened by microtiter plate EIA following the protocol in Example 17. Clones reactive with the peptide used un immunogen and non-reactive with other peptides (i.e., peptides of CS193 not used as the immunogen) are selected for final expansion. Clones thus selected are expanded, aliquoted and frozen in IMDM containing 10% FCS and 10% dimethyl-sulfoxide.

2. Peptide Conjugation

Peptide is conjugated to maleimide activated keyhole limpet hemocyanine (KLH, commercially available as Imject®, available from Pierce Chemical Company, Rockford, Ill.). Imject® contains about 250 moles of reactive maleimide groups per mole of hemocyanine. The activated KLH is dissolved in phosphate buffered saline (PBS, pH 8.4) at a concentration of about 7.7 mg/ml. The peptide is conjugated through cysteines occurring in the peptide sequence, or to a cysteine previously added to the synthesized peptide in order to provide a point of attachment. The peptide is dissolved in dimethyl sulfoxide (DMSO, Sigma Chemical Company, St. Louis, Mo.) and reacted with the activated KLH at a mole ratio of about 1.5 moles of peptide per mole of reactive maleimide attached to the KLH. A procedure for the conjugation of peptide (SEQUENCE ID NO 42) is provided hereinbelow. It is known to the ordinary artisan that the amounts, times and conditions of such a procedure can be varied to optimize peptide conjugation.

The conjugation reaction described hereinbelow is based on obtaining 3 mg of KLH peptide conjugate ("conjugated peptide"), which contains about 0.77 µmoles of reactive maleimide groups. This quantity of peptide conjugate usually is adequate for one primary injection and four booster injections for production of polyclonal antisera in a rabbit. Briefly, peptide (SEQUENCE ID NO 42) is dissolved in DMSO at a concentration of 1.16 µmoles/100 µl of DMSO. One hundred microliters (100 µl) of the DMSO solution is added to 380 µl of the activated KLH solution prepared as described hereinabove, and 20 µl of PBS (pH 8.4) is added to bring the volume to 500 µl. The reaction is incubated overnight at room temperature with stirring. The extent of reaction is determined by measuring the amount of unreacted thiol in the reaction mixture. The difference between the starting concentration of thiol and the final concentration is assumed to be the concentration of peptide which has coupled to the activated KLH. The amount of remaining thiol is measured using Ellman's reagent (5,5'-dithiobis(2-nitrobenzoic acid), Pierce Chemical Company, Rockford, Ill.). Cysteine standards are made at a concentration of 0, 0.1, 0.5, 2, 5 and 20 mM by dissolving 35 mg of cysteine HCl (Pierce Chemical Company, Rockford, Ill.) in 10 ml of PBS (pH 7.2) and diluting the stock solution to the desired concentration(s). The photometric determination of the concentration of thiol is accomplished by placing 200 µl of PBS (pH 8.4) in each well of an Immulon 2® microwell plate (Dynex Technologies, Chantilly, Va.). Next, 10 µl of standard or reaction mixture is added to each well. Finally, 20 µl of Ellman's reagent at a concentration of 1 mg/ml in PBS (pH 8.4) is added to each well. The wells are incubated for 10 minutes at room temperature, and the absorbance of all wells is read at 415 nm with a microplate reader (such as the BioRad Model 3550, BioRad, Richmond, Calif.). The absorbance of the standards is used to construct a standard curve and the thiol concentration of the reaction mixture is determined from the standard curve. A decrease in the concentration of free thiol is indicative of a successful conjugation reaction. Unreacted peptide is removed by dialysis against PBS (pH 7.2) at room temperature for 6 hours. The conjugate is stored at 2–8° C. if it is to be used immediately; otherwise, it is stored at −20° C. or colder.

3. Production of Ascites Fluid Containing Monoclonal Antibodies

Frozen hybridoma cells prepared as described hereinabove are thawed and placed into expansion culture. Viable hybridoma cells are inoculated intraperitoneally into Pristane treated mice. Ascitic fluid is removed from the mice, pooled, filtered through a 0.2µ filter and subjected to an immunoglobulin class G (IgG) analysis to determine the volume of the Protein A column required for the purification.

4. Purification of Monoclonal Antibodies From Ascites Fluid

Briefly, filtered and thawed ascites fluid is mixed with an equal volume of Protein A sepharose binding buffer (1.5 M glycine, 3.0 M NaCl, pH 8.9) and refiltered through a 0.2µ filter. The volume of the Protein A column is determined by the quantity of IgG present in the ascites fluid. The eluate then is dialyzed against PBS (pH 7.2) overnight at 2–8° C. The dialyzed monoclonal antibody is sterile filtered and dispensed in aliquots. The immunoreactivity of the purified monoclonal antibody is confirmed by determining its ability to specifically bind to the peptide used as the immunogen by use of the EIA microtiter plate assay procedure of Example 17. The specificity of the purified monoclonal antibody is confirmed by determining its lack of binding to irrelevant peptides such as peptides of CS193 not used as the immunogen. The purified anti-CS193 monoclonal thus prepared and characterized is placed at either 2–8° C. for short term storage or at −80° C. for long term storage.

5. Further Characterization of Monoclonal Antibody

The isotype and subtype of the monoclonal antibody produced as described hereinabove can be determined using commercially available kits (available from Amersham. Inc., Arlington Heights, Ill.). Stability testing also can be performed on the monoclonal antibody by placing an aliquot of the monoclonal antibody in continuous storage at 2–8° C. and assaying optical density (OD) readings throughout the course of a given period of time.

C. Use of Recombinant Proteins as Immunogens

It is within the scope of the present invention that recombinant proteins made as described herein can be utilized as immunogens in the production of polyclonal and monoclonal antibodies, with corresponding changes in reagents and techniques known to those skilled in the art.

Example 15
Purification of Serum Antibodies Which Specifically Bind to CS193 Peptides Immune sera, obtained as described hereinabove in Examples 13 and/or 14, is affinity purified using immobilized synthetic peptides prepared as described in Example 10, or recombinant proteins prepared as described in Example 11. An IgG fraction of the antiserum is obtained by passing the diluted, crude antiserum over a Protein A column (Affi-Gel protein A, Bio-Rad, Hercules, Calif.). Elution with a buffer (Binding Buffer, supplied by the manufacturer) removes substantially all proteins that are not immunoglobulins. Elution with 0.1 M buffered glycine (pH 3) gives an immunoglobulin preparation that is substantially free of albumin and other serum proteins.

Immunoaffinity chromatography is performed to obtain a preparation with a higher fraction of specific antigen-binding antibody. The peptide used to raise the antiserum is immobilized on a chromatography resin, and the specific antibodies directed against its epitopes are adsorbed to the resin. After washing away non-binding components, the specific antibodies are eluted with 0.1 M glycine buffer, pH 2.3. Antibody fractions are immediately neutralized with 1.0M Tris buffer (pH 8.0) to preserve immunoreactivity. The chromatography resin chosen depends on the reactive groups present in the peptide. If the peptide has an amino group, a resin such as Affi-Gel 10 or Affi-Gel 15 is used (Bio-Rad, Hercules, Calif.). If coupling through a carboxy group on the peptide is desired, Affi-Gel 102 can be used (Bio-Rad, Hercules, Calif.). If the peptide has a free sulfhydryl group, an organomercurial resin such as Affi-Gel 501 can be used (Bio-Rad, Hercules, Calif.).

Alternatively, spleens can be harvested and used in the production of hybridomas to produce monoclonal antibodies following routine methods known in the art as described hereinabove.

Example 16
Western Blotting of Tissue Samples

Protein extracts are prepared by homogenizing tissue samples in 0.1M Tris-HCl (pH 7.5), 15% (w/v) glycerol, 0.2 mM EDTA, 1.0 mM 1,4-dithiothreitol, 10 µg/ml leupeptin and 1.0 mM phenylmethylsulfonylfluoride (Kain et al., *Biotechniques,* 17:982 (1994)). Following homogenization, the homogenates are centrifuged at 4° C. for 5 minutes to separate supernate from debris. For protein quantitation, 3–10 µl of supernate are added to 1.5 ml of bicinchoninic acid reagent (Sigma, St. Louis, Mo.), and the resulting absorbance at 562 nm is measured.

For SDS-PAGE, samples are adjusted to desired protein concentration with Tricine Buffer (Novex, San Diego, Calif.), mixed with an equal volume of 2× Tricine sample buffer (Novex, San Diego, Calif.), and heated for 5 minutes at 100° C. in a thermal cycler. Samples are then applied to a Novex 10–20% Precast Tricine Gel for electrophoresis. Following electrophoresis, samples are transferred from the gels to nitrocellulose membranes in Novex Tris-Glycine Transfer buffer. Membranes are then probed with specific anti-peptide antibodies using the reagents and procedures provided in the Western Lights or Western Lights Plus (Tropix, Bedford, Mass.) chemiluminesence detection kits. Chemiluminescent bands are visualized by exposing the developed membranes to Hyperfilm ECL (Amersham, Arlington Heights, Ill.).

Competition experiments are carried out in an analogous manner as above, with the following exception; the primary antibodies (anti-peptide polyclonal antisera) are pre-incubated for 30 minutes at room temperature with varying concentrations of peptide immunogen prior to exposure to the nitrocellulose filter. Development of the Western is performed as above.

After visualization of the bands on film, the bands can also be visualized directly on the membranes by the addition and development of a chromogenic substrate such as 5-bromo-4chloro-3-indolyl phosphate (BCIP). This chromogenic solution contains 0.016% BCIP in a solution containing 100 mM NaCl, 5 mM $MgCl_2$ and 100 mM Tris-HCl (pH 9.5). The filter is incubated in the solution at room temperature until the bands develop to the desired intensity. Molecular mass determination is made based upon the mobility of pre-stained molecular weight standards (Novex, San Diego, Calif.) or biotinylated molecular weight standards (Tropix, Bedford, Mass.).

Example 17
EIA Microtiter Plate Assay

The immunoreactivity of antiserum obtained from rabbits as described in Example 14 was determined by means of a microtiter plate EIA, as follows. Briefly, synthetic peptides, SEQUENCE ID NO 42, SEQUENCE ID NO 43, SEQUENCE ID NO 44, and SEQUENCE ID NO 45, prepared as described in Example 10, were dissolved in carbonate buffer (50 mM, pH 9.6) to a final concentration of 2 µg/ml. Next, 100 µl of the peptide or protein solution were placed in each well of an Immulon 2® microtiter plate (Dynex Technologies, Chantilly, Va.). The plate was incubated overnight at room temperature and then washed four times with deionized water. The wells were blocked by adding 125 µl of a suitable protein blocking agent, such as Superblock® (Pierce Chemical Company, Rockford, Ill.), to each well and then immediately discarding the solution. This blocking procedure was performed three times. Antiserum obtained from immunized rabbits, prepared as previously described, was diluted in a protein blocking agent (e.g., a 3% Superblock® solution) in PBS containing 0.05% Tween-20® (monolaurate polyoxyethylene ether) (Sigma Chemical Company, St. Louis, Mo.) and 0.05% sodium azide at dilutions of 1:100, 1:500, 1:2500, 1:12,500, and 1:62,500 and placed in each well of the coated microtiter plate. The wells were then incubated for three hours at room temperature. Each well was washed four times with deionized water. One hundred microliters of alkaline phosphatase-conjugated goat anti-rabbit IgG antiserum (Southern Biotech, Birmingham, Ala.) diluted 1:2000 in 3% Superblock® solution in phosphate buffered saline containing 0.05% Tween 20® and 0.05% sodium azide, were added to each well. The wells were incubated for two hours at room temperature. Next, each well was washed four times with deionized water. One hundred microliters of paranitrophenyl phosphate substrate (Kirkegaard and Perry Laboratories, Gaithersburg, Md.) then were added to each well. The wells were incubated for thirty minutes at room temperature. The absorbance at 405 nm was read in each well. Positive reactions were identified by an increase in absorbance at 405 nm in the test well above that absorbance given by a non-immune serum (negative control). A positive reaction was indicative of the presence of detectable anti-CS193 antibodies. Titers of the anti-peptide antisera were calculated from the previously described dilutions of antisera and defined as the calculated dilution, where $A_{405nm}=0.5$ OD.

Example 18

Coating of Solid Phase Particles

A. Coating of Microparticles With Antibodies Which Specifically Bind to CS193 Antigen Affinity purified antibodies which specifically bind to CS193 protein (see Example 15) are coated onto microparticles of polystyrene, carboxylated polystyrene, polymethylacrylate or similar particles having a radius in the range of about 0.1 to 20 μm. Microparticles may be either passively or actively coated. One coating method comprises coating EDAC (1-(3-dimethylaminopropyl)-3-ethylcarbodiimide hydrochloride (Aldrich Chemical Co., Milwaukee, Wis.) activated carboxylated latex microparticles with antibodies which specifically bind to CS193 protein, as follows. Briefly, a final 0.375% solid suspension of resin washed carboxylated latex microparticles (available from Bangs Laboratories, Carmel, Ind. or Serodyn, Indianapolis, Ind.) are mixed in a solution containing 50 mM MES buffer, pH 4.0 and 150 mg/l of affinity purified anti-CS193 antibody (see Example 14) for 15 min in an appropriate container. EDAC coupling agent is added to a final concentration of 5.5 μg/ml to the mixture and mixed for 2.5 h at room temperature.

The microparticles then are washed with 8 volumes of a Tween 20®/sodium phosphate wash buffer (pH 7.2) by tangential flow filtration using a 0.2 μm Microgon Filtration module. Washed microparticles are stored in an appropriate buffer which usually contains a dilute surfactant and irrelevant protein as a blocking agent, until needed.

B. Coating of ¼ Inch Beads

Antibodies which specifically bind to CS193-antigen also may be coated on the surface of ¼ inch polystyrene beads by routine methods known in the art (Snitman et al, U.S. Pat. No. 5,273,882, incorporated herein by reference) and used in competitive binding or EIA sandwich assays.

Polystyrene beads first are cleaned by ultrasonicating them for about 15 seconds in 10 mM $NaHCO_3$ buffer at pH 8.0. The beads then are washed in deionized water until all fines are removed. Beads then are immersed in an antibody solution in 10 mM carbonate buffer, pH 8 to 9.5. The antibody solution can be as dilute as 1 μg/ml in the case of high affinity monoclonal antibodies or as concentrated as about 500 μg/ml for polyclonal antibodies which have not been affinity purified. Beads are coated for at least 12 hours at room temperature, and then they are washed with deionized water. Beads may be air dried or stored wet (in PBS, pH 7.4). They also may be overcoated with protein stabilizers (such as sucrose) or protein blocking agents used as non-specific binding blockers (such as irrelevant proteins, Carnation skim milk, Superblock®, or the like).

Example 19

Microparticle Enzyme Immunoassay (MEIA)

CS193 antigens are detected in patient test samples by performing a standard antigen competition EIA or antibody sandwich EIA and utilizing a solid phase such as microparticles (MEIA). The assay can be performed on an automated analyzer such as the IMx® Analyzer (Abbott Laboratories, Abbott Park, Ill.).

A. Antibody Sandwich EIA

Briefly, samples suspected of containing CS193 antigen are incubated in the presence of anti-CS193 antibody-coated microparticles (prepared as described in Example 17) in order to form antigen/antibody complexes. The microparticles then are washed and an indicator reagent comprising an antibody conjugated to a signal generating compound (i.e., enzymes such as alkaline phosphatase or horseradish peroxide) is added to the antigen/antibody complexes or the microparticles and incubated. The microparticles are washed and the bound antibody/antigen/antibody complexes are detected by adding a substrate (e.g., 4-methyl umbelliferyl phosphate (MUP), or OPD/peroxide, respectively), that reacts with the signal generating compound to generate a measurable signal. An elevated signal in the test sample, compared to the signal generated by a negative control, detects the presence of CS193 antigen. The presence of CS193 antigen in the test sample is indicative of a diagnosis of a GI tract disease or condition, such as GI tract cancer.

B. Competitive Binding Assay

The competitive binding assay uses a peptide or protein that generates a measurable signal when the labeled peptide is contacted with an anti-peptide antibody coated microparticle. This assay can be performed on the IMx® Analyzer (available from Abbott Laboratories, Abbott Park, Ill.). The labeled peptide is added to the CS193 antibody-coated microparticles (prepared as described in Example 17) in the presence of a test sample suspected of containing CS193 antigen, and incubated for a time and under conditions sufficient to form labeled CS193 peptide (or labeled protein)/bound antibody complexes and/or patient CS193 antigen/bound antibody complexes. The CS193 antigen in the test sample competes with the labeled CS193 peptide (or CS193 protein) for binding sites on the microparticle. CS193 antigen in the test sample results in a lowered binding of labeled peptide and antibody coated microparticles in the assay since antigen in the test sample and the CS193 peptide or CS193 protein compete for antibody binding sites. A lowered signal (compared to a control) indicates the presence of CS193 antigen in the test sample. The presence of CS193 antigen suggests the diagnosis of a GI tract disease or condition, such as GI tract cancer.

The CS193 polynucleotides and the proteins encoded thereby which are provided and discussed hereinabove are useful as markers of GI tract tissue disease, especially GI tract cancer. Tests based upon the appearance of this marker in a test sample such as blood, plasma or serum can provide low cost, non-invasive, diagnostic information to aid the physician to make a diagnosis of cancer, to help select a therapy protocol, or to monitor the success of a chosen therapy. This marker may appear in readily accessible body fluids such as blood, urine or stool as antigens derived from the diseased tissue which are detectable by immunological methods. This marker may be elevated in a disease state, altered in a disease state, or be a normal protein of the GI tract which appears in an inappropriate body compartment.

We claim:

1. A purified polynucleotide having 90% identity to a polynucleotide sequence selected from the group consisting of:
SEQ ID NO:1, SEQ ID NO:2, SEQ ID NO:3, SEQ ID NO:4, SEQ ID NO;5, SEQ ID NO:6, SEQ ID NO:7, SEQ ID NO:8, SEQ ID NO:9, SEQ ID NO: 10; SEQ ID NO:11, SEQ ID NO:12, SEQ ID NO:13, SEQ ID NO:14, SEQ ID NO:15, SEQ ID NO:16, SEQ ID NO:17, SEQ ID NO:18, and complements thereof.

2. The purified polynucleotide of claim 1, wherein said polynucleotide is produced by recombinant techniques.

3. The purified polynucleotide of claim 1, wherein said polynucleotide is produced by synthetic techniques.

4. The purified polynucleotide of claim 1, wherein said polynucleotide comprises a sequence encoding at least one epitope.

5. A recombinant expression system comprising a nucleic acid sequence including an open reading same operably linked to a control sequence compatible with a desired host, the nucleic acid sequence having 90% identity to a sequence selected from the group consisting of:
SEQ ID NO:1, SEQ ID NO:2, SEQ ID NO:3, SEQ ID NO;4, SEQ ID NO:5, SEQ ID NO:6, SEQ ID NO:7, SEQ ID NO:8, SEQ ID NO:9, SEQ ID NO:10; SEQ ID NO:11, SEQ ID NO:12, SEQ ID NO:13, SEQ ID NO:14, SEQ ID NO:15, SEQ ID NO:16, SEQ ID NO:17, SEQ ID NO:18, and complements thereof.

6. A cell transfected with the recombinant expression system of claim 5.

7. A cell transfected with a nucleic acid sequence encoding at least one epitope, said nucleic acid sequence having 90% identity to a sequence selected from the group consisting of:
SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:11, SEQ ID NO:12, SEQ ID NO:13, SEQ ID NO:14, SEQ ID NO:15, SEQ ID NO:16, SEQ ID NO:17, SEQ ID NO:18 and complements thereof.

8. A composition of matter comprising a polynucleotide, the polynucleotide having 90% identity to a sequence selected from the group consisting of:
SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10; SEQ ID NO:11, SEQ ID NO: 12, SEQ ID NO:13, SEQ ID NO:14, SEQ ID NO:15, SEQ ID NO:16, SEQ ID NO:17, SEQ ID NO:18 and complements thereof.

9. A purified polynucleotide which codes for a protein comprising an amino acid sequence having at least 90% identity to SEQ ID NO:16.

10. A purified polynucleotide which codes for a protein comprising an amino acid sequence having to 90% identity to a sequence selected from the group consisting of: SEQ ID NO:16, SEQ ID NO:17, SEQ ID NO:18 and complements thereof.

11. A purified polynucleotide sequence selected from the group consisting of:

SEQ ID NOS:1–18, and degenerate codon equivalents thereof.

12. A recombinant expression system comprising a nucleic acid sequence including an open reading frame operably linked to a control sequence compatible with a desired host, the nucleic acid sequence selected from the group consisting of:

SEQ ID NOS:1–18, and degenerate codon equivalents thereof.

13. A cell transfected with a nucleic acid sequence encoding at least one epitope, said nucleic acid sequence selected from the group consisting of:

SEQ ID NOS:1–18, and degenerate codon equivalents thereof.

14. A composition of matter comprising a polynucleotide, the polynucleotide having a sequence selected from the group consisting of:

SEQ ID NOS:1–18, and degenerate codon equivalents thereof.

15. A purified polynucleotide comprising SEQ ID NO:16.

16. A purified polynucleotide having a sequence selected from the group consisting of: SEQ ID NO:16, SEQ ID NO:17, SEQ ID NO:18, and degenerate codon equivalents thereof.

* * * * *

UNITED STATES PATENT AND TRADEMARK OFFICE
CERTIFICATE OF CORRECTION

PATENT NO.    : 6,368,792 B1
DATED         : April 9, 2002
INVENTOR(S)   : Patricia A. Billing-Medel et al.

It is certified that error appears in the above-identified patent and that said Letters Patent is hereby corrected as shown below:

<u>Column 2,</u>
Lines 36 and 56, replace "the word "supra" with the italic word -- *supra* --.

<u>Column 16,</u>
Line 32, replace the word "Reagents" with the italic word -- *Reagents* --.

<u>Column 18,</u>
Line 49, replace "fluorescent in situ" with italic the letter "f" in "fluoresent" and italic the words "in situ".
Line 58, replace the words "in situ" with the italic words -- *in situ* --.
Line 64, replace the words "Probe Assays" with the italic words -- *Probe Assaus* --.

<u>Column 23,</u>
Line 9, replace the word "Dupont" with the word -- DuPont --.
Line 33, replace the words "patent application" with the words -- Patent Application --.

<u>Column 24,</u>
Line 10, replace the words "Drug Screening and Gene Therapy" with the italic words -- *Drug Screening and Gene Therapy* --.
Line 24, replace the words "in vivo" with the italic words -- *in vivo* --.

<u>Column 25,</u>
Line 25, replace the words "in vivo" with the italic word -- *in vivo* --.

<u>Column 26,</u>
Line 47, replace the words "in vivo" with the italic words -- *in vivo* --.
Line 58, replace the words "Recombinant Technology" with the italic words -- *Recombinant Technology* --.

<u>Column 27,</u>
Line 54, replace the words "streptomvces sp." with the italic words -- *streptomyces sp.* --.

<u>Column 29,</u>
Line 45, replace the words "Pseudomonas, Streptomyces and Staphylococcus," with the italic words -- *Pseudomonas, Streptomyces and Staphylococcus* --.

<u>Column 31,</u>
Line 53, replace the word "supra" with the italic word -- *supra* --.

UNITED STATES PATENT AND TRADEMARK OFFICE
CERTIFICATE OF CORRECTION

PATENT NO. : 6,368,792 B1
DATED : April 9, 2002
INVENTOR(S) : Patricia A. Billing-Medel et al.

It is certified that error appears in the above-identified patent and that said Letters Patent is hereby corrected as shown below:

Column 32,
Line 17, replace the word "(supra)" with the italic word -- (supra) --.
Line 44, replace the word "in vitro" with the italic word -- in vitro --.

Column 33,
Line 44, replace the word "Immunoassays" with the italic word -- Immunoassays --.

Column 39,
Line 32, replace the word "See" with the italic word -- See --.

Column 41,
Lines 29 and 48, replace "0-4°C." with -- 0-4°C --.
Lines 29, 32, 42 and 48, replace "xg" with -- x g --.
Line 37, replace "37°C." with -- 37°C --.
Line 47, replace "-20°C." with -- -20°C --.
Line 55, replace "-70°C." with -- -70°C --.

Column 42,
Lines 1, 6, 9, 20 and 23, replace "xg" with -- x g --.
Lines 6 and 61, replace "4°C." with -- 4°C --.
Line 32, replace "-20°C." with -- 20°C --.
Line 42, replace "37°C." with -- 37°C --.

Column 43,
Lines 1, 2, 10 and 23, replace "xg" with -- x g --.
Line 2, replace "4°C." with -- 4°C --.
Line 14, replace "90°C." with -- 90°C --.
Line 21, replace "-20°C." with -- 20°C --.

Column 44,
Line 12, replace the words "Direct Protect" with the words -- "Direct ProtectTM" --.
Line 13, replace "37°C.," with -- 37°C, --.
Line 17, replace "-70°C." with -- -70°C --.
Line 19, replace "xg" with -- x g --.
Line 32, replace "the word "supra"" with the italic word -- supra --.

UNITED STATES PATENT AND TRADEMARK OFFICE
CERTIFICATE OF CORRECTION

PATENT NO. : 6,368,792 B1
DATED : April 9, 2002
INVENTOR(S) : Patricia A. Billing-Medel et al.

It is certified that error appears in the above-identified patent and that said Letters Patent is hereby corrected as shown below:

Column 45,
Lines 5, 14, 16 and 17, replace "42°C." with -- 42°C --.
Line 31, replace "68°C." with -- 68°C --.
Lines 39 and 48, replace the word "supra" with the italic word -- supra --.
Line 60, replace "4°C." with -- 4°C --.

Column 46,
Lines 15 and 22, replace "37°C." with -- 37°C --.
Line 18, replace "56°C." with -- 56°C --.
Line 55, replace "60°C - 70°C." with -- 60°C. -70°C --.
Line 56, replace "94°C., 1min; 55° - 70°C.,1min; 70°C., 2min." with -- 94°C, 1min; 55° - 70°C,1min; 70°C, 2min. --.

Column 47,
Line 2, replace "42°C." with -- 42°C --.
Line 3, replace "95°C." with -- 95°C --.
Line 11, replace "94°C." with -- 94°C --.
Line 12, replace "94°C., 45sec; 55°C., 45sec; and 72°C., 2min); a final extens" with -- 94°C, 45sec; 55°C, 45sec; and 72°C, 2min); a final extension --.
Line 13, replace "(72°C., 5min)" with -- (72°C, 5min) --.
Line 40, replace the word "see" with the italic word -- see --.
Line 46, replace "15°C." with -- 15°C --.
Line 66, replace "(60°C., 30min)," with -- (60°C, 30min) --.
Line 67, replace "(94°C., 40sec; 55 - 70°C., 60sec)," with -- (94°C, 40sec; 55 - 70°C,60sec), --.

Column 48,
Line 1, replace "(97°C., 5min; 15°C., 5min; 15°C. soak)." with -- (97°C, 5min; 15°C, 5min; 15°C soak). --.
Line 26, replace "Park, N.C.)." with -- Park, NC). --.

Column 49,
Line 52, replace "(94°C., 30seconds; 55°C., 30seconds; 72°C., 90seconds)" with -- (94°C, 30secconds; 55°C, 30seconds; 72°C, 90seconds) --.
Line 53, replace "72°C." with -- 72°C --.
Line 56, replace the word "supra" with the italic word -- supra --.

UNITED STATES PATENT AND TRADEMARK OFFICE
CERTIFICATE OF CORRECTION

PATENT NO. : 6,368,792 B1
DATED : April 9, 2002
INVENTOR(S) : Patricia A. Billing-Medel et al.

It is certified that error appears in the above-identified patent and that said Letters Patent is hereby corrected as shown below:

Column 50,
Line 9, replace "37°C.," with -- 37°C, --.
Lines 35 and 42, replace "37°C." with -- 37°C --.

Column 51,
Line 58, replace "(94°C., 1min; 65°C.,1.5min; 72°C., 3min)" with -- (94°C, 1min; 65°C, 1.5min; 72°C, 3min) --.
Line 59, replace "72°C." with -- 72°C --.

Column 52,
Lines 27, 44 and 46, replace the word "supra" with the italic word -- supra --.
Lines 34, 37 and 58, replace "37°C." with -- 37°C --.

Column 53,
Line 3, replace "37°C.," with -- 37°C, --.
Lines 11, 25, 39 and 61, replace the word "supra" with the italic word -- supra --.

Column 54,
Line 44, replace "4°C." with -- 4°C --.

Column 55,
Line 6, replace "90°C." with -- 90°C --.
Line 15, replace "27°C." with -- 27°C --.
Line 31, replace the words "in vivo" with the italic words -- in vivo --.

Column 58,
Line 44, replace "2 -8°C." with -- 2 -8°C --.
Line 45, replace "-20°C." with -- 20°C --.

Column 59,
Lines 4 and 12, replace "2-8°C." with -- 2-8°C --.
Line 5, replace "80°C." with -- 80°C --.
Line 65, replace "4°C." with -- 4°C --.

Column 60,
Line 7, replace "100°C." with -- 100°C --.
Line 65, replace "(Southern Biotech Birmingham, Ala.)" with -- (Southern Biotech Birmingham, AB) --.

UNITED STATES PATENT AND TRADEMARK OFFICE
CERTIFICATE OF CORRECTION

PATENT NO. : 6,368,792 B1
DATED : April 9, 2002
INVENTOR(S) : Patricia A. Billing-Medel et al.

It is certified that error appears in the above-identified patent and that said Letters Patent is hereby corrected as shown below:

Column 73,
Line 11, replace "TCCTGCTGC 1020" with -- TCCTGCTGCA 1020 --.
Line 13, replace "CCACTATTG 1080" with -- CCACTATTGT 1080 --.
Line 15, replace "CAGGATTAC 1140" with -- CAGGATTACC 1140 --.
Line 17, replace "TTCAGGTGA 1200" with -- TTCAGGTGAT 1200 --.
Line 19, replace "ATGGGGAGG 1260" with -- ATGGGGAGGA 1260 --.
Line 21, replace "TTCATTTTA 1320" with -- TTCATTTTAT 1320 --.
Line 23, replace "CAGGAGGAA 1380" with -- CAGGAGGAAG 1380 --.
Line 25, replace "TTGGGGCTC 1440" with -- TTGGGGCTCT 1440 --.
Line 27, replace "AGGGATTAA 1500" with -- AGGGATTAAC 1500 --.
Line 29, replace "TGGGAAAGG 1560" with -- TGGGAAAGGA 1560 --.
Line 31, replace "GGGATCCCA 1620" with -- GGGATCCCAG 1620 --.
Line 33, replace "ATCTCAGTA 1680" with -- ATCTCAGTAT 1680 --.
Line 35, replace "CGAACCCAG 1740" with -- CGAACCCAGA 1740 --.
Line 37, replace "CAATCACAG 1800" with -- CAATCACAGT 1800 --.
Line 39, replace "TTTACGCAG 1860" with -- TTTACGCAGA 1860 --.
Line 41, replace "TTGAATCAC 1920" with -- TTGAATCACA 1920 --.
Line 43, replace "ATTCTTTCA 1980" with -- ATTCTTTCAA 1980 --.
Line 45, replace "GATATAGCT 2040" with -- GATATAGCTT 2040 --.
Line 47, replace "CTCCACTGA 2100" with -- CTCCACTGAA 2100 --.
Line 49, replace "ACCCGCCAA 2160" with -- ACCCGCCAAG 2160 --.
Line 51, replace "CAGCATCCG 2220" with -- CAGCATCCGG 2220 --.
Line 53, replace "ACCCACCAA 2280" with -- ACCCACCAAG 2280 --.
Line 55, replace "CATGGACAG 2340" with -- CATGGACAGC 2340 --.
Line 57, replace "TAAGTGCAA 2400" with -- TAAGTGCAAG 2400 --.
Line 59, replace "CTGATCTGT 2460" with -- CTGATCTGTA 2460 --.
Line 61, replace "TCTCAGAAG 2520" with -- TCTCAGAAGA 2520 --.
Line 63, replace "TGACATCAA 2580" with -- TGACATCAAA 2580 --.
Line 65, replace "ATGACATTG 2640" with -- ATGACATTGA 2640 --.
Line 67, replace "TTAATATTT 2700" with -- TTAATATTTC 2700 --.
Line 69, replace "TAAGTACCA 2760" with -- TAAGTACCAC 2760 --.
Line 71, replace "TTTTAAAAA 2820" with -- TTTTAAAAAA 2820 --.
Line 73, replace "TGTGATCAT 2880" with -- TGTGATCATA 2880 --.
Line 75, replace "AAAAACACT 2940" with -- AAAAACACTC 2940 --.
Line 77, replace "GTTATTTTA 3000" with -- GTTATTTTAT 3000 --.

UNITED STATES PATENT AND TRADEMARK OFFICE
CERTIFICATE OF CORRECTION

PATENT NO. : 6,368,792 B1
DATED : April 9, 2002
INVENTOR(S) : Patricia A. Billing-Medel et al.

It is certified that error appears in the above-identified patent and that said Letters Patent is hereby corrected as shown below:

Column 75,
Line 46, replace "AAAAATCTT 1020" with -- AAAAATCTTC 1020 --.
Line 48, replace "TATTTCTGA 1080" with -- TATTTCTGAA 1080 --.
Line 50, replace "GATGTCGGA 1140" with -- GATGTCGGAA 1140 --.
Line 52, replace "AGATTAAAA 1200" with -- AGATTAAAAT 1200 --.
Line 54, replace "AAAGATCCT 1260" with -- AAAGATCCTT 1260 --.
Line 56, replace "ATGATATTT 1320" with -- ATGATATTTC 1320 --.
Line 58, replace "TAAAGGAGA 1380" with -- TAAAGGAGAG 1380 --.

Column 77,
Line 26, replace "AGCAAAACA 1020" with -- AGCAAAACAT 1020 --.
Line 28, replace "TGATAGTAC 1080" with -- TGATAGTACT 1080 --.
Line 30, replace "CACACTCAT 1140" with -- CACACTCATG 1140 --.
Line 32, replace "TAAATATGC 1200" with -- TAAATATGCA 1200 --.
Line 34, replace "GCTGCTGAC 1260" with -- GCTGCTGACT 1260 --.
Line 36, replace "TGGGGCCAT 1320" with -- TGGGGCCATT 1320 --.
Line 38, replace "GAGCAAGAT 1380" with -- GAGCAAGATA 1380 --.
Line 40, replace "CATTGATGC 1440" with -- CATTGATGCT 1440 --.
Line 42, replace "GCTCGAAAG 1500" with -- GCTCGAAAGT 1500 --.
Line 44, replace "TGATAGTAC 1560" with -- TGATAGTACA 1560 --.
Line 46, replace "TATTTCTCT 1620" with -- TATTTCTCTC 1620 --.
Line 48, replace "CAAAATGGC 1680" with -- CAAAATGGCC 1680 --.
Line 50, replace "TCAAGCCAA 1740" with -- TCAAGCCAAA 1740 --.
Line 52, replace "TTCTGTGCC 1800" with -- TTCTGTGCCT 1800 --.
Line 54, replace "CCCAATGAT 1860" with -- CCCAATGATT 1860 --.
Line 56, replace "GACTGCTTT 1920" with -- GACTGCTTTC 1920 --.
Line 58, replace "TGCAGGCGC 1980" with -- TGCAGGCGCT 1980 --.
Line 60, replace "AGAAAATGG 2040" with -- AGAAAATGGC 2040 --.
Line 62, replace "AAAATTACG 2100" with -- AAAATTACGG 2100 --.
Line 64, replace "AATTGAAGC 2160" with -- AATTGAAGCA 2160 --.
Line 66, replace "TTTCAGCCG 2220" with -- TTTCAGCCGA 2220 --.
Line 68, replace "GCCTGACCA 2280" with -- GCCTGACCAA 2280 --.
Line 70, replace "GATTATTCT 2340" with -- GATTATTCTT 2340 --.
Line 72, replace "TATCATAAG 2400" with -- TATCATAAGA 2400 --.
Line 74, replace "AGTAATAC 2460" with -- AGTAATACT 2460 --.
Line 76, replace "ACCAGAAA 2520" with -- ACCAGAAAT 2520 --.
Line 78, replace "TAAAGCAA 2580" with -- TAAAGCAAT 2580 --.

UNITED STATES PATENT AND TRADEMARK OFFICE
CERTIFICATE OF CORRECTION

PATENT NO. : 6,368,792 B1
DATED : April 9, 2002
INVENTOR(S) : Patricia A. Billing-Medel et al.

It is certified that error appears in the above-identified patent and that said Letters Patent is hereby corrected as shown below:

Column 79,
Line 1, replace "AGCAAATCC 2640" with -- AGCAAATCCT 2640 --.
Line 3, replace "TAATTCTGG 2700" with -- TAATTCTGGA 2700 --.
Line 5, replace "TAACTTTAT 2760" with -- TAACTTTATT 2760 --.
Line 7, replace "CTAGAAGAG 2820" with -- CTAGAAGAGA 2820 --.
Line 9, replace "TTCATCCCA 2880" with -- TTCATCCCAT 2880 --.
Line 11, replace "TTTGATTAA 2940" with -- TTTGATTAAA 2940 --.
Line 13, replace "TTCATTTAT 3000" with -- TTCATTTATT 3000 --.
Line 15, replace "TGATACCTG 3060" with -- TGATACCTGG 3060 --.
Line 17, replace "TCAAGAAAT 3120" with -- TCAAGAAATT 3120 --.
Line 19, replace "CAACATTTG 3180" with -- CAACATTTGG 3180 --.

Column 95,
Line 62, replace the word "same" with the word -- frame --.

Signed and Sealed this

Fifth Day of August, 2003

JAMES E. ROGAN
*Director of the United States Patent and Trademark Office*